United States Patent
Lane

(10) Patent No.: US 10,964,421 B2
(45) Date of Patent: Mar. 30, 2021

(54) METHOD AND APPARATUS FOR DELIVERING A SUBSTANCE TO AN INDIVIDUAL

(71) Applicant: WELCH ALLYN, INC., Skaneateles Falls, NY (US)

(72) Inventor: John A. Lane, Skaneateles Falls, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 1092 days.

(21) Appl. No.: 14/920,056

(22) Filed: Oct. 22, 2015

(65) Prior Publication Data

US 2017/0112434 A1    Apr. 27, 2017

(51) Int. Cl.

| | |
|---|---|
| *G16H 20/17* | (2018.01) |
| *G16C 20/30* | (2019.01) |
| *A61B 5/00* | (2006.01) |
| *A61M 37/00* | (2006.01) |
| *A61B 5/024* | (2006.01) |
| *A61B 5/021* | (2006.01) |
| *A61B 5/01* | (2006.01) |

(52) U.S. Cl.
CPC ............. *G16H 20/17* (2018.01); *A61B 5/01* (2013.01); *A61B 5/021* (2013.01); *A61B 5/024* (2013.01); *A61B 5/4839* (2013.01); *A61B 5/4848* (2013.01); *A61B 5/6814* (2013.01); *A61B 5/6846* (2013.01); *A61B 5/68335* (2017.08); *A61M 37/0015* (2013.01); *G16C 20/30* (2019.02); *A61M 2037/0023* (2013.01); *A61M 2205/33* (2013.01); *A61M 2205/502* (2013.01); *A61M 2230/005* (2013.01)

(58) Field of Classification Search
None
See application file for complete search history.

(56) References Cited

U.S. PATENT DOCUMENTS

| | | | |
|---|---|---|---|
| 3,703,890 A | 11/1972 | Saunders | |
| 3,814,095 A | 6/1974 | Lubens | |
| 4,329,999 A | 5/1982 | Phillips | |
| D379,356 S | 5/1997 | Liu et al. | |
| 5,688,232 A | 11/1997 | Flower | |
| 5,879,292 A | 3/1999 | Sternberg et al. | |
| 5,887,590 A | 3/1999 | Price et al. | |
| 6,443,913 B1 * | 9/2002 | Kania | A61B 5/11 128/202.11 |
| 7,717,841 B2 * | 5/2010 | Brendley | A61M 21/00 348/148 |
| 8,315,687 B2 | 11/2012 | Cross et al. | |
| 8,504,323 B2 | 8/2013 | Coradi | |
| 8,529,457 B2 | 9/2013 | Devot et al. | |
| 8,688,189 B2 | 4/2014 | Shennib | |
| 8,795,174 B2 | 8/2014 | Manicka et al. | |
| 2002/0143290 A1 * | 10/2002 | Bui | A61M 5/172 604/67 |
| 2003/0060753 A1 * | 3/2003 | Starkweather | A61M 5/14276 604/66 |
| 2004/0153018 A1 | 8/2004 | Brown | |
| 2005/0020996 A1 * | 1/2005 | Hartlaub | A61M 5/14276 604/500 |
| 2005/0149362 A1 | 7/2005 | Peterson et al. | |
| 2005/0154264 A1 | 7/2005 | Lecompte et al. | |
| 2005/0245852 A1 | 11/2005 | Ellefson et al. | |
| 2006/0002988 A1 | 1/2006 | Ellefson et al. | |
| 2007/0049461 A1 | 3/2007 | Kim et al. | |
| 2007/0066526 A1 | 3/2007 | Mochly-Rosen et al. | |
| 2007/0073132 A1 | 3/2007 | Vosch | |
| 2007/0077287 A1 | 4/2007 | Goodrich | |
| 2008/0269843 A1 * | 10/2008 | Gerber | A61N 1/36514 607/62 |
| 2009/0043289 A1 * | 2/2009 | Zhang | A61B 5/0031 604/891.1 |
| 2009/0062670 A1 | 3/2009 | Sterling et al. | |
| 2009/0076340 A1 | 3/2009 | Libbus et al. | |
| 2009/0076345 A1 | 3/2009 | Manicka et al. | |
| 2009/0076397 A1 | 3/2009 | Libbus et al. | |
| 2009/0076410 A1 | 3/2009 | Libbus et al. | |

(Continued)

FOREIGN PATENT DOCUMENTS

| | | |
|---|---|---|
| WO | 2007072412 A2 | 6/2007 |
| WO | 2011094819 A1 | 8/2011 |

(Continued)

OTHER PUBLICATIONS

Murdin, L., Golding, J. & Bronstein, A. Managing motion sickness. British Medical Journal 343, (2011).*

Becker, R. H. A.; Frick, A. D.; Nosek, L.; Heinemann, L.; Rave, K. Dose-Response Relationship of Insulin Glulisine in Subjects With Type 1 Diabetes. Diabetes Care 2007, 30 (10), 2506-2507.*

"Texas Instruments launches industry's first highly integrated NFC sensor transponder for industrial, medical, wearables and Internet of Things (IoT) applications", Texas Instruments News Releases, Apr. 10, 2015, 2 pages.

(Continued)

*Primary Examiner* — Soren Harward
(74) *Attorney, Agent, or Firm* — Lee & Hayes, P.C.

(57) ABSTRACT

Aspects of the subject disclosure may include, for example, detecting, by a substance delivery system coupled to a body part of an individual, an input signal not associated with a biological measurement of the individual, determining from the input signal, by the substance delivery system, whether delivering a dosage of a substance stored in the substance delivery system is needed and conforms to a dosage policy, and responsive to determining from the input signal that delivery of the dosage of the substance is needed and conforms to the dosage policy, initiating, by the substance delivery system, delivery of the dosage of the substance to the body part of the individual. Other embodiments are disclosed.

20 Claims, 27 Drawing Sheets

(56) References Cited

U.S. PATENT DOCUMENTS

| | | |
|---|---|---|
| 2009/0076559 A1 | 3/2009 | Libbus et al. |
| 2009/0131861 A1* | 5/2009 | Braig ............... A61B 5/1427 604/66 |
| 2009/0151198 A1 | 6/2009 | Villegas |
| 2009/0171589 A1* | 7/2009 | Kovatchev ........... G16H 50/20 702/19 |
| 2009/0192402 A1 | 7/2009 | Corn et al. |
| 2009/0209896 A1 | 8/2009 | Selevan |
| 2009/0292194 A1 | 11/2009 | Libbus et al. |
| 2009/0326510 A1* | 12/2009 | Haefner ............... A61B 5/021 604/503 |
| 2010/0069889 A1* | 3/2010 | Solomon ............... G16H 50/50 604/890.1 |
| 2010/0145262 A1* | 6/2010 | Bengtsson ......... A61B 5/14532 604/66 |
| 2011/0144540 A1* | 6/2011 | Shen ................ A61M 5/14276 600/587 |
| 2011/0218418 A1 | 9/2011 | Green et al. |
| 2011/0245695 A1 | 10/2011 | Kawano et al. |
| 2011/0245711 A1 | 10/2011 | Katra et al. |
| 2012/0029306 A1 | 2/2012 | Paquet et al. |
| 2012/0029307 A1 | 2/2012 | Paquet et al. |
| 2012/0029309 A1 | 2/2012 | Paquet et al. |
| 2012/0029312 A1 | 2/2012 | Beaudry et al. |
| 2012/0029313 A1 | 2/2012 | Burdett et al. |
| 2012/0029316 A1 | 2/2012 | Raptis et al. |
| 2012/0029372 A1 | 2/2012 | Haefner et al. |
| 2012/0130196 A1 | 5/2012 | Jain et al. |
| 2012/0130203 A1 | 5/2012 | Stergiou et al. |
| 2013/0011819 A1 | 1/2013 | Horseman et al. |
| 2013/0085347 A1 | 4/2013 | Manicka et al. |
| 2013/0123719 A1* | 5/2013 | Mao ...................... G06F 19/00 604/304 |
| 2013/0183209 A1* | 7/2013 | Richter ............. A61M 5/16804 422/403 |
| 2013/0192071 A1 | 8/2013 | Esposito et al. |
| 2013/0331665 A1 | 12/2013 | Libbus et al. |
| 2013/0338448 A1 | 12/2013 | Libbus et al. |
| 2014/0046144 A1 | 2/2014 | Jayaraman et al. |
| 2014/0128803 A1* | 5/2014 | Dobbles ............... G16H 40/63 604/66 |
| 2014/0176369 A1 | 6/2014 | Choi et al. |
| 2014/0184422 A1* | 7/2014 | Mensinger ........... A61B 5/0004 340/870.02 |
| 2014/0266959 A1 | 9/2014 | Xue et al. |
| 2014/0288396 A1 | 9/2014 | LeBoeuf et al. |
| 2014/0310298 A1 | 10/2014 | Stivoric et al. |
| 2014/0330136 A1 | 11/2014 | Manicka et al. |
| 2015/0073251 A1 | 3/2015 | Mazar |
| 2015/0126896 A1 | 5/2015 | AlHazme |
| 2015/0250426 A1 | 9/2015 | Muehlsteff |
| 2015/0265212 A1 | 9/2015 | Bruekers et al. |
| 2017/0112388 A1 | 4/2017 | Quinn et al. |
| 2017/0112453 A1 | 4/2017 | Quinn et al. |
| 2018/0035900 A1 | 2/2018 | Stebbins |
| 2018/0035953 A1 | 2/2018 | Quinn et al. |
| 2018/0075199 A1 | 3/2018 | Meyerson et al. |

FOREIGN PATENT DOCUMENTS

| | | |
|---|---|---|
| WO | 2012140537 A1 | 10/2012 |
| WO | 2014031944 A1 | 2/2014 |
| WO | 2014063160 A1 | 4/2014 |
| WO | 2014153017 A1 | 9/2014 |
| WO | 2014160764 A1 | 10/2014 |

OTHER PUBLICATIONS

Borreli, Lizette, "Smartphone Stress Hormone Test App May Be Able to Measure Cortisol Levels: What Are Signs of Stress?", Medical Daily, Jul. 7, 2014, 2 pages.
Forkan, Abdur et al., "Context-aware Cardiac Monitoring for Early Detection of Heart Diseases", Computing in Cardiology; 40, 2013, 277-280.
Jovanov, Emil et al., "A wireless body area network of intelligent motion sensors for computer assisted physical rehabilitation", Journal of NeuroEngineering and Rehabilitation, 2005, 10 pages.
Jovanov, Emil et al., "Stress Monitoring Using a Distributed Wireless Intelligent Sensor System", IEEE Engineering in Medicine and Biology Magazine, 2003.
Sano, Akane et al., "Stress Recognition Using Wearable Sensors and Mobile Phones", Humaine Association Conference on Affective Computing and Intelligent Interaction, 2013, 6 pages.
Sun, Feng-Tso , "Activity-aware Mental Stress Detection Using Physiological Sensors", Carnegie Mellon University, 2015, 20 pages.
Talbot, David , "Wrist Sensor Tells You How Stressed Out You Are", MIT Technology Review, Dec. 20, 2012, 4 pgs.
PCT/US2016/051312, International Search Report and Written Opinion, dated Dec. 27, 2016.

\* cited by examiner

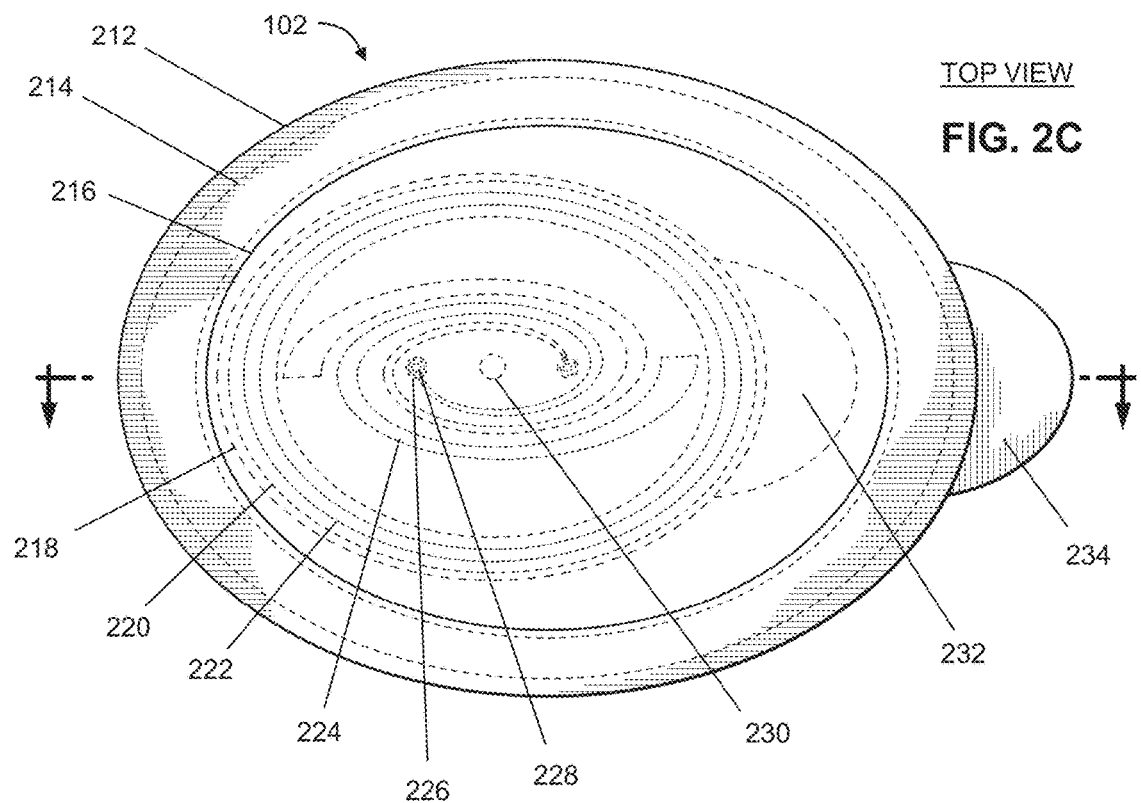
TOP VIEW
FIG. 2C
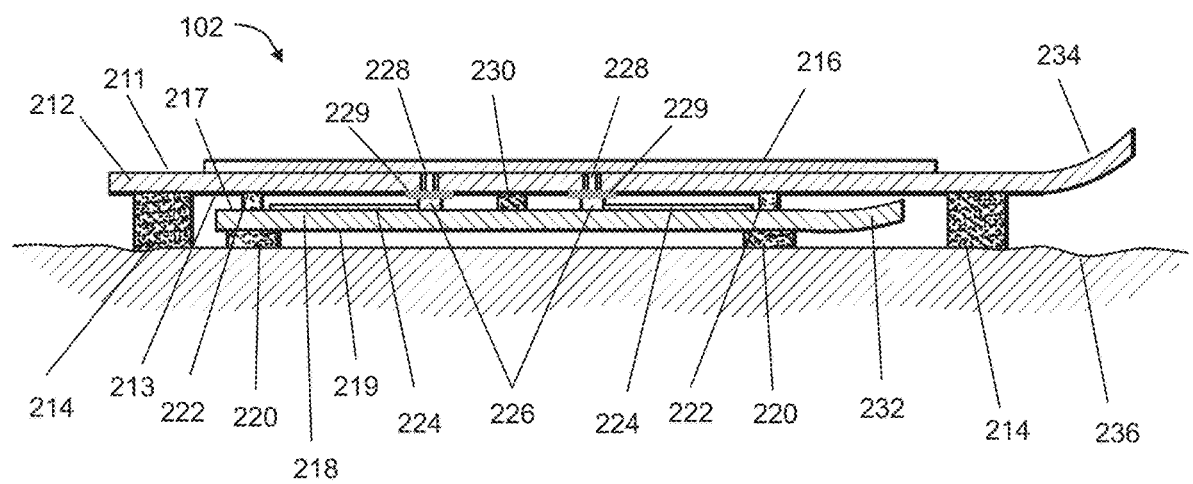
FIG. 2D  SIDE VIEW

224

240

250

METHOD AND APPARATUS FOR DELIVERING A SUBSTANCE TO AN INDIVIDUAL

FIELD OF THE DISCLOSURE

The subject disclosure relates to a method and apparatus for delivering substances that affect a biological condition of an individual.

BACKGROUND

Biological sensors can be used for measuring temperature, respiration, pulse rate, blood pressure, among other things. Some biological sensors can be implanted and can be configured to be battery-less. Battery-less sensors can utilize one or more antennas to receive radio frequency signals, and which can be converted to energy that powers components of the sensor while the radio frequency signals are present. Some biological sensors can also be configured to deliver dosages of a controlled substance.

BRIEF DESCRIPTION OF THE DRAWINGS

Reference will now be made to the accompanying drawings, which are not necessarily drawn to scale, and wherein:

FIGS. 2C-2D are block diagrams illustrating example, non-limiting embodiments of a top view and side view of a biological sensor in accordance with various aspects of the subject disclosure described herein;

DETAILED DESCRIPTION

The subject disclosure describes, among other things, illustrative embodiments for managing sensor data and usage of sensors generating the sensor data. Other embodiments are described in the subject disclosure.

One or more aspects of the subject disclosure include a machine-readable storage medium, including executable instructions that, when executed by a processor, facilitate performance of operations. The operations can include detecting an input signal by a sensing device coupled to a body part of an individual, the input signal not being associated with a biological measurement of the individual. The operations can also include determining from the input signal whether to deliver to the body part of the individual a dosage of a substance stored in a microfluidic system of the sensing device, and whether delivering the dosage satisfies a dosage policy. Responsive to determining from the input signal that delivery of the dosage of the substance is needed and satisfies the dosage policy, the operations can further include initiating, by the microfluidic system, delivery of the dosage of the substance to the body part of the individual, obtaining, by the sensing device, sensing data associated with a biological measurement of the individual, and determining from the biological measurement whether the dosage has improved a biological condition of the individual adjustable by the dosage.

One or more aspects of the subject disclosure include a method for detecting, by a substance delivery system coupled to a body part of an individual, an input signal not associated with a biological measurement of the individual, determining from the input signal, by the substance delivery system, whether delivering a dosage of a substance stored in the substance delivery system is needed and conforms to a dosage policy, and responsive to determining from the input signal that delivery of the dosage of the substance is needed and whether the dosage conforms to the dosage policy, initiating, by the substance delivery system, delivery of the dosage of the substance to the body part of the individual.

One or more aspects of the subject disclosure include a system having a processor, and memory that stores executable instructions that, when executed by the processor, facilitate performance of operations. The operations can include receiving a signal from a device coupled to a body part of an individual, wherein the signal is not associated with a biological state of the individual, determining from the signal whether delivering a dosage of a substance stored in the device is needed and whether the dosage exceeds a dosage threshold, and responsive to determining from the signal that delivery of the dosage of the substance does not exceed the dosage threshold, directing the device to initiate delivery of the dosage of the substance to the body part of the individual.

Figure 1:
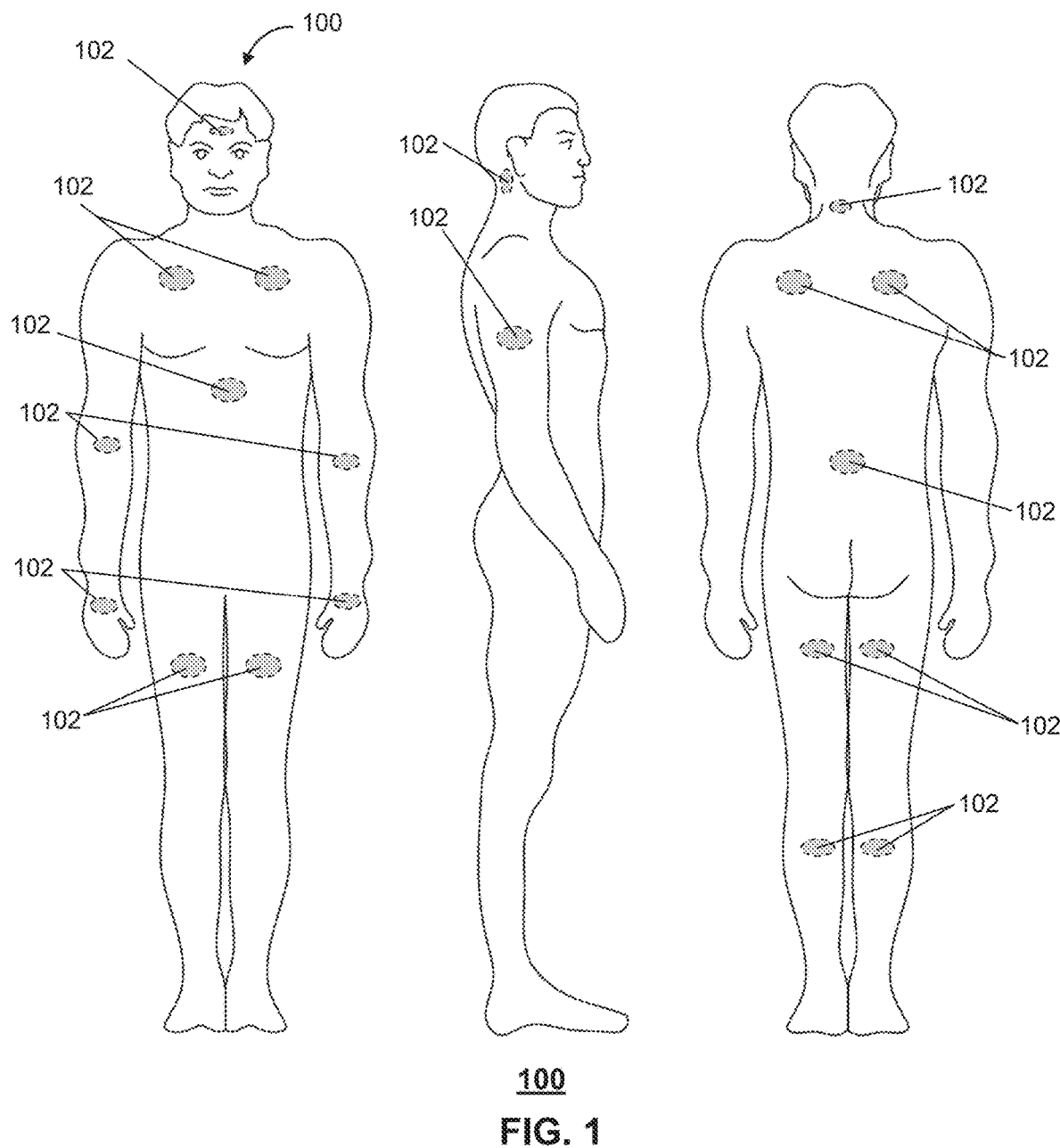
FIG. 1 is a block diagram illustrating example, non-limiting embodiments for placing sensors on a patient in accordance with various aspects of the subject disclosure described herein.

Turning now to FIG. 1, a block diagram illustrating example, non-limiting embodiments for placing biological sensors 102 on a patient 100 in accordance with various aspects of the subject disclosure is shown. FIG. 1 depicts a number of non-limiting illustrations of locations where biological sensors 102 can be placed on a patient 100. For example, biological sensors 102 can be placed on a patient's forehead, chest, abdomen, arms, hands, front or rear section of a thigh, behind an ear, on a side of an arm, neck, back, or calves as illustrated in FIG. 1. Other locations for placement of biological sensors 102 are possible and contemplated by the subject disclosure.

Figure 2A:
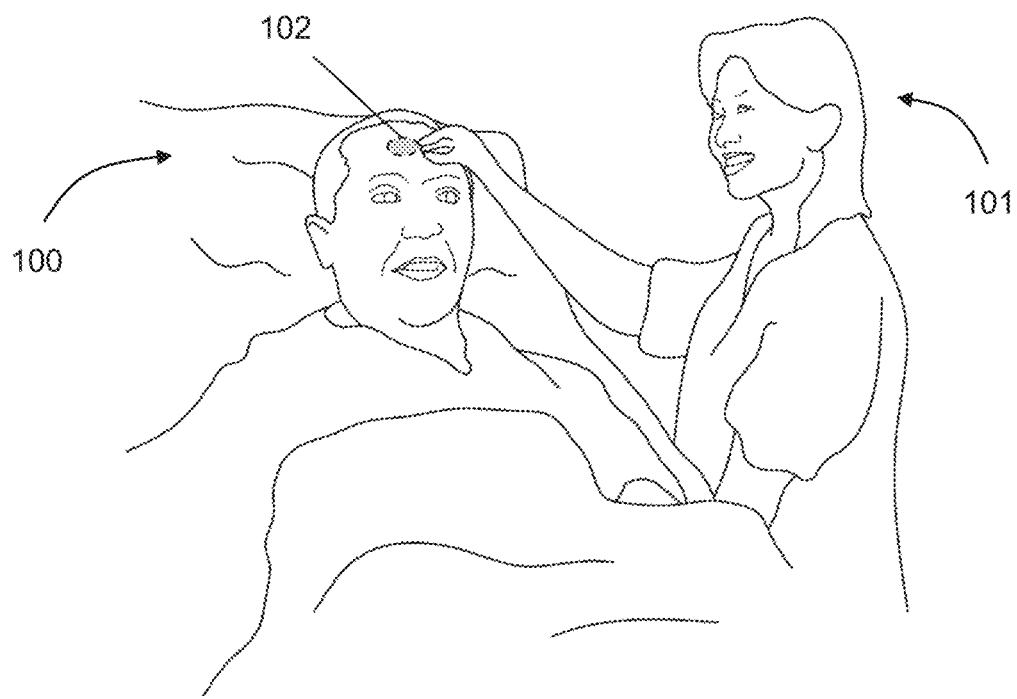
FIGS. 2A-2B are block diagrams illustrating example, non-limiting embodiments for managing use of one or more sensors of a patient in accordance with various aspects of the subject disclosure described herein.
Figure 2B:
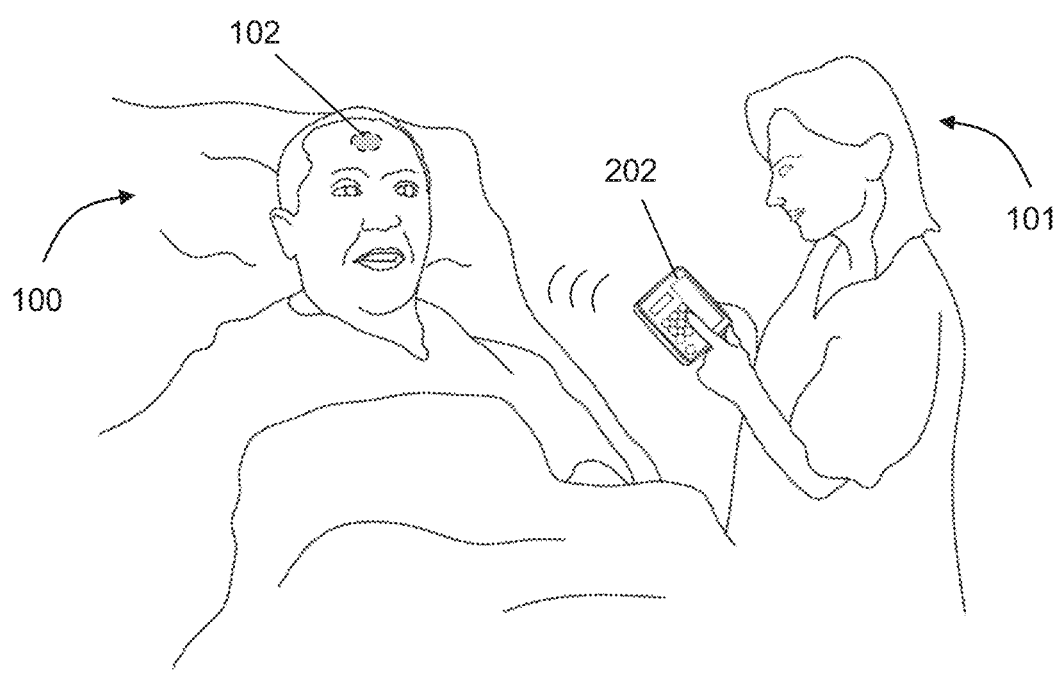

The biological sensors 102 can be placed or managed by a nurse 101 as shown in FIGS. 2A-2B. A nurse 101 can, for example, place a biological sensor 102 on the patient 100 as depicted in FIG. 2A and manage use of the biological sensor 102 with a computing device 202 such as a touch-screen tablet as depicted in FIG. 2B. The computing device 202 can also be represented by a smartphone, a laptop computer, or other suitable computing devices. The computing device 202 can be communicatively coupled to the biological sensor 102 by a wireless interface, such as, near field communications (NFC) having, for example, a range of 1-12 inches from the biological sensor 102, Bluetooth®, ZigBee®, WiFi, or other suitable short range wireless technology. Alternatively, the computing device 202 can be communicatively coupled to the biological sensor 102 by a wired interface or tethered interface (e.g., a USB cable).

Biological sensors 102 can be placed on an outer surface of a skin of the patient 100 with an adhesive, or can be implanted in the patient 100. Although the patient 100 is shown to be a human patient, a patient 100 can also be represented by a non-human species (e.g., a dog, a cat, a horse, cattle, a tiger, etc.) or any other type of biological organism which can use a biological sensor 102. Biological sensors 102 can be used for a number of functions such as, for example, electrocardiogram measurements, measuring temperature, perspiration, pulse rate, blood pressure, respiration rate, glucose levels in blood, peripheral capillary oxygen saturation (SpO2), and other measurable biological functions contemplated by the subject disclosure.

The biological sensors 102 can also be adapted to store measurements, compare measurements to biological markers to detect a biological condition, and to report such measurements and detected conditions. Biological sensors 102 are, however, not limited to monitoring applications. For example, biological sensors 102 can also be adapted to deliver controlled dosages of medication using, for example, micro-needles. Such sensors can also perform measurements to monitor a biological response by the patient 100 to the medication delivered, record and report measurements, frequency of dosages, amount of dosage delivered, and so on. The reports can also include temporal data such as day, month, year, time when measurement was performed and/or time when medication was delivered.

Now turning to FIGS. 2C-2D, block diagrams illustrating example, non-limiting embodiments of a top view and side view of a biological sensor 102 in accordance with various aspects of the subject disclosure described herein are shown. FIG. 2C illustrates a non-limiting embodiment of a top view of the biological sensor 102. FIG. 2D illustrates a non-limiting embodiment of a side view of the biological sensor 102 that supplements the illustrations of FIG. 2C. The biological sensor 102 can comprise a circuit 216 disposed on a top surface 211 of a first substrate 212. The circuit 216 and the first substrate 212 can comprise a single layer or multilayer flexible printed circuit board that electrically interconnects circuit components (not shown) of the circuit 216 using conductive traces and vias on a flexible substrate such as a polyimide substrate or other suitable flexible substrate technology. It will be appreciated that electrical components of the circuit 216 can also be disposed on a bottom surface 213 of the biological sensor 102.

Figure 2E:
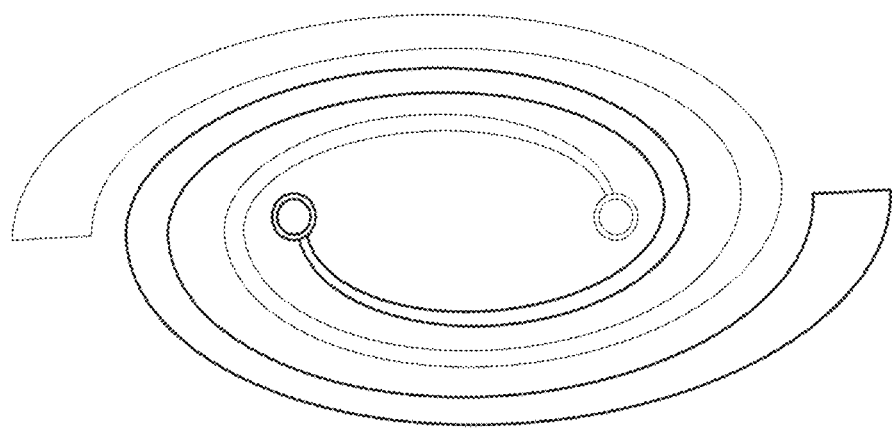
FIG. 2E is a block diagram illustrating an example, non-limiting embodiment of a removable component of a biological sensor in accordance with various aspects of the subject disclosure described herein.

The biological sensor 102 can further comprise a second substrate 218 that adhesively couples to a bottom surface 213 of the first substrate 212. In one embodiment, an adhesive layer 222 can be positioned near an outer edge of the second substrate 218. The adhesive layer 222 can be used to bind the second substrate 218 to the bottom surface 213 of the first substrate 212. One or more components of the biological sensor 102 can be disposed on a top surface 217 or bottom surface 219 of the second substrate 218. For example, an antenna 224 of the biological sensor 102 such as shown in FIG. 2E (shown also with ghosted lines in FIG. 2C) can be disposed on the top surface 217 of the second substrate 218. The antenna 224 can be used for wireless communications between the biological sensor 102 and other communication devices. Other components of the biological sensor 102 can be disposed on the second substrate 218 in place of or in combination with the antenna 224. For example, a transmitter, a power supply system, and/or a processor can be disposed on the top surface 217 or bottom surface 219 in place of or in combination with the antenna 224. The second substrate 218 and the antenna 224 disposed thereon can also be constructed using flexible printed circuit board technology similar to or identical to the flexible printed circuit board technology used for constructing the first substrate 212 and circuit 216 disposed thereon.

To enable electrical connectivity between the antenna 224 and the circuit 216, a conductive material 226 can be disposed on first and second feed points of the antenna 224. The conductive material 226 (such as a metal contact) can be configured to make contact with first and second conductive pads 229 disposed on the bottom surface 213 of the first substrate 212. The first and second conductive pads 229 can be electrically connected to first and second conductive vias 228. The combination of the first and second conductive pads 229 and the first and second conductive vias 228 provide the first and second feed points of the antenna 224 electrical conductivity to one or more circuit components (e.g., transmitter and receiver) included in the circuit 216. In an embodiment, the conductive material 226 of the first and second feed points can be configured so that it does not permanently adhered to the conductive pads 229 with solder or some other material with adherence properties.

To achieve electrical contact, an adhesive material 230 can be used at a center point (or at one or more other locations) of the second substrate 218 to cause the conductive material 226 to make electrical contact with the first and second conductive pads 229 by pressure (without adhesion). An adhesive layer 222 can also be used to maintain a stable position between the second substrate 218 and the first substrate 212 to avoid misaligning the conductive material 226 from the first and second conductive pads 229. The adhesive interconnectivity between the first and second substrates 212 and 218, respectively, provides an initial configuration in which the biological sensor 102 is in the form of a single unit prior to being placed on a skin surface 236 of a patient 100.

The biological sensor 102 can further comprise an adhesive layer 214 disposed on the bottom surface 213 of the first substrate 212 that surrounds an outer edge of the first substrate 212. Similarly, an adhesive layer 220 can be disposed on the bottom surface 219 of the first substrate 212 that surrounds an outer edge of the second substrate 218. Prior to placing the biological sensor 102 on a patient 100, a removable cover (not shown) can be coupled to the adhesive layers 214 and 220 to prevent exposing the adhesive layers 214 and 220 while the biological sensor 102 is in storage. The removable cover can be structurally configured with a smooth surface that reduces adherence to the adhesive layers 214 and 220, and thereby prevents damaging the adhesive properties of the adhesive layers 214 and 220 when the cover is removed. The removable cover can be further configured to extend outwardly from the adhesive layer 214 or it can include selectable tab to enable ease of removal of the cover from the biological sensor 102 in preparation for its use. The biological sensor 102 with an attached removable cover can be placed in a sealed package for storage purposes. In anticipation of the discussions that follow, it will be appreciated that the biological sensor 102 can include some or all of the components illustrated in FIG. 4, and can perform the operations described below.

Figure 2F:
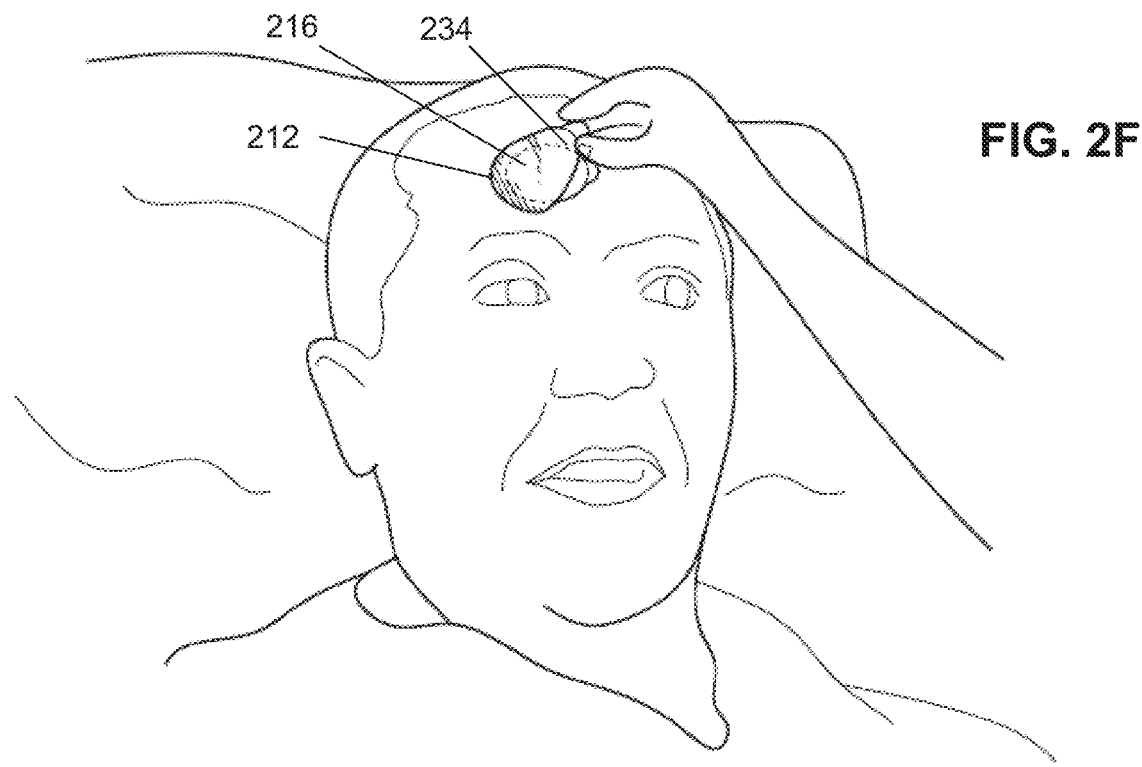
FIGS. 2F-2I are block diagrams illustrating example, non-limiting embodiments for removing and decommissioning a biological sensor in accordance with various aspects of the subject disclosure described herein.
Figure 2G:
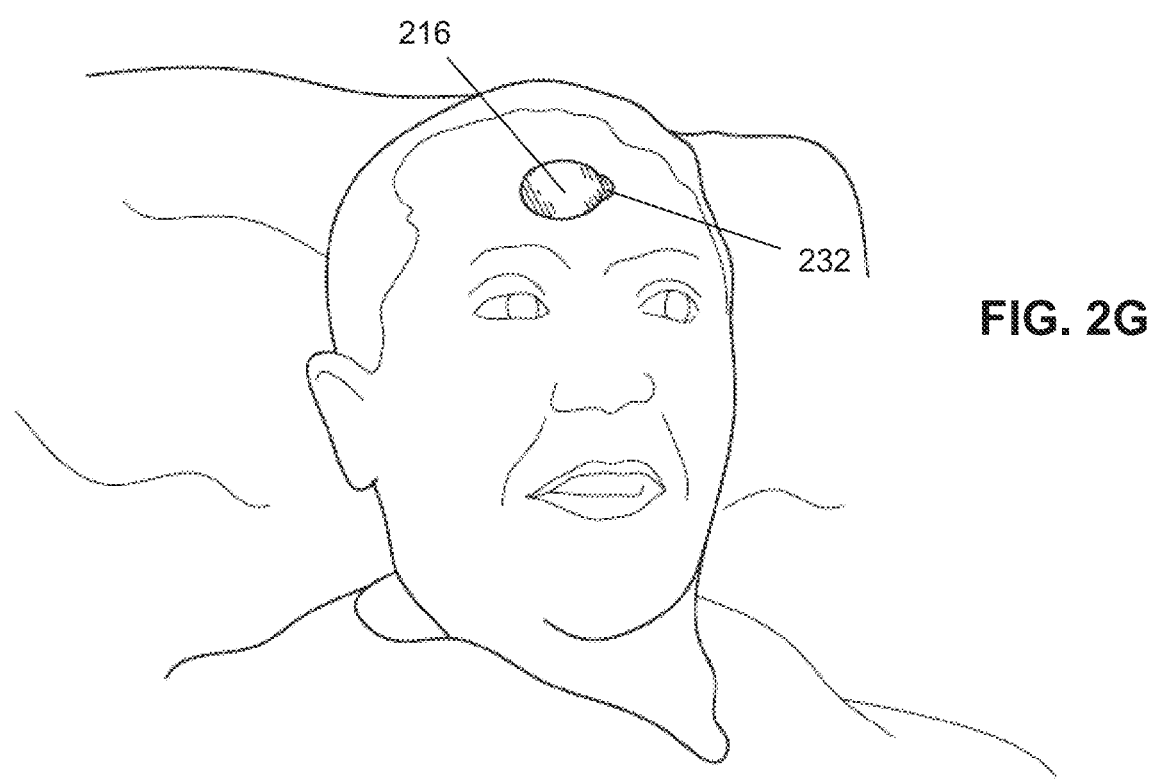
Figure 2H:
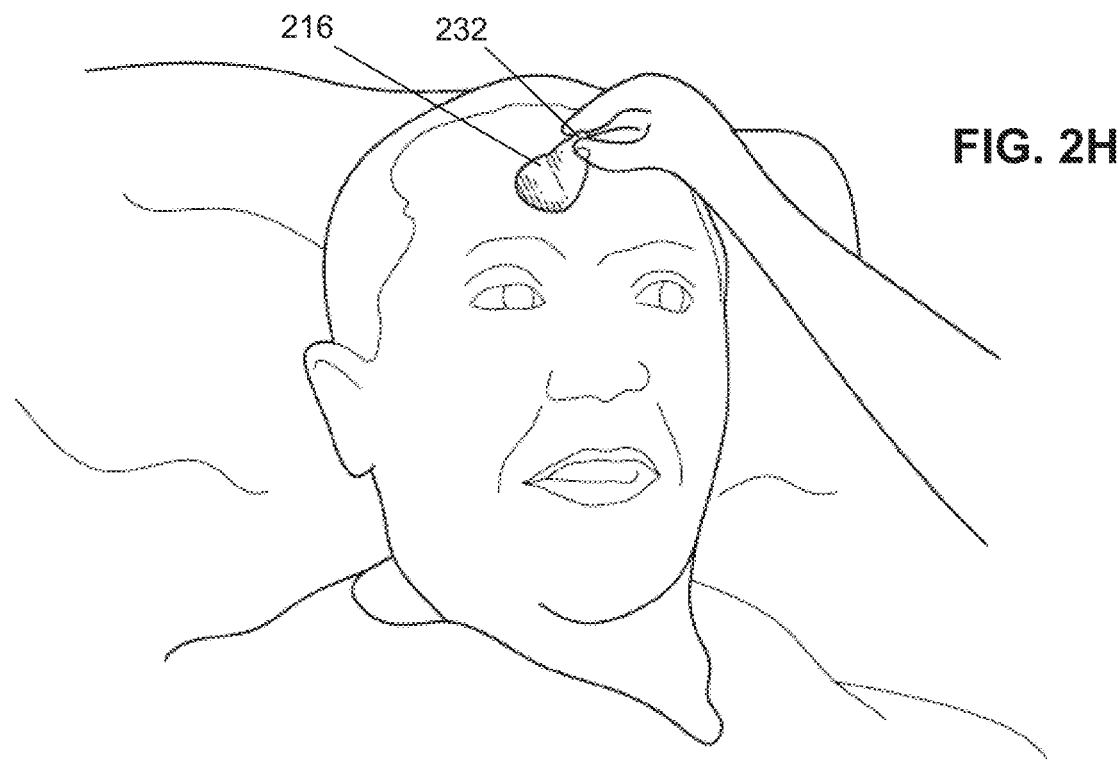
Figure 2I:
Figure 2J:
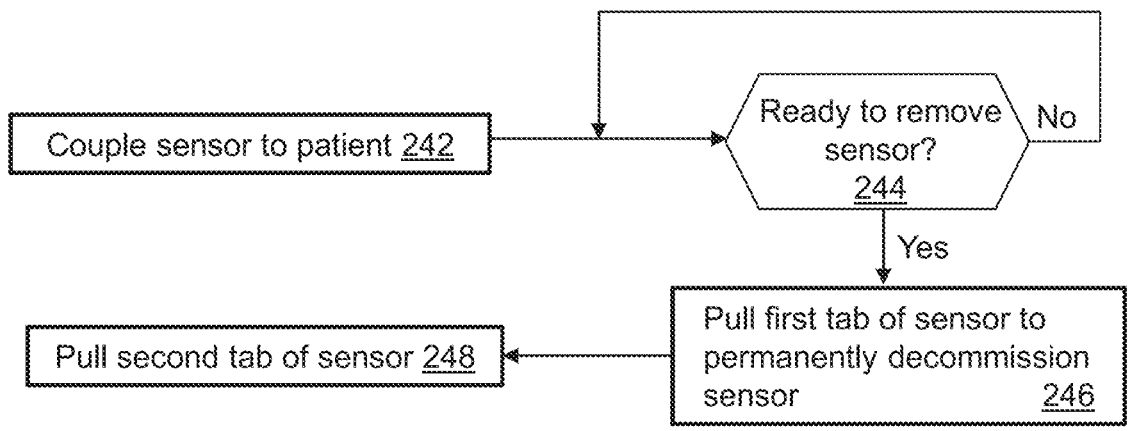
FIG. 2J is a block diagram illustrating an example, non-limiting embodiment of a method for decommissioning a biological sensor in accordance with various aspects of the subject disclosure described herein.

Now turning to FIG. 2J, a block diagram illustrating an example, non-limiting embodiment of a method 240 for decommissioning the biological sensor 102 of FIGS. 2C-2D in accordance with various aspects of the subject disclosure described herein is shown. Method 240 will be described in view of FIGS. 2F-2I. Method 240 can begin with step 242 whereby a biological sensor 102 is placed on a patient 100 as shown in FIGS. 2A-2B. When a clinician (such as a nurse 101) is prepared to utilize the biological sensor 102, the sealed package holding the biological sensor 102 can be manually torn, and the cover can be removed thereby exposing adhesive layers 214 and 220. The clinician can then place the biological sensor 102 on the skin 236 of the patient 100. Upon doing so, the skin 236 of the patient 100 adheres to the adhesive layer 214 of the first substrate 212 and the adhesive layer 220 of the second substrate 218.

At a later time (e.g., minutes, hours, days or weeks later), the clinician can determine at step 244 whether it is time to remove the biological sensor 102. The first substrate 212 can comprise a tab 234 that does not adhere to the skin 236. At step 246, the tab 234 can be selected and pulled by the clinician to remove the biological sensor 102 when the clinician deems at step 244 that the biological sensor 102 is no longer to be used. The adhesive layers 222 and 220 can be configured so that the adhesive force between the bottom surface 213 of the first substrate 212 and the top surface 217 of the second substrate 218 is substantially weaker than the adhesive force between the skin 236 and the bottom surface 219 of the second substrate 218.

A disparity in bonding forces can be accomplished by configuring the adhesive layer 220 so that it is wider than the adhesive layer 222 (e.g., 2:1) and/or by utilizing an adhesive material for the adhesive layer 220 that has a substantially stronger bonding force than a bonding force created by the adhesive material of the adhesive layer 222. Consequently, when the clinician pulls tab 234 with sufficient force, the bond between the second substrate 218 and the first substrate 212 breaks enabling removal of the first substrate 212 from the second substrate 218, while the second substrate 218 remains bonded to the skin 236 of the patient 100 as shown in FIGS. 2F-2G.

By separating the first substrate 212 from the second substrate 218, the biological sensor 102 is permanently decommissioned since the biological sensor 102 can no longer transmit wireless signals to other communication devices as a result of the antenna 224 (that remains on the second substrate 218) no longer making electrical contact with the circuit 216 of the first substrate 212. To complete the removal process of the biological sensor 102, the clinician can pull tab 232 of the second substrate 218 at step 248, which is also not bonded to the skin 236, thereby removing the remaining portion of the biological sensor 102 as shown in FIGS. 2H-2I. According to FIGS. 2F-2I the biological sensor 102 can be decommissioned by a clinician in a two-step approach.

It will be appreciated that the biological sensor 102, illustrated in FIGS. 2C-2D, can be modified or otherwise adapted with other embodiments that enable decommissioning of the biological sensor 102 in a manner similar to the steps illustrated in FIGS. 2F-2I. For example, the conductive materials 226 of the antenna 224 can be weakly bonded to conductive pads 229 with solder instead of relying on pressure contact. In this embodiment, the adhesive material 230 may no longer be required. The adhesive layer 220 can be configured to adhere to the skin 236 of the patient 100 such that it exceeds a force to break the solder joint between the conductive materials 226 and the conductive pads 229.

In yet another embodiment, the second substrate 218 can include a component that inductively couples to the circuit 216 of the first substrate 212. In this embodiment, electrical physical contact between the component and the circuit 216 is not required. If the component in the second substrate 218 is required to maintain operations of the biological sensor 102, then the biological sensor 102 will be decommissioned when the first substrate 212 of the biological sensor 102 is removed from the patient 100 (as illustrated in FIGS. 2F-2G), which in turn removes the inductive coupling between the circuit 216 of the first substrate 212 and the component of the second substrate 218. It will be appreciated that any circuit component required to operate the biological sensor 102 can be disposed on the second substrate 218 for purposes of decommissioning the biological sensor 102 when it is removed from the patient 100 as shown in FIGS. 2F-2I.

The subject disclosure therefore contemplates modifications to the foregoing embodiments of the biological sensor 102 that enables removal, damage or other form of modification to one or more components of the biological sensor 102, which can serve to decommission the biological sensor 102 when a clinician removes the biological sensor 102 from the skin 236 of a patient 100. Such a decommissioning process can help prevent inadvertent reuse, overuse or misuse of the biological sensor 102.

Figure 2K:
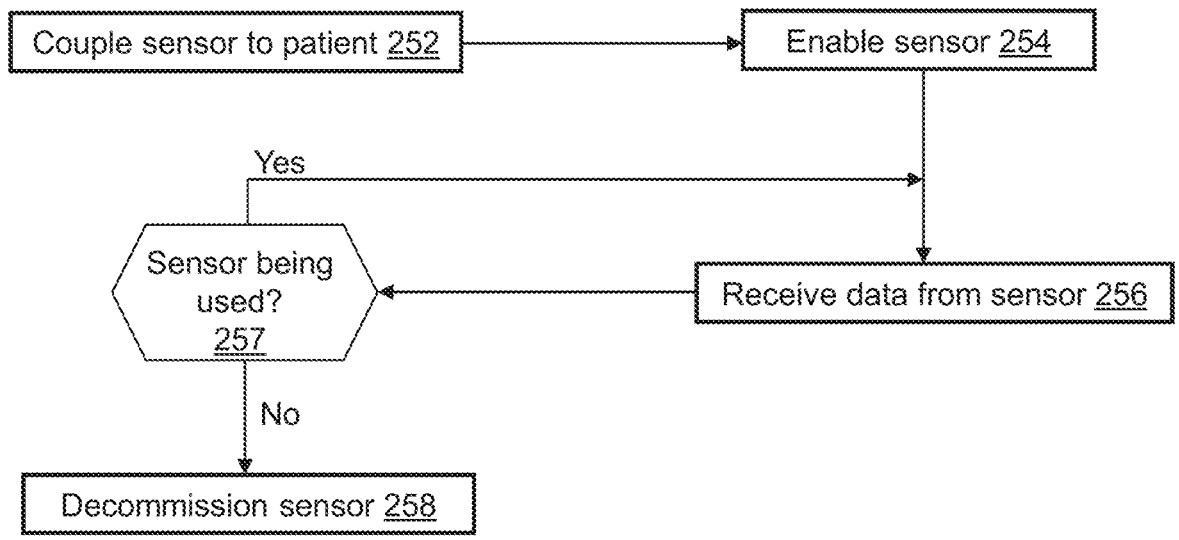
FIG. 2K is a block diagram illustrating an example, non-limiting embodiment of a method for decommissioning a biological sensor in accordance with various aspects of the subject disclosure described herein.

Now turning to FIG. 2K, a block diagram illustrating an example, non-limiting embodiment of a method 250 for decommissioning a biological sensor 102 in accordance with various aspects of the subject disclosure described herein is shown. Method 250 can be used as an alternative embodiment to method 240. Particularly, method 250 can be used in instances where physical removal of the biological sensor 102 from the skin 236 of patient 100 does not result in a decommissioning of the biological sensor 102. With this in mind, method 250 can begin at step 252 where a clinician places a biological sensor 102 on a patient 100 as shown in FIGS. 2A-2B. The clinician can enable the biological sensor 102 at step 254 utilizing the computing device 202 shown in FIG. 2B, a sensor management system 304 shown in FIG. 3A, or other sensor management techniques, which are described below in accordance with the flowchart illustrated in FIG. 6. For illustration purposes only, it will be assumed that the biological sensor 102 is being managed by the computing device 202 and/or the sensor management system 304. Other embodiments are disclosed.

Once the biological sensor 102 is enabled, the computing device 202 or sensor management system 304 can receive data from the biological sensor 102. At step 257, the computing device 202 or sensor management system 304 can be configured to determine from the data whether the biological sensor 102 is no longer in use. For example, the data received from the biological sensor 102 can be motion sensor data generated by a motion sensor 418 shown in FIG. 4 described below. Motion sensor data can indicate that the biological sensor has been stationary for a period of time (e.g., 1 hour or more) which may indicate that the biological sensor 102 is no longer being used by the patient 100.

The data can further include biological sensor data such as the patient's pulse rate, blood pressure, temperature, and/or other biological sensing data generated by one or more sensors 410 of the biological sensor 102 (shown in FIG. 4 and described below). If, for example, the biological sensor data is devoid of biological sensor readings (e.g., no pulse or blood pressure), a determination can be made that the biological sensor 102 is no longer in use. Similarly, if biological sensor data does not correspond to an expected range of the patient 100 (e.g., temperature reading received is room temperature as opposed to body temperature), then similarly a determination can be made that the biological sensor 102 is no longer in use. The computing device 202 or sensor management system 304 can analyze a single aspect or a combination aspects of the data it receives at step 256 to make a determination at step 257 whether the biological sensor 102 is in use.

If a determination is made that the biological sensor 102 continues to be in use by the patient 100, the computing device 202 or sensor management system 304 can proceed to step 256 to continue monitoring data it receives from the biological sensor 102. If, on the other hand, a determination is made that the biological sensor 102 is no longer in use, the computing device 202 or sensor management system 304 can proceed to step 258 and decommission the biological sensor 102. The computing device 202 or sensor management system 304 can accomplish this step in several ways.

In one embodiment, the computing device 202 or sensor management system 304 can send wireless instructions to the biological sensor 102 to disable communications permanently. Upon receiving such instructions, the biological sensor 102 can permanently disable a transmitter of the biological sensor 102 by, for example, opening a switch that connects an antenna to the transmitter. The switch can be an electromechanical device designed to remain open after it is switched to an open position thereby permanently disabling communications by the biological sensor 102. Alternatively, the biological sensor 102 can be configured to store information in a nonvolatile memory which informs the biological sensor 102 that communications (or operations in general) are to be permanently disabled. The nonvolatile memory can be configured such that once the information is written into memory it cannot be removed/erased from the memory. In yet another embodiment, the computing device 202 or sensor management system 304 can be configured to permanently decommission the biological sensor 102 by discontinuing communications with the biological sensor 102 and/or ignoring messages transmitted by the biological sensor 102. In one embodiment, the decision by the computing device 202 or sensor management system 304 to stop communication (or ignore communications by the biological sensor 102) can be associated with a unique identification number that is associated with the biological sensor 102. In another embodiment, the computing device 202 or sensor management system 304 can be configured to stop communication (or ignore communications) with one or more biological sensor 102 associated with a patient in response to the patient being discharged. The computing device 202 or sensor management system 304 can be integrated or communicatively coupled to a patient discharge system to detect when a patient is discharged.

It will be appreciated that method 250 can be adapted so that the biological sensor 102 can be configured to perform steps 257 and 258 independent of the computing device 202 or sensor management system 304. For example, the biological sensor 102 can be configured to decommission itself if after a certain period (e.g., 1 hour) it has not detected motion, a pulse or other biological sensor readings. Method 250 can also be adapted so that steps 256-258 can be performed by an ancillary device such as a trash dispenser. For example, a trash dispenser can be configured with a communication device enabled to receive data from the biological sensor 102, analyze the data at step 257 and decommission the biological sensor 102 at step 258 as previously described. The trash dispenser can also be configured to transmit a message to the computing device 202 or sensor management system 304, the message providing an identification (e.g., patient ID, or other unique identifier) of the biological sensor 102, and indicating that the biological sensor 102 has been decommissioned. The computing device 202 or sensor management system 304 can use this information to record the decommissioning of the biological sensor 102.

While for purposes of simplicity of explanation, the respective processes are shown and described as a series of blocks in FIGS. 2J-2K, it is to be understood and appreciated that the claimed subject matter is not limited by the order of the blocks, as some blocks may occur in different orders and/or concurrently with other blocks from what is depicted and described herein. Moreover, not all illustrated blocks may be required to implement the methods described herein.

Figure 2L:
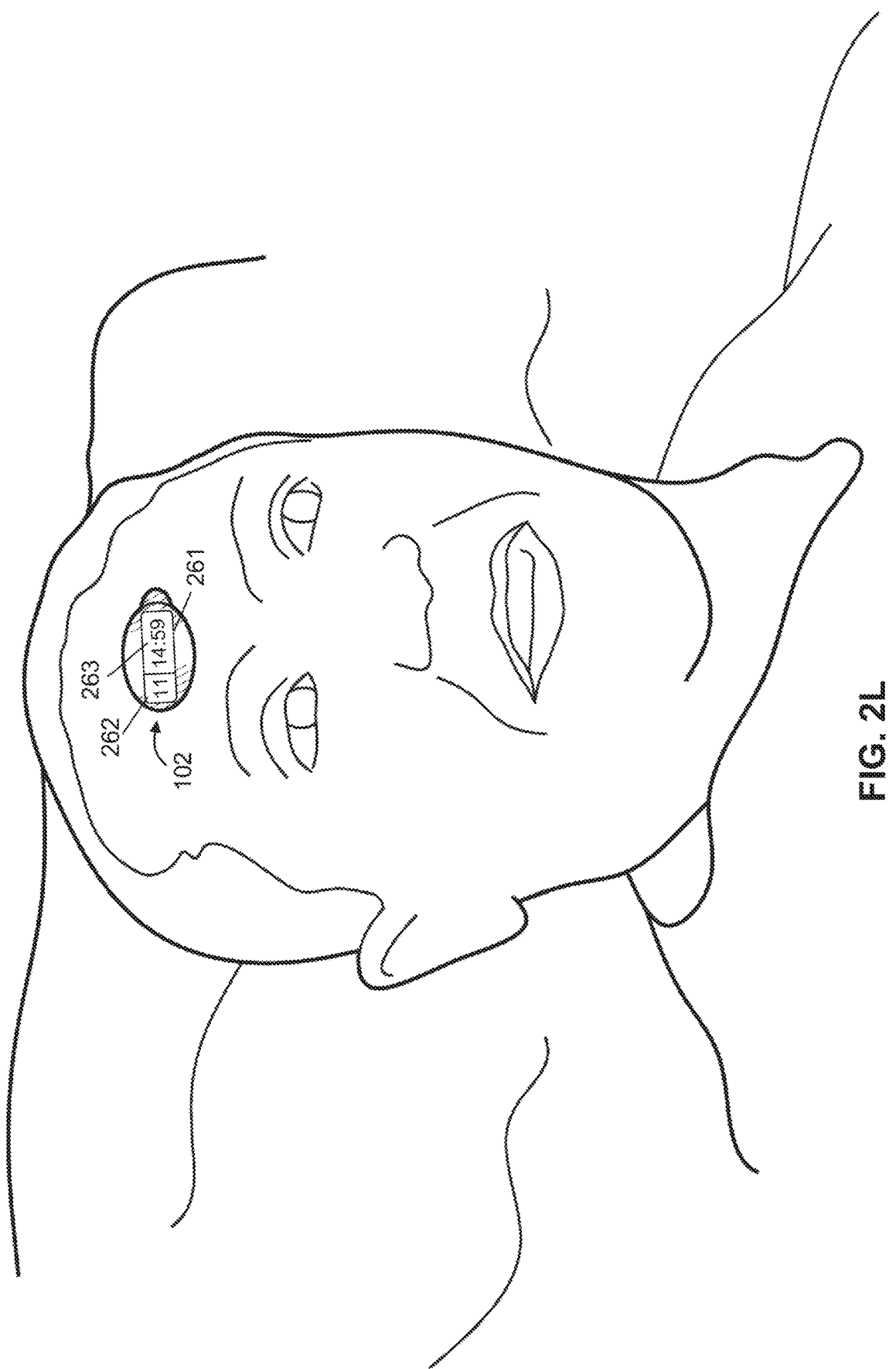
FIG. 2L is a block diagram illustrating an example, non-limiting embodiment of a biological sensor in accordance with various aspects of the subject disclosure described herein.

Now turning to FIG. 2L, a block diagram illustrating an example, non-limiting embodiment of a biological sensor 102 in accordance with various aspects of the subject disclosure is shown. The biological sensor 102 can comprise a display 261 (e.g., LCD, OLED or other low power display technology—see FIG. 5) for presenting information. The biological sensor 102 can also be configured with a timer to present a timed event. The timer can be used for presenting an elapsed time 263. In one embodiment, the elapsed time 263 can be based on a countdown sequence that counts down to zero. Countdown sequences can be useful in situations where a procedure is expected to be performed within a certain period. In another embodiment, the timer can be configured to count upwards to indicate to a clinician 101 how much time has transpired since the timed event was initiated.

In some embodiments, the timed event can represent a timed procedure that needs to be initiated by a clinician 101 or another individual (e.g., a patient 100 wearing the biological sensor 102). The type of procedure to be initiated can be identified by an indicator such as a procedural code 262 that is recognizable by the clinician 101 or the patient 100. In one embodiment, the timed procedure can be triggered by a biological condition detected by the biological sensor 102. In another embodiment, the timed procedure can be triggered by a procedure initiated by a clinician 101 via a computing device 202 as illustrated in FIG. 2B or by the patient 100 with a mobile device (e.g., a smartphone, tablet or laptop). The computing device 202 (or other processing device) can be configured, for example, to transmit a wireless message directed to the biological sensor 102 that describes the procedure being initiated by the clinician 101 (or patient 100).

Figure 2M:
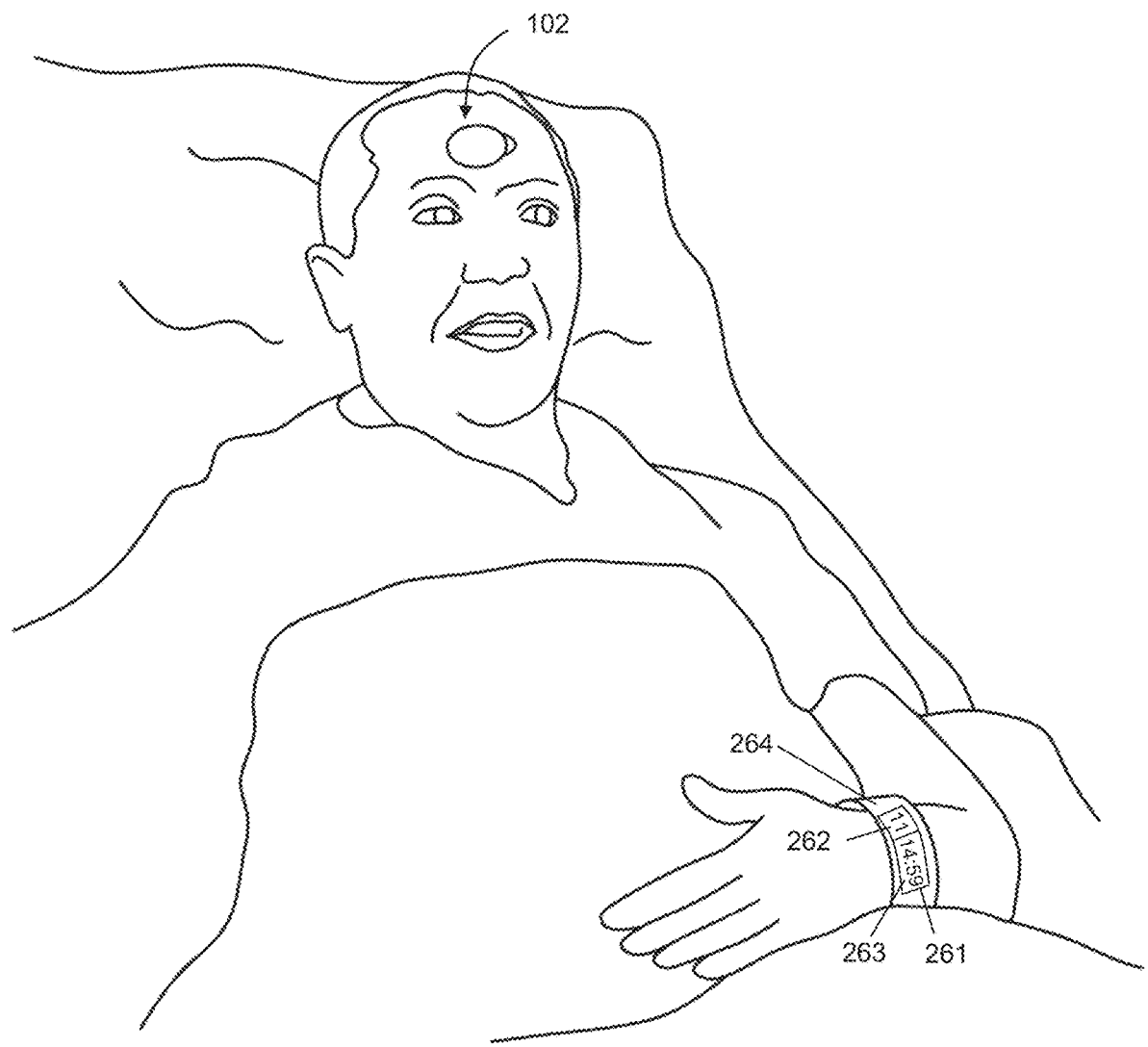
FIGS. 2M-2P are block diagrams illustrating example, non-limiting embodiments of devices communicatively coupled to a biological sensor in accordance with various aspects of the subject disclosure described herein.

Now turning to FIGS. 2M-2P, block diagrams illustrating example, non-limiting embodiments of devices communicatively coupled to a biological sensor 102 in accordance with various aspects of the subject disclosure are shown. FIG. 2M depicts a biological sensor 102 configured to transmit wireless signals to a device such as a wristband 264 attached to the patient 100. The biological sensor 102 can be configured, for example, to detect an event that triggers a timed event such as a timed procedure and/or timed treatment. The biological sensor 102 can transmit wireless signals to the wristband 264 to present the timed event. The biological sensor 102 can, for example, provide the wristband 264 information for presenting the procedural code 262 and elapsed time 263 since the time event was initiated. The wristband 264 can be battery operated and can include a display 261, a wireless receiver, and a processor to control the receiver and presentations at the display 261. The wristband 264 can further include a timer that can count down or count up to track time from when the timed event is initiated, thereby offloading the biological sensor 102 from providing timer information to the wristband 204.

Figure 2N:
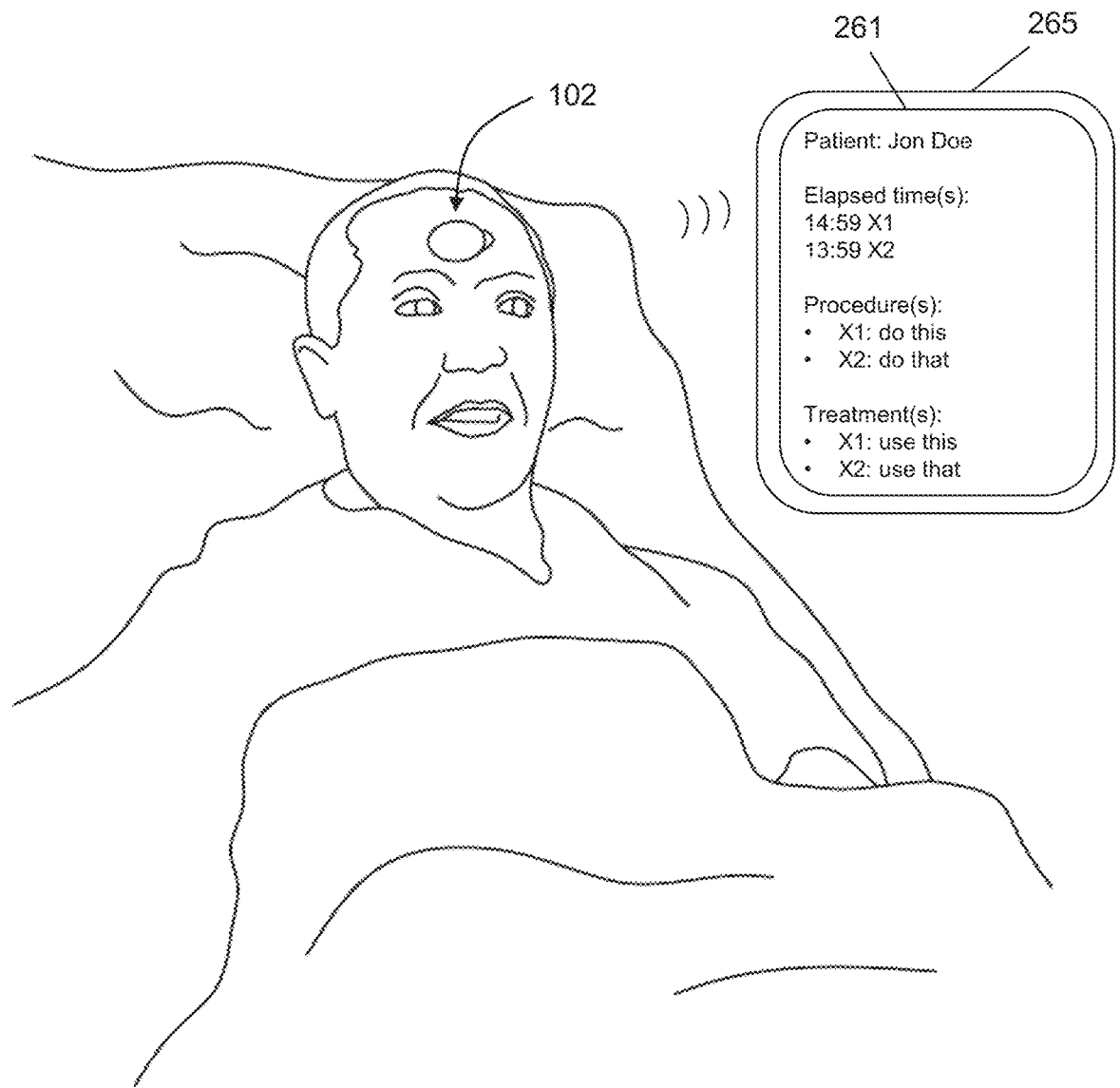

In another embodiment, the biological sensor 102 can be configured to wirelessly transmit information to a device 265 attached to a wall or other fixture (e.g., the headboard of a bed) as depicted in FIG. 2N. The device 265 can be equipped with a display 261, a wireless receiver and a processor that controls the receiver and the information presented at the display 261. The device 265 can also include a timer that can count down or count up to track time from when the timed event is initiated, thereby offloading the biological sensor 102 from providing timer information to the device 265. If the device 265 has a large enough display, the device 265 can be configured to present information about the patient 100 (e.g., patient's name), the elapsed time, one or more procedures that have been or are to be initiated, and one or more treatments associated with each procedure. In the event that more than one procedure is initiated, the device 265 can be further configured to present more than one elapsed time for each timed procedure.

Figure 2O:
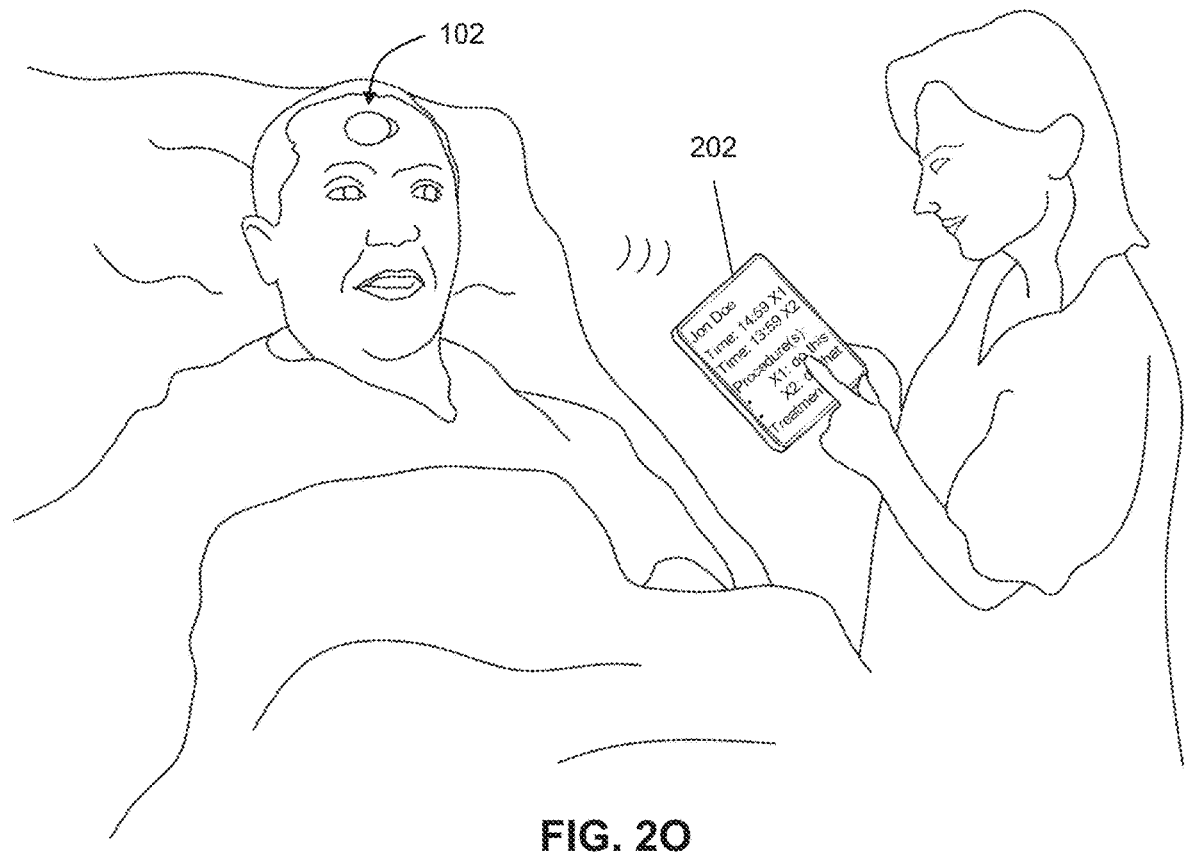
Figure 2P:
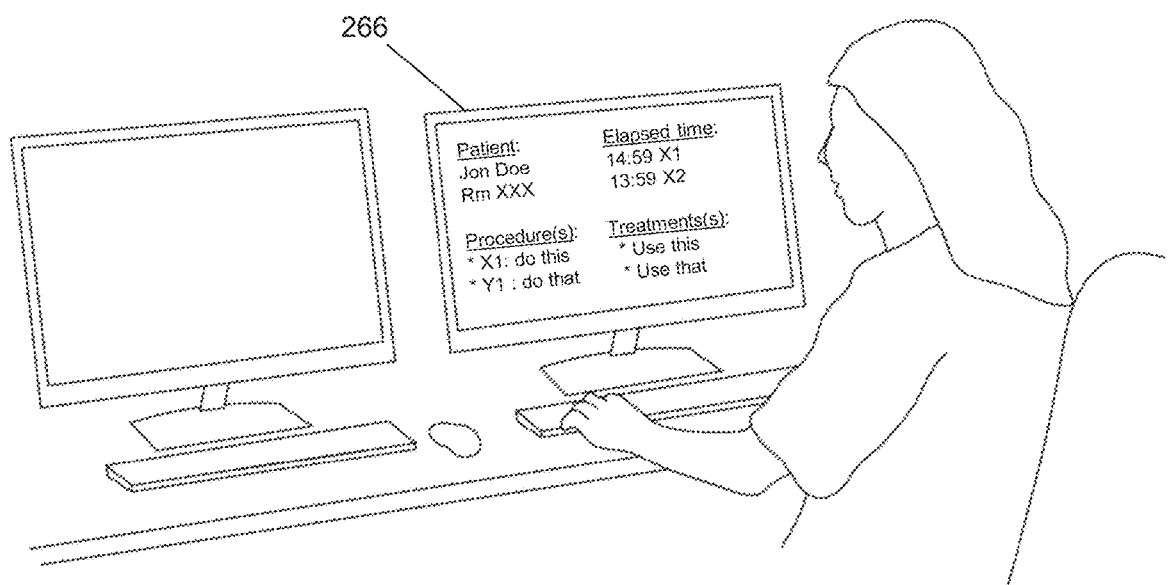

Alternatively, a clinician 101 can use a computing device 202 (such as a touch-screen tablet shown in FIG. 2O, also shown in FIG. 2B) to receive wireless information from the biological sensor 102 and present it in a manner similar to what was presented by device 265 in FIG. 2N. In yet another embodiment, the computing device 202 can be further configured to provide the information received from the biological sensor 102 to a system 266 as illustrated in FIG. 2P. Alternatively, the system 266 can be communicatively coupled to the biological sensor 102 by way of a wireless access point (e.g., Bluetooth® or WiFi), thereby enabling the biological sensor 102 to provide the system 266 information directly without an intermediate device such as the computing device 202. The system 266 can present information on a display in a manner similar to what was presented in FIGS. 2N-2O. In one embodiment, the system 266 can represent a local station accessible to multiple parties (e.g., nurses on a floor of a hospital). In other embodiments, the system 266 can be remote, and can be managed by remote personnel (or autonomously). In such embodiments, the system 266 can be represented by the sensor management system 304, which will be described below.

Figure 2Q:
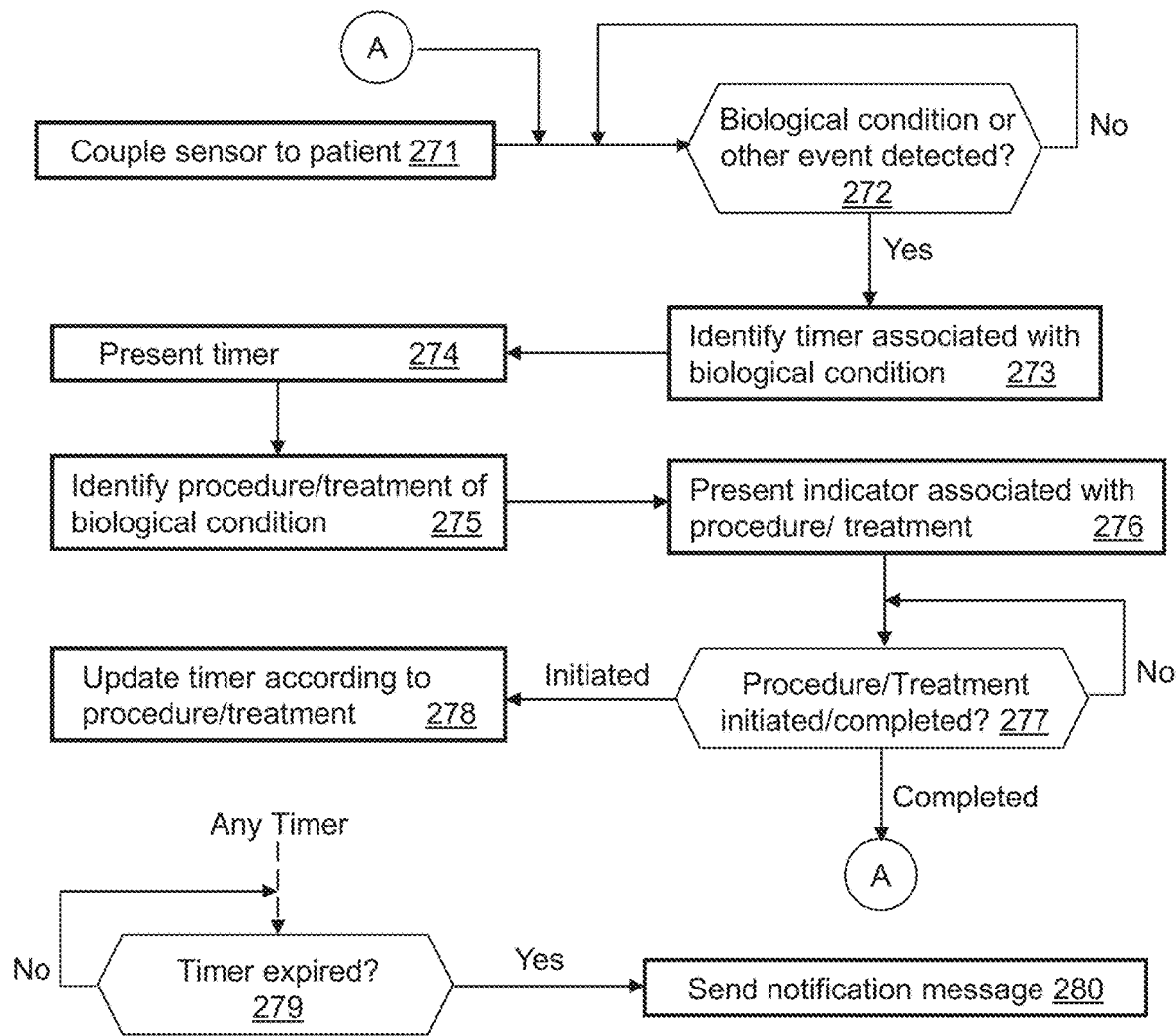
FIG. 2Q is a block diagram illustrating an example, non-limiting embodiment of a method for initiating a timed event, procedure, treatment and/or process in accordance with various aspects of the subject disclosure described herein.

Now turning to FIG. 2Q, a block diagram illustrating an example, non-limiting embodiment of a method 270 for initiating a timed event, procedure, treatment and/or process in accordance with various aspects of the subject disclosure is shown. Method 270 can begin at step 271 where a clinician 101 places a biological sensor 102 on a patient 100 as shown in FIG. 2A. It will be appreciated that the biological sensor 102 can be placed on any portion of the patient 100 (e.g., head, chest, leg, thigh, etc.) as shown by the illustrations of FIG. 1. The biological sensor 102 can be provisioned as described below by the flowchart of FIG. 6. Once provisioned, the biological sensor 102 can be configured to detect a biological condition (e.g., a fever, a heart attack, high blood pressure, high pulse rate, etc.). If the biological condition is detected at step 272, a timer can be identified at step 273 according to the biological condition detected.

In one embodiment, the biological sensor 102 can be configured with a look-up table stored in a memory device of the biological sensor 102. The look-up table can include timer values searchable by a corresponding biological condition. Once a biological condition is detected at step 272, the biological sensor 102 can be configured to locate at step 273 an entry in memory that matches the biological condition. The biological condition can be identified by a unique number generated by the biological sensor 102. The unique number used for identifying the biological condition can be used to search a memory for corresponding timer value(s), procedure(s), and/or treatment(s). The biological sensor 102 can be further configured to retrieve a timer value from the memory location matching the biological condition. The timer value can be used to configure a timer for a count down or count up sequence. Once the timer is configured, an elapsed time can be presented at a display of the biological sensor 102 at step 274 as shown in FIG. 2L. Alternatively, the biological sensor 102 can provide the timer value to another device such as the wristband 264 or the display device 265, each having its own display 261 and timer.

In other embodiments, the biological sensor 102 can be configured to transmit a message to a computing device 202 or the sensor management system 304 over a wired or wireless interface, the message indicating that a biological condition has been detected. The computing device 202 or the sensor management system 304 in turn can search a memory (or database) according to the detected biological condition (utilizing, for example, a unique code provided by the biological sensor), and thereby obtain a corresponding timer value to initiate a timed event. In one embodiment, the computing device 202 or the sensor management system 304 can provide the timer value to the biological sensor 102 over the wired or wireless interface for presenting an elapsed time at display 261 of the biological sensor 102, the wristband 264, or display device 265. In other embodiments, the computing device 202 can initiate a timer according to the timer value and present an elapsed time on a display of the computing device 202 as shown in FIG. 2O. Alternatively, or in combination, the computing device 202 or the sensor management system 304 can provide the timer value to a work station as shown in FIG. 2P for presentation of an elapsed time.

At step 275, one or more procedures and/or one or more treatments can also be identified based on the biological condition detected by the biological sensor 102. In one embodiment, step 275 can be performed by the biological sensor 102. The biological sensor 102 can, for example, retrieve one or more procedures and/or one or more treatments from a look-up table included in its memory which can be searched according to the unique code associated with the biological condition. Alternatively, the computing device 202 or the sensor management system 304 can search from its memory (database) one or more procedures and/or one or more treatments according to the biological condition provided by the biological sensor 102. The procedures can provide a clinician 101 a process for addressing the biological condition. The treatments can further instruct the clinician 101 to use certain medication, therapy, corrective measures, materials, and/or equipment. In some embodiments, the procedure(s) and/or treatment(s) can be presented at step 276 according to one or more numeric or alphanumeric indicators utilizing a small section of the display 261 shown in the embodiments of FIGS. 2L-2M. For larger displays, the procedure(s) and/or treatment(s) can be presented at step 276 more fully as illustrated in FIGS. 2O-2P.

At step 277, initiation or completion of a procedure and/or treatment can be monitored. In one embodiment, this step can be performed by the clinician 101 utilizing the computing device 202. For example, the clinician 101 can enter by way of a user interface of the computing device 202 (e.g., touchscreen or keyboard) an indication that one or more of the procedures have been initiated or completed. Upon detecting this input, the timer value used by the timer at step 274 can be updated at step 278. Step 278 may be useful in situations where a procedure has multiple timed sequences. An illustration is provided below to better understand how multiple timed sequences can occur.

Suppose, for example, the timer initiated at step 274 represents a timer which upon expiration at step 279 alerts a clinician at step 280 with a notification message. The notification message can be transmitted by the biological sensor 102, the wristband 264, the display device 265, the computing device 202 or the system 266 over a wired or wireless interface. The notification message can include information indicating what procedure(s) and/or treatment(s) to initiate. In this embodiment, the expiration of the timer constitutes a time when to initiate the procedure(s) and/or treatment(s). Alternatively, the timer initiated at step 274 can represent a timer that directs a clinician 101 not to exceed a time limit for initiating a procedure/treatment. In this embodiment the clinician can initiate a procedure/treatment anytime within an expiration period of the timer. If the timer expires, the notification message can represent a warning message indicating that initiating the procedure/treatment should not be delayed further.

Once the clinician 101 initiates the procedure, a new timer can be set at step 278. Step 278 can be invoked in situations where a procedure requires a sequence of steps or one or more subsequent procedures/treatments to mitigate a biological condition. Each step or procedure may have its own timed constraints. Hence, as a clinician 101 completes one step or procedure/treatment another timer is set at step 278 for the next step or procedure/treatment. A clinician can provide user input by way of the computing device 202 that indicates that start or end of a procedure/treatment. Once a procedure or treatment is completed, step 278 may no longer be necessary, and the process can be restarted at step 272.

It will be appreciated that steps 277-280 can be implemented by the biological sensor 102 independently or in cooperation with the computing device 202 or sensor management system 304. It is further appreciated that method 270 can be used for any number of detectable event. For example, when a biological sensor 102 is removed from the patient 100 as described above, the computing device 202 or sensor management system 304 can detect this event and initiate a timer at the displays illustrated in FIGS. 2N-2P to direct a clinician 101 to replace the biological sensor 102 with another biological sensor 102 within a given time period.

An event can also be generated by user input. For example, a clinician 101 can generate user input (audible or tactile) by way of the user interface of the computing device 202 to indicate that the patient 100 has experienced a biological condition (e.g., a heart attack). In another embodiment, monitoring equipment such as an ECG/EKG monitor can be configured to generate information that can identify an event (e.g., a heart attack, failed breathing, etc.). The user input and/or information generated by a biological monitor can be conveyed to a system (e.g., the sensor management system 304) that can identify a biological condition or event which in turn can cause an initiation of steps 272-280 as previously described. The steps of method 270 can be performed in whole or in part by biological sensor 102, the computing device 202, sensor management system 304, equipment monitoring biological functions, or any combinations thereof. Additionally, method 270 can also be adapted to detect at step 272 a change in a previously detected biological condition (e.g., an improvement or worsening of the condition) and adapt procedure(s), treatment(s), and/or timer(s) accordingly (e.g., reducing or increasing medication, adding or removing procedures/treatments, changing timer value(s), etc.).

While for purposes of simplicity of explanation, the respective processes are shown and described as a series of blocks in FIG. 2Q, it is to be understood and appreciated that the claimed subject matter is not limited by the order of the blocks, as some blocks may occur in different orders and/or concurrently with other blocks from what is depicted and described herein. Moreover, not all illustrated blocks may be required to implement the methods described herein.

Figure 3A:
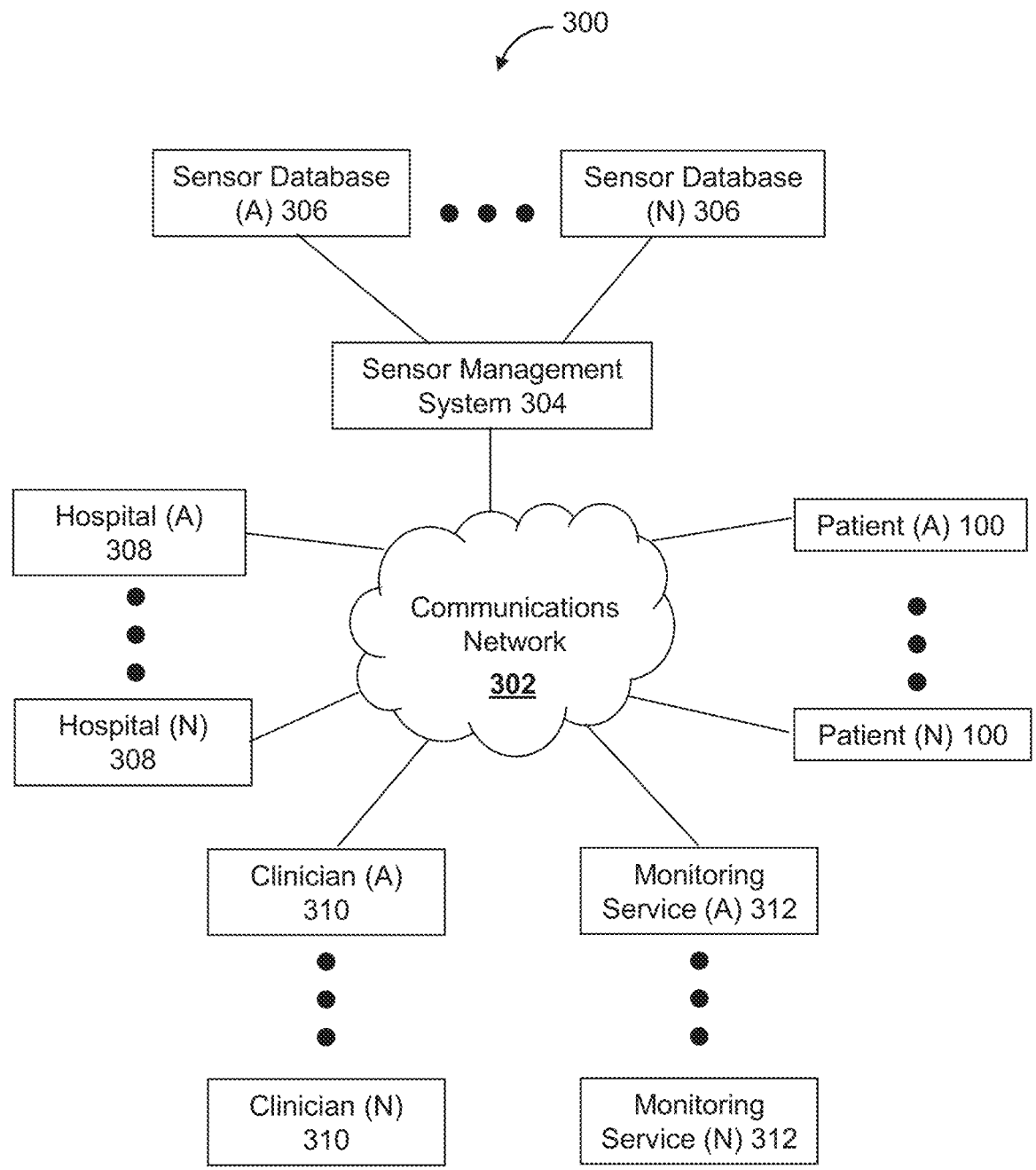
FIGS. 3A-3F are block diagrams illustrating example, non-limiting embodiments of a system for managing sensor data in accordance with various aspects of the subject disclosure described herein.

Turning now to FIGS. 3A-3F, block diagrams illustrating example, non-limiting embodiments of a system 300 for managing sensor data in accordance with various aspects of the subject disclosure is shown. FIG. 3A depicts a network architecture in which one or more sensor management systems 304 are communicatively coupled to hospitals (A)-(N) 308, clinicians (A)-(N) 310, monitoring services (A)-(N) 312, and/or patients (A)-(N) 100, singly or in combination.

Figure 3B:
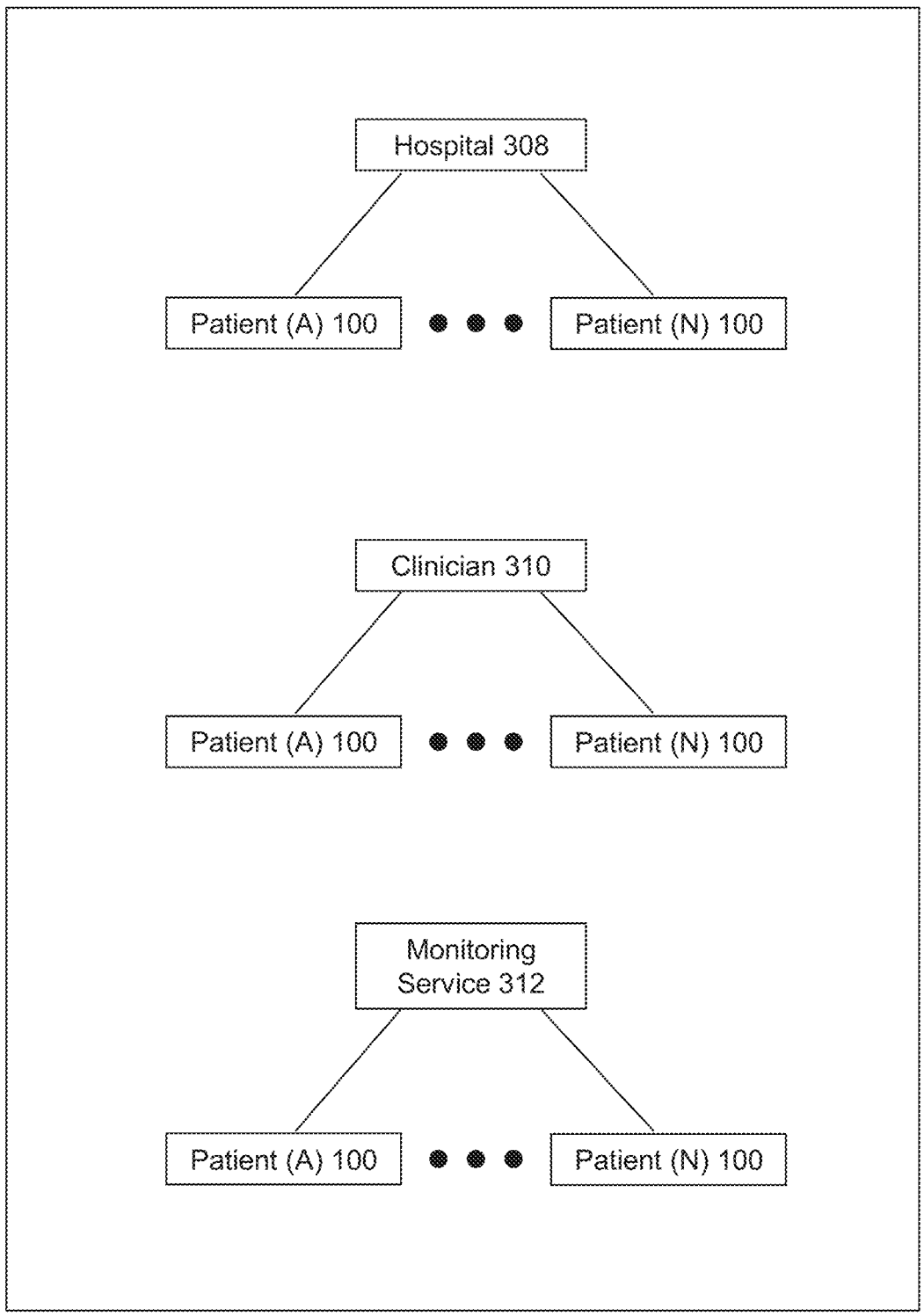

The sensor management system 304 can record and access data from sensor databases (A)-(N) 306. In an embodiment, hospitals (A)-(N) 308, clinicians (A)-(N) 310, and monitoring services (A)-(N) 312 can provide the sensor management system 304 access to patients 100 through their systems and local network devices as depicted in FIG. 3B. Alternatively, the sensor management system 304 can be communicatively coupled to patients (A)-(N) 100 directly as shown in FIG. 3A without intervening health care providers (such as hospitals, clinicians, or monitoring services), and instead provide care providers access to information of certain patients recorded in the sensor databases (A)-(N) 306.

Figure 3C:
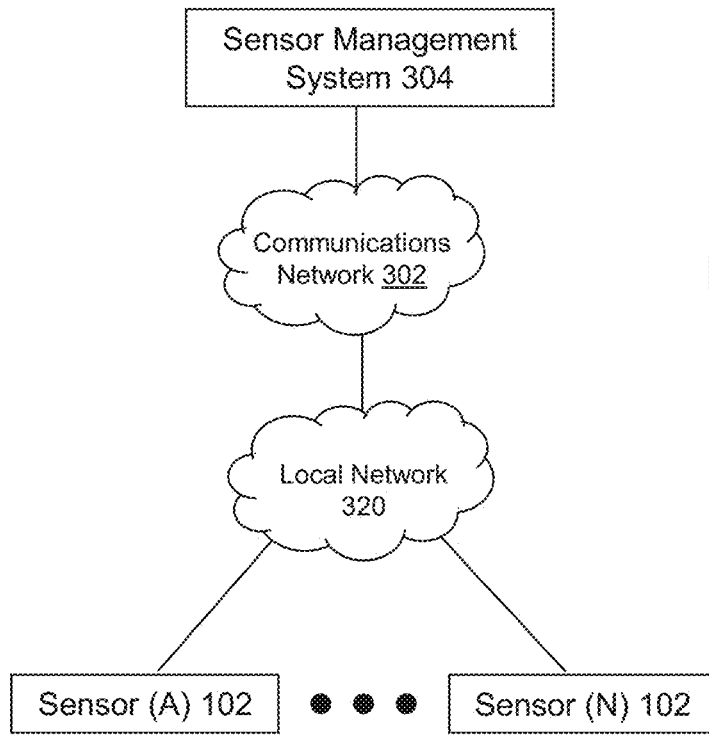
Figure 3D:
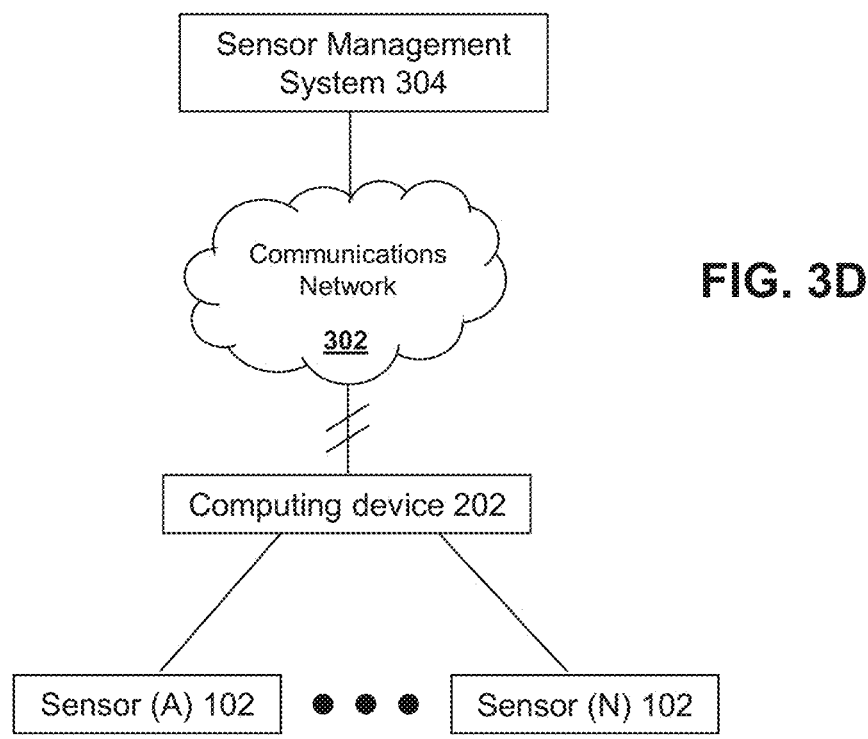

FIGS. 3C-3F depict different arrangements for managing sensors 102. In one embodiment, for example, the sensor management system 304 can be communicatively coupled to sensors 102 via the communications network 302 which is communicatively coupled to a local network 320 (e.g., a local area network, WiFi access point, etc.) having access to the sensors 102 as depicted in FIG. 3C. In another embodiment, the sensor management system 304 can be communicatively coupled to sensors 102 via the communications network 302 which is communicatively coupled to a computing device 202 (such as shown in FIG. 2B) having access to the sensors 102 as depicted in FIG. 3D. In some embodiments, the computing device 202 can operate off-line (i.e., without access to the sensor management system 304) as depicted in FIG. 3D with the hash lines. While off-line, the computing device 202 can collect sensor data from sensors 102, provision sensors 102, and perform other tasks which can be recorded locally in a memory of the computing device 202. Once the computing device 202 restores access to the sensor management system 304 via communications network 302, the computing device 202 can provide the sensor management system 304 access to its local memory to update databases 306 with new sensor data, provisioning data, and so on.

Figure 3E:
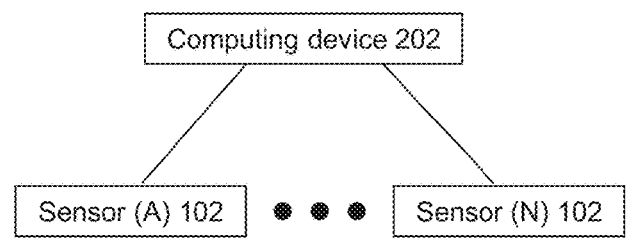
Figure 3F:
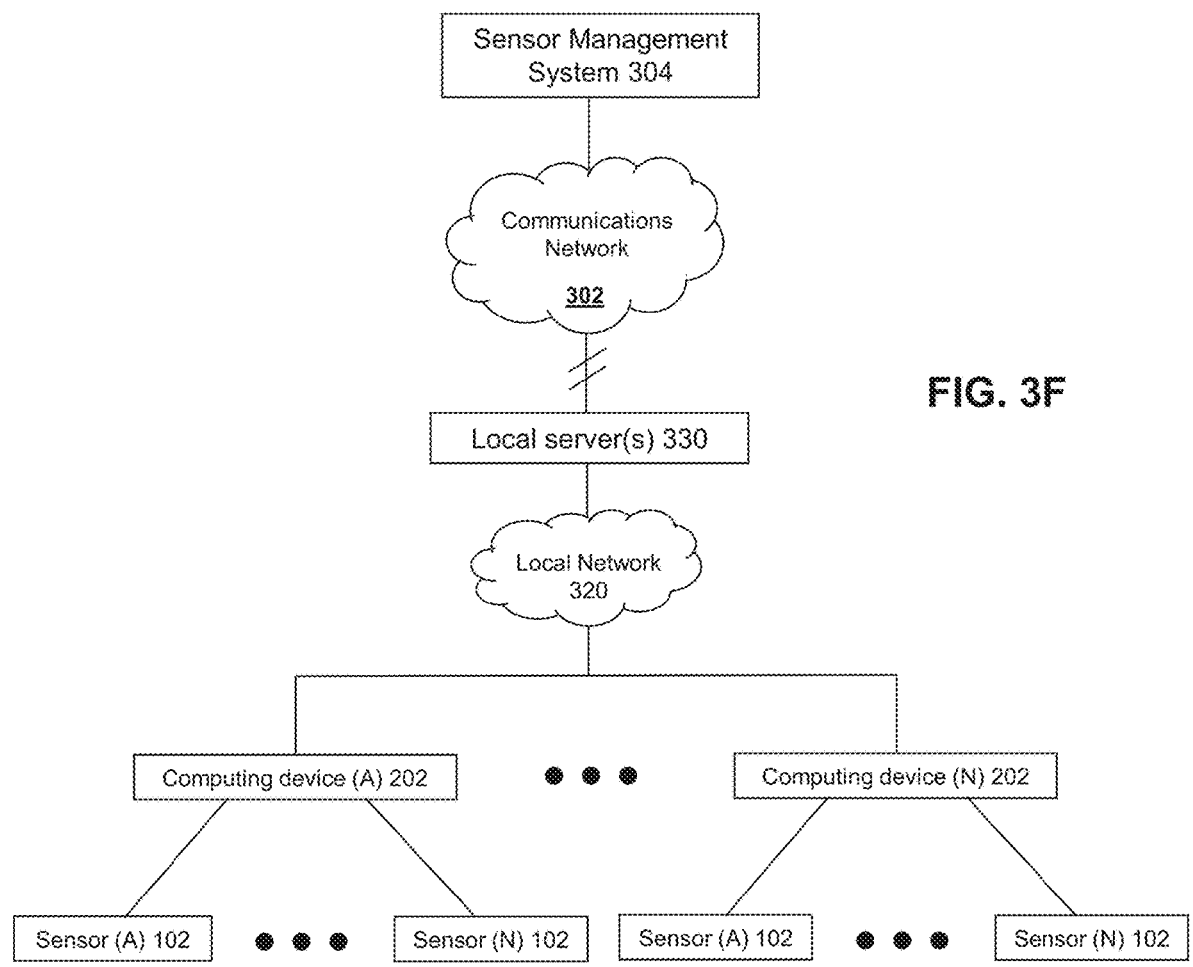

In yet another embodiment, the computing device 202 can be configured to operate independently from the sensor management system 304 as depicted in FIG. 3E and collect sensor data from sensors 102, provision sensors 102, and perform other tasks which are recorded locally in the memory of the computing device 202. In another embodiment, the sensor management system 304 can be configured to communicate with one or more local servers 330 as depicted in FIG. 3F, which have access to computing devices 202 via a local network 320. The computing devices 202 can provide sensor management information to the local servers 330. The local servers 330 in turn can provide the sensor management system 304 access to the sensor information collected from the computing devices 202. In some embodiments, the local servers 330 can also be configured to operate independently from the sensor management system 304.

It will be appreciated from the number of illustrations shown in FIGS. 3A-3F that any number of network configurations between sensors 102 and other devices managing use of the sensors 102 is possible. It is further noted that the arrangements in FIGS. 3A-3F can be adapted for managing sensors worn by a patient located in a residence, a clinic, a doctor's office, a hospital, outdoors, while in transit, while traveling, and so on.

It is also noted that the communications network 302 and the local network 320 shown in FIGS. 3A-3F can comprise a landline communications network (e.g., packet switched landline networks, circuit switched networks, etc.), a wireless communications network (e.g., cellular communications, WiFi, etc.), or combinations thereof. It is also noted that the computing device 202 of FIG. 2B can be configured to initiate communications with the biological sensor 102 and the communications network 302 to provide the sensor management system 304 access to the biological sensors 102 used by multiple patients. In this embodiment, the computing device 202 can serve as a gateway between the communications network 302 and the biological sensors 102. In other embodiments, the biological sensors 102 can gain direct access to the communications network 302 by way of a gateway that provide internet access (e.g., a WiFi access point).

The sensor management system 304 can be configured to store endless amounts of biological data of patients 100 over long periods of time (e.g., an entire lifetime and/or generations of patients) in databases 306. Such data can serve to provide historical information that may be invaluable to the patients 100 and their lineages.

Figure 4:
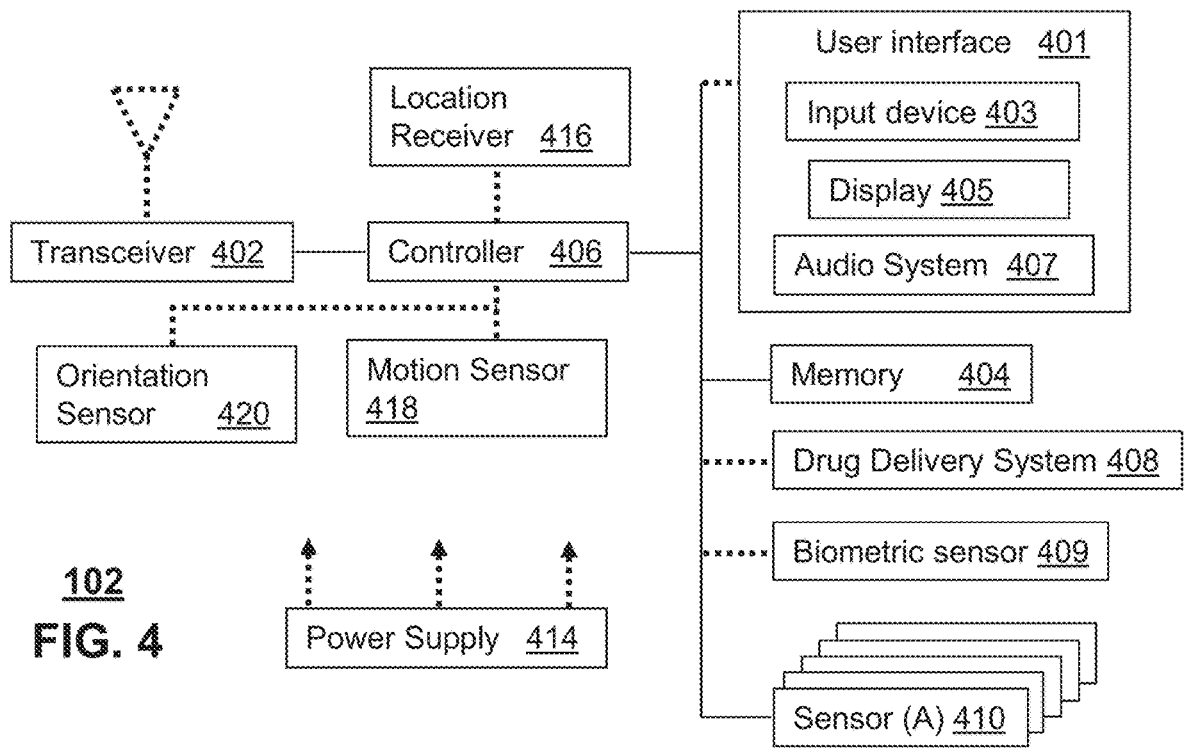
FIG. 4 is a block diagram illustrating an example, non-limiting embodiment of a biological sensor in accordance with various aspects of the subject disclosure described herein.

Turning now to FIG. 4, a block diagram illustrating an example, non-limiting embodiment of a biological sensor 102 is shown. The biological sensor 102 can comprise a wireline and/or wireless transceiver 402 (herein transceiver 402), a power supply 414, a location receiver 416, a motion sensor 418, an orientation sensor 420, a user interface (UI) 401, a memory 404, a drug delivery system 408, a biometric sensor 409, one or more sensors 410, a user interface 412, and a controller 406 for managing operations thereof. Not all of the components shown in the biological sensor 102 are necessary. For example, in one embodiment the biological sensor 102 can comprise the transceiver 402, the controller 406, the memory 404, one or more sensors 410, and the power supply 404. In other embodiments, the biological sensor 102 can further include one or more components not used in the previous embodiment such as the UI 401, the drug delivery system 408, the biometric sensor 409, the location receiver 416, the motion sensor 418, the orientation sensor 420, or any combinations thereof. Accordingly, any combinations of component of the biological sensor 102 depicted in FIG. 4 are possible and contemplated by the subject disclosure.

Although FIGS. 1 and 2A-2B depict topical applications of the biological sensor 102 on an outer skin of the patient 100, in other embodiments, the biological sensor 102 can in whole or in part be embedded in a patient 100. For example, a certain sensor 410 may be embedded in a skin of the patient 100 while other components of the biological sensor 102 may be located on an outer surface of the skin. In other embodiments, a certain sensor 410 may be attached to an organ (e.g., the heart). Accordingly, the biological sensor 102 can be located in a number of places within a patient's body, outside a patient's body, or combinations thereof.

The UI 401 can include an input device 403. In one embodiment, the input device 403 can comprise one or more depressible electromechanical buttons. In other embodiments, or in combination, the input device 403 can comprise a touch sensitive interface such as a pad that utilizes capacitive, resistive or other forms of touch-sensing technology. The UI 401 can further include a display 405 such as monochrome or color LCD (Liquid Crystal Display), OLED (Organic Light Emitting Diode) or other suitable display technology for conveying images. In some embodiments, the input device 403 and the display 405 can be combined to form a touch-sensitive display. The UI 401 can also include an audio system 407 that utilizes audio technology for facilitating generation of audible signals via, for example, a speaker, and/or to receive audio signals via, for example, a microphone.

The transceiver 402 can support short-range or long-range wireless access technologies such as RFID, Near Field Communications (NFC), Bluetooth®, ZigBee®, WiFi, DECT, or cellular communication technologies, just to mention a few (Bluetooth® and ZigBee® are trademarks registered by the Bluetooth® Special Interest Group and the ZigBee® Alliance, respectively). Cellular technologies can include, for example, CDMA-1X, UMTS/HSDPA, GSM/GPRS, TDMA/EDGE, EV/DO, WiMAX, SDR, LTE, as well as other next generation wireless communication technologies as they arise. The transceiver 402 can also be adapted to support cable protocols (e.g., USB, Firewire, Ethernet, or other suitable cable technologies), circuit-switched wireline access technologies (such as PSTN), packet-switched wireline access technologies (such as TCP/IP, VoIP, etc.), or combinations thereof.

The drug delivery system 408 can comprise microneedles, one or more reservoirs of one or more drugs, and a piezo inkjet (not shown), which combined form a microfluidic system. The piezo inkjet can be coupled to the one or more reservoirs to selectively deliver dosages via the microneedles. The piezo inkjet can be coupled to the controller 406 which can provide controlled delivery of dosages of one or more drugs by the drug delivery system 408. The biometric sensor 409 can be a fingerprint sensor, a voice sensor (with a built-in microphone), or any other type of suitable biometric sensor for identifying a user of the biological sensor 102. The sensors 410 can use common biological sensing technology for measuring biological functions of a patient including, but not limited to, temperature, perspiration, pulse rate, blood pressure, respiration rate, glucose levels in the blood, SpO2, ECG/EKG, particulates in the air that may cause an ailment to an individual (e.g., pollen or other forms of allergens in the air), and so on.

The power supply 414 can utilize common power management technologies such as replaceable and rechargeable batteries, supply regulation technologies, and/or charging system technologies for supplying energy to the components of the biological sensor 102 to facilitate long-range or short-range portable applications. Alternatively, or in combination, the power supply 414 can utilize external power sources such as DC power supplied over a physical interface such as a USB port or other suitable tethering technologies.

In other embodiments, the biological sensor can be battery-less. In this embodiment, the power supply 414 can utilize circuitry that powers the components of the biological sensor 102 utilizing RF energy received by an antenna or other receptive element. In one embodiment, for example, the biological sensor 102 can use NFC technology to intercept RF signals generated by the computing device 202 when the computing device 202 is held about a foot or less away from the biological sensor 102. In another embodiment, the biological sensor 102 can utilize battery-less technology similar to that used by passive RFID devices. Other suitable battery-less technologies can be applied to the embodiments of the subject disclosure.

The location receiver 416 can utilize location technology such as a global positioning system (GPS) receiver capable of identifying a location of the biological sensor 102 using signals generated by a constellation of GPS satellites. The motion sensor 418 can utilize motion sensing technology such as an accelerometer, a gyroscope, or other suitable motion sensing technology to detect a motion of the biological sensor 102 in three-dimensional space. The orientation sensor 420 can utilize orientation sensing technology such as a magnetometer to detect the orientation of the biological sensor 102 (north, south, west, east, as well as combined orientations in degrees, minutes, or other suitable orientation metrics).

The controller 406 can utilize computing technologies such as a microprocessor, a digital signal processor (DSP), programmable gate arrays, application specific integrated circuits, which can be coupled to the memory 404. The memory 404 can utilize memory technologies such as Flash, ROM, RAM, SRAM, DRAM or other storage technologies for executing instructions, controlling operations of the biological sensor 102, and for storing and processing sensing data supplied by the aforementioned components of the biological sensor 102.

Figure 5:
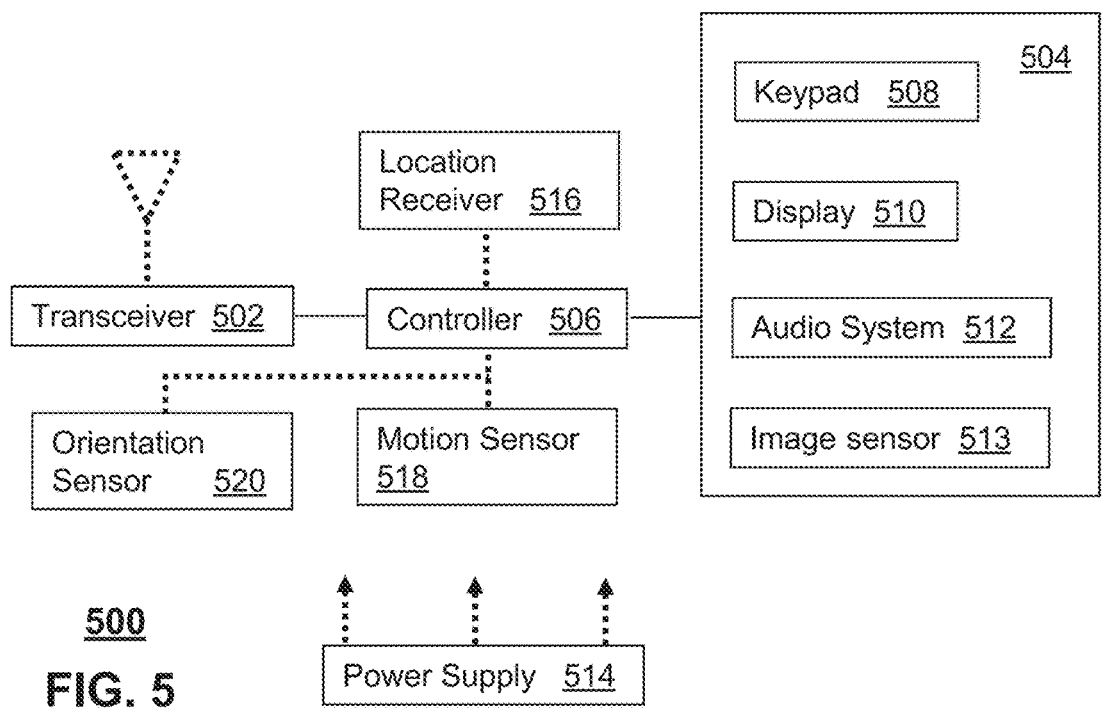
FIG. 5 is a block diagram illustrating an example, non-limiting embodiment of a computing device in accordance with various aspects of the subject disclosure described herein.

Turning now to FIG. 5, a block diagram illustrating an example, non-limiting embodiment of a computing device 202 in accordance with various aspects of the subject disclosure is shown. Computing device 202 can comprise a wireline and/or wireless transceiver 502 (herein transceiver 502), a user interface (UI) 504, a power supply 514, a location receiver 516, a motion sensor 518, an orientation sensor 520, and a controller 506 for managing operations thereof. The transceiver 502 can support short-range or long-range wireless access technologies such as Bluetooth®, ZigBee®, WiFi, DECT, or cellular communication technologies, just to mention a few. Cellular technologies can include, for example, CDMA-1X, UMTS/HSDPA, GSM/GPRS, TDMA/EDGE, EV/DO, WiMAX, SDR, LTE, as well as other next generation wireless communication technologies as they arise. The transceiver 502 can also be adapted to support circuit-switched wireline access technologies (such as PSTN), packet-switched wireline access technologies (such as TCP/IP, VoIP, etc.), and combinations thereof.

The UI 504 can include a depressible or touch-sensitive keypad 508 with a navigation mechanism such as a roller ball, a joystick, a mouse, or a navigation disk for manipulating operations of the computing device 202. The keypad 508 can be an integral part of a housing assembly of the computing device 202 or an independent device operably coupled thereto by a tethered wireline interface (such as a USB cable) or a wireless interface supporting for example Bluetooth®. The keypad 508 can represent a numeric keypad commonly used by phones, and/or a QWERTY keypad with alphanumeric keys. The UI 504 can further include a display 510 such as monochrome or color LCD (Liquid Crystal Display), OLED (Organic Light Emitting Diode) or other suitable display technology for conveying images to an end user of the computing device 202. In an embodiment where the display 510 is touch-sensitive, a portion or all of the keypad 508 can be presented by way of the display 510 with navigation features.

In another embodiment, display 510 can use touch screen technology to serve as a user interface for detecting user input. As a touch screen display, the computing device 202 can be adapted to present a user interface with graphical user interface (GUI) elements that can be selected by a user with a touch of a finger. The touch screen display 510 can be equipped with capacitive, resistive or other forms of sensing technology to detect how much surface area of a user's finger has been placed on a portion of the touch screen display. This sensing information can be used to control the manipulation of the GUI elements or other functions of the user interface. The display 510 can be an integral part of the housing assembly of the computing device 202 or an independent device communicatively coupled thereto by a tethered wireline interface (such as a cable) or a wireless interface.

The UI 504 can also include an audio system 512 that utilizes audio technology for conveying low volume audio (such as audio heard in proximity of a human ear) and high volume audio (such as speakerphone for hands free operation). The audio system 512 can further include a microphone for receiving audible signals of an end user. The audio system 512 can also be used for voice recognition applications. The UI 504 can further include an image sensor 513 such as a charged coupled device (CCD) camera for capturing still or moving images.

The power supply 514 can utilize common power management technologies such as replaceable and rechargeable batteries, supply regulation technologies, and/or charging system technologies for supplying energy to the components of the computing device 202 to facilitate long-range or short-range portable applications. Alternatively, or in combination, the charging system can utilize external power sources such as DC power supplied over a physical interface such as a USB port or other suitable tethering technologies.

The location receiver 516 can utilize location technology such as a GPS receiver for identifying a location of the computing device 202 based on signals generated by a constellation of GPS satellites, which can be used for facilitating location services such as navigation. The motion sensor 518 can utilize motion sensing technology such as an accelerometer, a gyroscope, or other suitable motion sensing technology to detect motion of the computing device 202 in three-dimensional space. The orientation sensor 520 can utilize orientation sensing technology such as a magnetometer to detect the orientation of the computing device 202 (north, south, west, and east, as well as combined orientations in degrees, minutes, or other suitable orientation metrics).

The controller 506 can utilize computing technologies such as a microprocessor, a digital signal processor (DSP), programmable gate arrays, application specific integrated circuits, and/or a video processor with associated storage memory such as Flash, ROM, RAM, SRAM, DRAM or other storage technologies for executing computer instructions, controlling, and processing data supplied by the aforementioned components of the computing device 202.

Other components not shown in FIG. 5 can be used in one or more embodiments of the subject disclosure. For instance, the computing device 202 can also include a slot for adding or removing an identity module such as a Subscriber Identity Module (SIM) card. SIM cards can be used for identifying subscriber services, executing programs, storing subscriber data, and so forth. The computing device 202 as described herein can operate with more or less of the circuit components shown in FIG. 5. These variant embodiments can be used in one or more embodiments of the subject disclosure.

Figure 6:
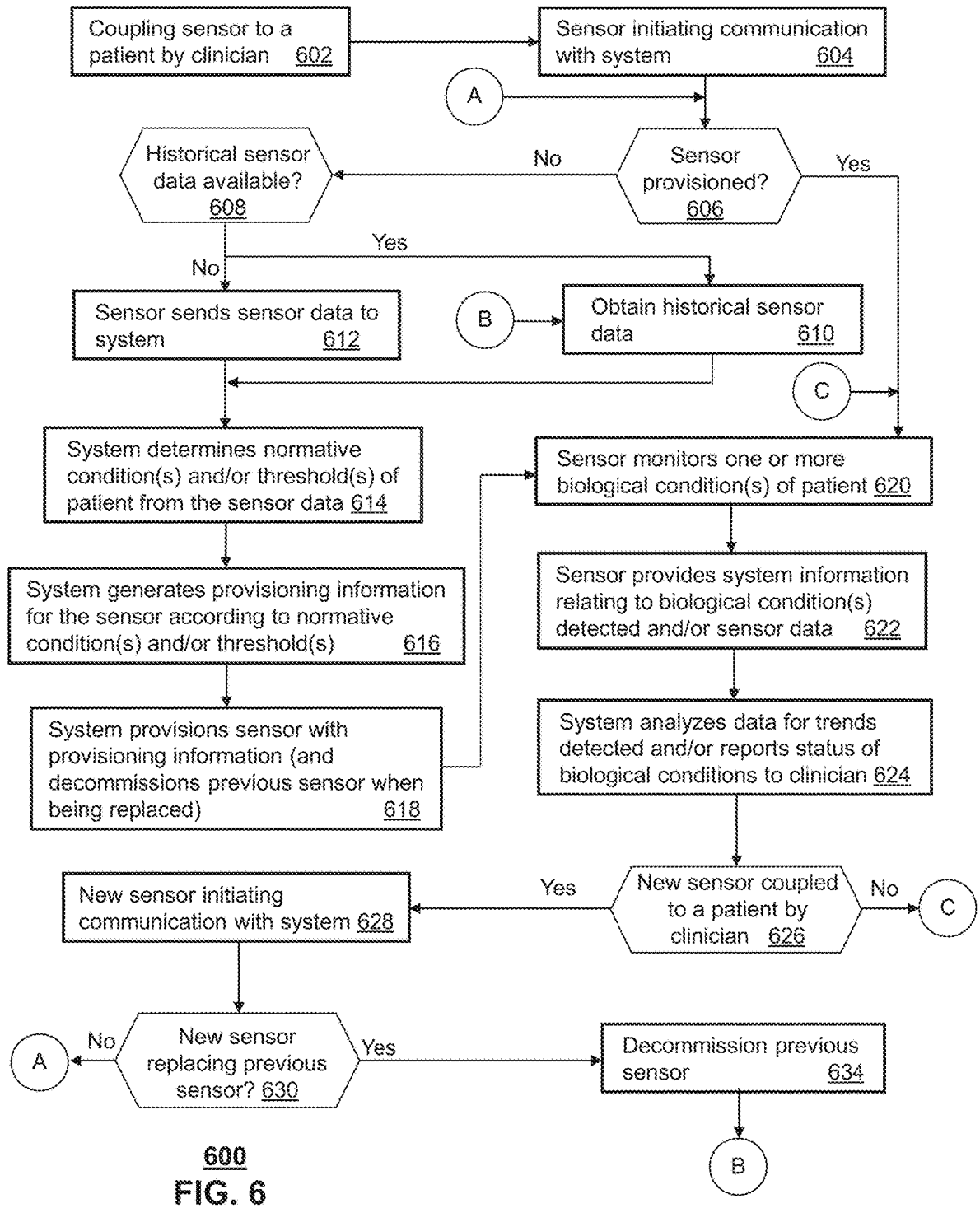
FIG. 6 is a block diagram illustrating an example, non-limiting embodiment of a method in accordance with various aspects of the subject disclosure described herein.

Turning now to FIG. 6, a block diagram illustrating an example, non-limiting embodiment of a method 600 in accordance with various aspects of the subject disclosure is shown. Method 600 can be applied to any combination of the embodiments of FIGS. 1, 2A-2B, 3A-3B, and 4-5. Method 600 can begin with step 602 where a biological sensor 102 is placed on a patient 100 by one of a number of known means such as, for example, being placed by a clinician (e.g., a nurse as shown in FIG. 2A). In one embodiment, the biological sensor 102 can utilize an adhesive for coupling to the skin of the patient 100. In another embodiment, the clinician can be a surgeon that implants the biological sensor 102 in whole or in part in a body portion of the patient 100.

At step 604, the biological sensor 102 can be configured to initiate communications with a system. In one embodiment the biological sensor 102 can initiate communications with a computing device 202 such as shown in FIG. 2B. In this embodiment, the biological sensor 102 can initiate communications utilizing, for example, short range wireless technology such as near field communications (NFC), Bluetooth®, ZigBee®, WiFi or other suitable short range wireless communications technology. The computing device 202 in turn can communicate with the sensor management system 304 via the communications network 302 to provide the sensor management system 304 access to information supplied by the biological sensor 102.

In another embodiment, the biological sensor 102 can initiate communications with the sensor management system 304 by way of the communications network 302 utilizing long range wireless technology such cellular technology or other suitable long range wireless communications technology. In yet another embodiment, the biological sensor 102 can initiate communications with the sensor management system 304 by way of the communications network 302 utilizing wireline communications technology.

In one embodiment, for example, the biological sensor 102 can be tethered to the computing device 202 with a cable (e.g., a USB cable). In this embodiment, the computing device 202 can provide the sensor management system 304 access to information supplied by the biological sensor 102. In another embodiment, the biological sensor 102 can have access to a local network providing connectivity to the Internet by way of a cable (e.g., Ethernet cable). In this embodiment, the sensor management system 304 can have direct access to the biological sensor 102.

Based on the foregoing embodiments, the system referred to in step 604 and in subsequent steps can be represented by the computing device 202, the sensor management system 304, or a combination thereof. The term system as utilized in method 600 can be adapted to represent solely the computing device 202, solely the sensor management system 304, or a combination of the computing device 202 and the sensor management system 304, each configured to cooperate therebetween in a manner that achieves the embodiments described by method 600. It is also noted that other arrangements are possible as shown in FIGS. 3A-3F.

At step 606, the system can determine whether the biological sensor 102 is provisioned. This determination can be made a number of ways. For example, a clinician 101 can enter information on a computing device 202 which signals the sensor management system 304 that the biological sensor 102 is a new sensor placed on patient 100, which has not been provisioned. In another embodiment, the biological sensor 102 can be polled by the sensor management system 304 (or by the computing device 202) to determine if the biological sensor 102 has been provisioned. In another embodiment, the sensor management system 304 (and/or the computing device 202) can be configured to determine that a prior biological sensor 102 has been used (or is currently in use) by the patient 100 and the new biological sensor 102 that was detected is of a different serial number, but functionally equivalent or similar to the prior biological sensor 102.

In another embodiment, the sensor management system 304 (or the computing device 202) can be configured to receive from the biological sensor 102 an identification of the patient 100. To obtain this information, the biological sensor 102 can be configured to receive the identification of the patient 100 from the computing device 202. In another embodiment, the biological sensor 102 can obtain the identification from a wristband worn by the patient 100 that includes an RFID device or other device suitable to convey the identification of the patient 100 wirelessly to the biological sensor 102. Upon obtaining the identification of the patient 100, the sensor management system 304 (or the computing device 202) can be configured to retrieve a record of the patient 100 indexed according to the identification of the patient, and detect therefrom that the biological sensor 102 is not identified in a chart of the patient 100.

In yet another embodiment, the sensor management system 304 (or the computing device 202) can be configured to detect an expiration of a utilization period applied to a prior biological sensor 102 and determine that the biological sensor 102 now detected is a replacement sensor that has not been provisioned. There are many other ways to perform inventory management of biological sensors 102 to determine when the biological sensor 102 is not provisioned. For example, the sensor management system 304 (or the computing device 202) can be configured to detect that provisioning data stored by the sensor management system 304 (or the computing device 202) is not synchronized with data stored in the biological sensor 102 by comparing time stamps associated with data stored in the biological sensor 102 to time stamps associated with data stored in the databases 306 of the sensor management system 304 (or the memory of the computing device 202). If the time stamps of the sensor management system 304 (or the memory of the computing device 202) are not the same as the time stamps of the biological sensor 102, then the sensor management system 304 (or the computing device 202) can detect the biological sensor 102 has not been provisioned. In yet another embodiment, the biological sensor 102 can provide the sensor management system 304 (or the computing device 202) information indicating it has not been provisioned.

These and other alternative embodiments for determining whether a biological sensor 102 is provisioned are contemplated by the subject disclosure.

Referring back to step 606, if the sensor management system 304 (or the computing device 202) detects the biological sensor 102 is not provisioned, the sensor management system 304 (or the computing device 202) can proceed to step 608 where it can determine whether historical sensor data is available. The historical sensor data can originate from prior biological sensors used by the patient 100. The historical sensor data can represent data captured minutes, hours, days, months or years before the new biological sensor 102 is detected at step 604. If the historical sensor data is available, the sensor management system 304 (or the computing device 202) can proceed to step 610 to obtain such data from a memory device used to retain records of the patient 100 (e.g., the customer sensor databases 306 or an internal memory of the computing device 202).

Once the historical sensor data is obtained, the sensor management system 304 (or the computing device 202) can proceed to step 614 to determine normative conditions and/or thresholds for detecting one or more biological conditions of the patient 100 from the historical sensor data collected from one or more previously used biological sensors 102. The historical sensor data collected from the one or more previously used biological sensors 102 can be over a period of time such as minutes, hours, days, weeks, months, years, or longer. The time period used for selecting historical sensor data can be driven by a number of factors. For example, the time period may be based on a specific protocol initiated by a clinician (nurse and/or doctor). The protocol can be initiated as a result of a procedure performed on the patient (e.g., surgery, therapy, drug application, and so on), a protocol for monitoring patient vitals, or a protocol customized by the clinician to address a particular disease. Any medical protocol prescribed by the clinician or a medical organization are contemplated by the subject disclosure. Once a time period is selected, the historical sensor data can be analyzed to identify one or more normative conditions and/or thresholds for the patient 100. FIGS. 7A-7D illustrate non-limiting example embodiments for determining normative conditions, and thresholds for detecting biological conditions.

Figure 7A:
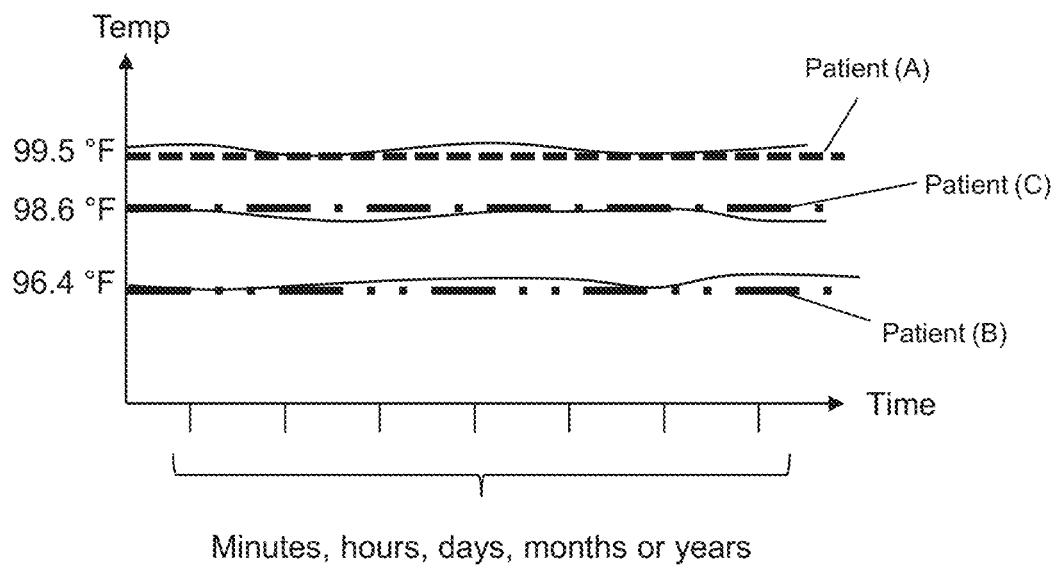
FIGS. 7A-7B are block diagrams illustrating example, non-limiting embodiments of plots of sensor data of a plurality of patients in accordance with various aspects of the subject disclosure described herein.

Turning now to FIG. 7A, a block diagram illustrating an example, non-limiting embodiment of a plot of sensor data of a plurality of patients in accordance with various aspects of the subject disclosure is shown. FIG. 7 depicts three patients (A), (B) and (C). Historical sensor data of patient (A) indicates that the patient has had an average temperature of 99.5° Fahrenheit (F) over a select period. In one embodiment, the clinician may be aware that patient (A) has exhibited this temperature over extended periods of time and thereby can form an opinion that such a temperature does not pose a health risk to patient (A) even though it is higher than a population norm of 98.6° F. In one embodiment, the clinician can record his opinion in a chart of patient (A), which can be accessible to the sensor management system 304 (or the computing device 202). In one embodiment, the sensor management system 304 (or the computing device 202) can access the chart of patient (A) and determine from the clinician's opinion that such a temperature may be considered a normative condition for patient (A) given the physiological state and health of patient (A). In another embodiment, the sensor management system 304 (or the computing device 202) can analyze the sensor data of the patient (A) in relation to the patient's temperature, other sensory data (e.g., blood pressure, pulse rate, respiration rate, blood pressure and so on) and/or other medical history, and determine, without relying on the clinician's opinion, that such a temperature may be considered a normative condition for patient (A) given the physiological state and health of patient (A).

In another embodiment, the clinician may be aware that patient (A) may be subject to an illness that the clinician expects will result in a rise in temperature, which the clinician records in the chart of patient (A). In yet another embodiment, the clinician may be applying a drug treatment to patient (A) that the clinician knows will cause a rise in temperature, which the clinician records in the chart of patient (A). The sensor management system 304 (or the computing device 202) can be configured to analyze the chart of patient (A) and consider the temperature a normative condition of patient (A) based on the entries of the clinician indicating an expected rise in temperature. Alternatively, the sensor management system 304 (or the computing device 202) can be configured to analyze the sensor data, detect from the chart that patient (A) has an illness, or is subject to a drug therapy, access information relating to the illness or drug therapy (from databases 306 or other information storage system(s)), and determine, without relying on the clinician's opinion, from the sensor data and the information obtained about the illness or drug therapy that the temperature of patient (A) would be higher than normal, and therefore can be considered a normative condition of patient (A).

Turning now to patient (B), the historical sensor data of patient (B) indicates that the patient has had an average temperature of 96.4° F. over a select period. In one embodiment, the clinician may be aware that patient (B) has exhibited this temperature over extended periods of time and that such a temperature does not pose a health risk to patient (B). Clinician can record his or her opinion in a chart of patient (B) accessible to the sensor management system 304 (or the computing device 202). Thus such a temperature may be considered a normative condition for patient (B) given the physiological state and health of patient (B). In another embodiment, the clinician may be aware that patient (B) may be subject to an illness that results in such a temperature. In yet another embodiment, the clinician may be applying a drug treatment to patient (B) that the clinician knows will cause a drop in temperature.

The sensor management system 304 (or the computing device 202) can be configured to analyze the chart of patient (B) and consider the temperature a normative condition of patient (B) based on the entries of the clinician indicating an expected drop in temperature. Alternatively, the sensor management system 304 (or the computing device 202) can be configured to analyze the sensor data, detect from the chart that patient (B) has an illness, or is subject to a drug therapy, access information relating to the illness or drug therapy (from databases 306 or other information storage system(s)), and determine, without relying on the clinician's opinion, from the sensor data and the information obtained about the illness or drug therapy that the temperature of patient (B) would be lower than normal, and therefore can consider it a normative condition of patient (B).

Turning now to patient (C), the historical sensor data of patient (C) indicates that the patient has had an average temperature of 98.6° F. over a select period, which coincides with what most clinicians may consider an average temperature for the general population. Thus the clinician does not have to consider exceptions for patient (C). Accordingly, this temperature will be used as a normative condition for patient (C). The sensor management system 304 (or the computing device 202) can be configured to analyze the chart of patient (C) and consider the temperature a normative condition of patient (C). Alternatively, the sensor management system 304 (or the computing device 202) can be configured to analyze the sensor data, and determine, without relying on the clinician's opinion, that the sensor data coincides with the general population, and therefore can consider it a normative condition of patient (C).

Figure 7B:
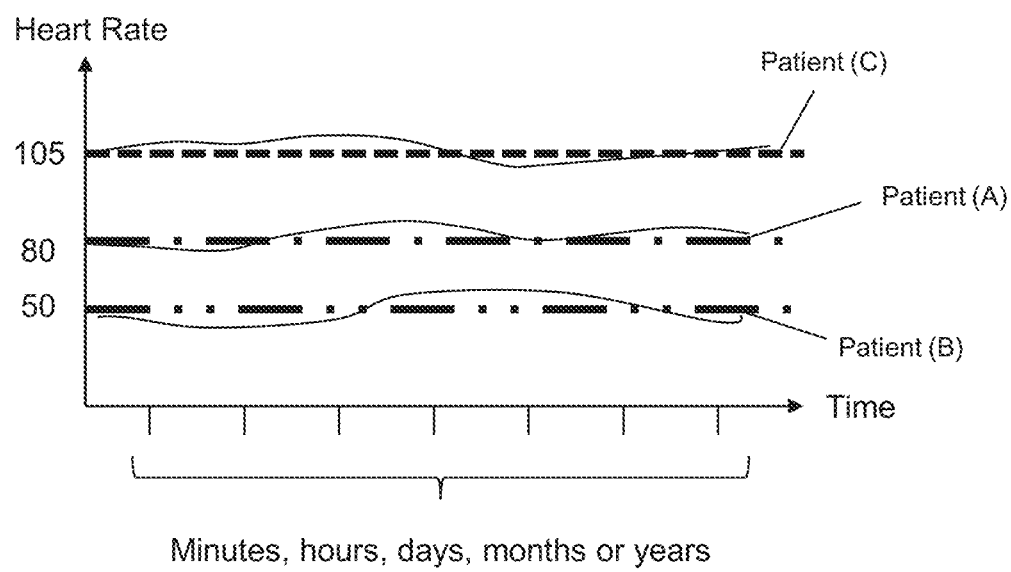

Turning now to FIG. 7B, a block diagram illustrating an example, non-limiting embodiment of a plot of sensor data of the plurality of patients (A)-(C) of FIG. 7A. Historical sensor data of patient (A) indicates that the patient has had an average pulse rate of 80 beats per minute over a select period. The sensor management system 304 (or the computing device 202) can be configured to consider such a pulse rate a normative condition for patient (A) given that a range of 60 to 100 beats per minute is generally a healthy pulse rate. In one embodiment, the clinician can record his opinion in a chart of patient (A), which can be accessed by the sensor management system 304 (or the computing device 202).

Turning now to patient (B), the historical sensor data of patient (B) indicates that the patient has had an average pulse rate of 50 beats per minute over a select period. In one embodiment, the clinician may be aware that patient (B) has exhibited this pulse rate over extended periods of time given the athletic training undertaken by patient (B). In one embodiment, the clinician can record his opinion in a chart of patient (B), which can be accessed by the sensor management system 304 (or the computing device 202). In one embodiment, the sensor management system 304 (or the computing device 202) can access the chart of patient (B) and determine from the clinician's opinion that such a pulse rate may be considered a normative condition for patient (B) given the physiological state and health of patient (B). In another embodiment, the sensor management system 304 (or the computing device 202) can analyze the sensor data of the patient (B) in relation to the patient's pulse rate, other sensory data (e.g., temperature, blood pressure, respiration rate, blood pressure and so on) and other medical history, and determine, without relying on the clinician's opinion, that such a pulse rate may be considered a normative condition for patient (B) given the physiological state and health of patient (B).

Turning now to patient (C), the historical sensor data of patient (C) indicates that the patient has had an average pulse rate of 105 beats per minute over a select period, which is above normal. In one embodiment, the clinician may be aware that patient (C) has a condition such as, for example, hypertension, coronary artery disease, thyroid disease, etc., which can result in a higher pulse rate that the clinician records in the chart of patient (C). In yet another embodiment, the clinician may be applying a drug treatment to patient (C) that the clinician knows will cause a rise in pulse rate, which the clinician records in the chart of patient (C).

In one embodiment, the sensor management system 304 (or the computing device 202) can be configured to analyze the chart of patient (C) and consider the pulse rate a normative condition of patient (C) based on the entries of the clinician indicating an expected rise in pulse rate. Alternatively, the sensor management system 304 (or the computing device 202) can be configured to analyze the sensor data, detect from the chart that patient (C) has an illness, or is subject to a drug therapy, access information relating to the illness or drug therapy (from databases 306 or other information storage system(s)), and determine, without relying on the clinician's opinion, from the sensor data and the information obtained about the illness or drug therapy that the pulse rate of patient (C) would be higher than normal, and therefore can be considered a normative condition of patient (C).

Figure 7C:
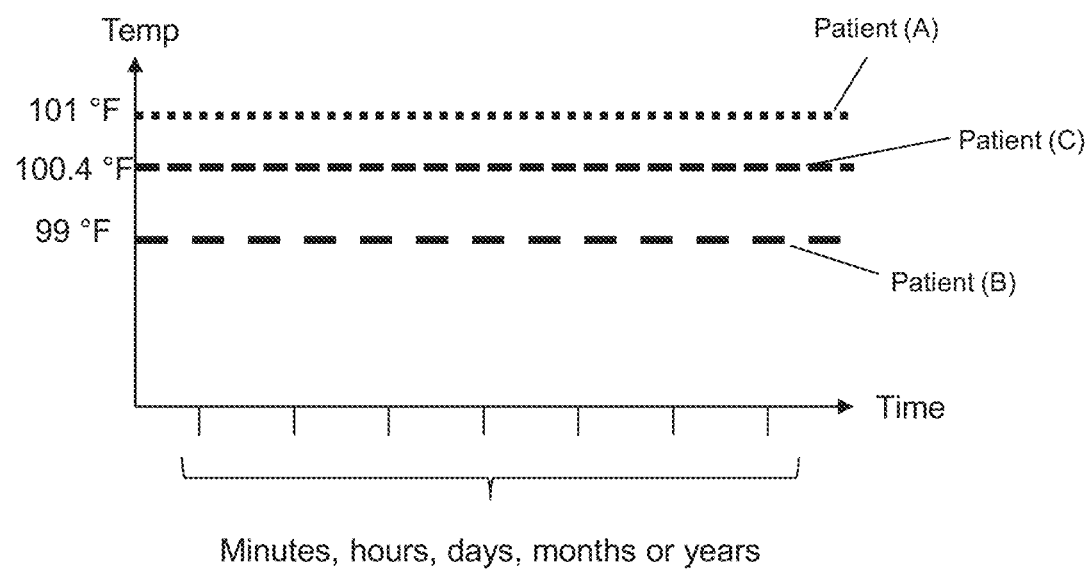
FIGS. 7C-7D are block diagrams illustrating example, non-limiting embodiments of thresholds used for monitoring biological conditions of the plurality of patients of FIGS. 7A-7B in accordance with various aspects of the subject disclosure described herein.

Turning now to FIG. 7C, a block diagram illustrating an example, non-limiting embodiment of temperature thresholds used for monitoring biological conditions of the plurality of patients (A)-(C) according to the sensor data of FIG. 7A. Turning now to patient A, given the normative condition of patient (A) averages at 99.5° F., the clinician may consider an adverse biological condition to begin at 101° F. If, for example, patient (A) does not have an illness or is not being treated with drug therapy to cause a normative condition at 99.5° F., then a threshold of 101° F. may be considered the beginning of a fever. If, on the other hand, patient (A) is subject to an illness or drug therapy resulting in the normative condition, then a rise in temperature to 101° F. may reflect an adverse biological condition that is more than just a fever. For example, the adverse biological condition may represent a body's negative reaction to the drug therapy and/or a worsening of the illness. In one embodiment, the threshold can be established by the clinician, which the clinician can record in the chart of patient (A). In another embodiment the threshold can be established by protocols relating to the illness and/or the drug therapy.

In one embodiment, the sensor management system 304 (or the computing device 202) can be configured to analyze the chart of patient (A) and generate the threshold shown in FIG. 7C. Alternatively, the sensor management system 304 (or the computing device 202) can be configured to analyze the normative condition of patient (A), detect from the chart that patient (A) has an illness, and/or is subject to a drug therapy, access information relating to the illness and/or drug therapy (e.g., specific protocols), and determine, without relying on the clinician's proposed threshold, the threshold shown in FIG. 7C.

Turning now to patient (B), given the normative condition of patient (B) averages at 96.4° F., the clinician may consider an adverse biological condition to begin at 99° F. If, for example, patient (B) does not have an illness or is not being treated with drug therapy to cause a normative condition at 96.4° F., then a threshold of 99° F. may be considered the beginning of a fever. If, on the other hand, patient (B) is subject to an illness or drug therapy resulting in the normative condition, then a rise in temperature to 99° F. may reflect an adverse biological condition that is more than just a fever. For example, the adverse biological condition may represent a body's negative reaction to the drug therapy and/or a worsening of the illness. In one embodiment, the threshold can be established by the clinician, which the clinician can record in the chart of patient (B). In another embodiment the threshold can be established by protocols relating to the illness and/or the drug therapy.

In one embodiment, the sensor management system 304 (or the computing device 202) can be configured to analyze the chart of patient (B) and generate the threshold shown in FIG. 7C. Alternatively, the sensor management system 304 (or the computing device 202) can be configured to analyze the normative condition of patient (B), detect from the chart that patient (B) has an illness, and/or is subject to a drug therapy, access information relating to the illness and/or drug therapy (e.g., specific protocols), and determine, without relying on the clinician's proposed threshold, the threshold shown in FIG. 7C.

Turning now to patient (C), given the normative condition of patient (C) averages at 98.6° F. is considered normal for the general population, the clinician may consider an adverse biological condition to begin at 100.4° F. Such a threshold can be used for detecting a fever. The clinician can record in the chart of patient (C) that patient (C) exhibits the temperature norm of the general population. The sensor management system 304 (or the computing device 202) can be configured to analyze the chart of patient (C) and generate the threshold shown in FIG. 7C. Alternatively, the sensor management system 304 (or the computing device 202) can be configured to analyze the normative condition of patient (C), and determine that an appropriate threshold for detecting a fever follows the norm of the general population and thus arrive at the threshold shown in FIG. 7C.

Figure 7D:
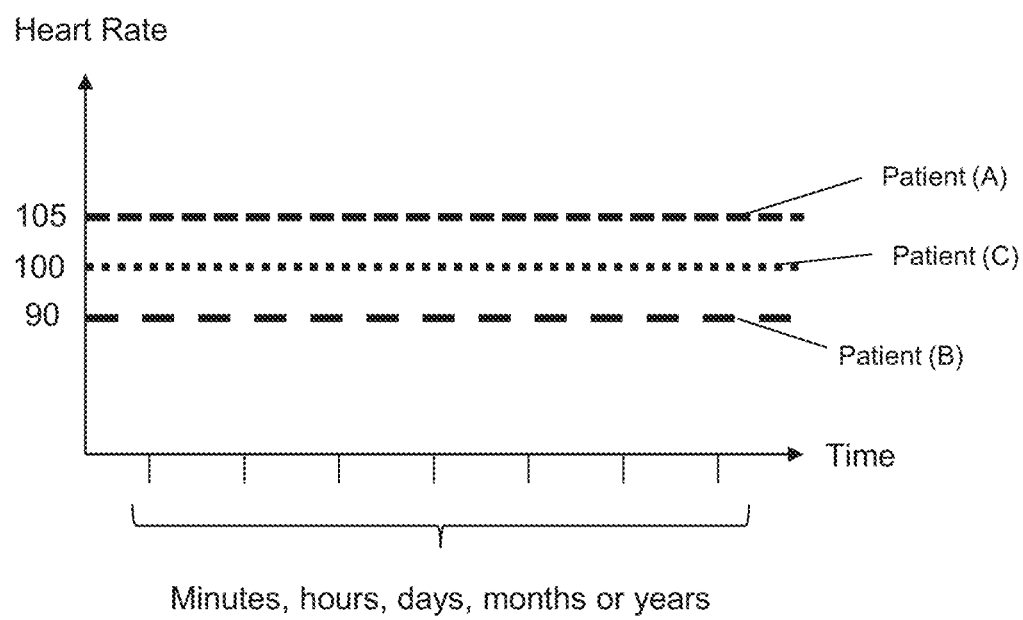

Turning now to FIG. 7D, a block diagram illustrating an example, non-limiting embodiment of pulse rate thresholds used for monitoring biological conditions of the plurality of patients (A)-(C) according to the sensor data of FIG. 7B. Turning now to patient A, given the normative condition of patient (A) averages at 80 beats per minute, which is considered normal for the general population, the clinician may consider an adverse biological condition to begin at 105 beats per minute when the patient is at rest (5% above the norm of the general population, which is 100 beats per minute). The biological sensor 102 used by patient (A) can detect that the patient is at rest utilizing, for example, the motion sensor 418 depicted in FIG. 4. In one embodiment, the threshold can be established by the clinician, which the clinician can record in the chart of patient (A). In one embodiment, the sensor management system 304 (or the computing device 202) can be configured to analyze the chart of patient (A) and generate the threshold shown in FIG. 7D. Alternatively, the sensor management system 304 (or the computing device 202) can be configured to analyze the normative condition of patient (A), and determine, without relying on the clinician's opinion, that patient (A) should use a threshold applied to the general population, such as, for example, a threshold of 100 beats per minute.

Turning now to patient (B), given the normative condition of patient (B) averages at 50 beats per minute, if, for example, patient (B) does not have an illness and is not being treated with drug therapy to cause a normative condition at 50 beats per minute, then the clinician may consider an adverse biological condition to begin at 90 beats per minute when the patient is at rest. Even though 90 beats per minute is below a population threshold of 100 beats per minute, the clinician may consider a change from 50 to 90 beats per minute to be a substantial change for a patient with a history of rigorous athletic training. The biological sensor 102 used by patient (B) can detect that the patient is at rest utilizing, for example, the motion sensor 418 depicted in FIG. 4. The chart of patient (B) may also include information indicating the last time patient (B) was measured at 50 beats per minute.

In one embodiment, the sensor management system 304 (or the computing device 202) can be configured to determine from the chart of patient (B) the threshold of 90 beats per minute and thereafter monitor patient (B) for unexpected changes. The sensor management system 304 (or the computing device 202) can also be configured to detect unexpected rapid changes in pulse rate in a relatively short period (e.g., 48 hours or less). Further, the sensor management system 304 (or the computing device 202) can also be configured to detect a trend in the pulse rate of patient (B) (e.g., an upward trend in pulse rate over weeks or months).

Turning now to patient (C), given the normative condition of patient (C) averages at 105 beats per minute, which is high (likely due to illness, e.g., hypertension), the clinician may consider an adverse biological condition to begin at 100 beats per minute when patient (C) is at rest. The clinician may have set a threshold below the normative condition as a result of the clinician prescribing medication to reduce hypertension in patient 100. Such prescription may reduce the pulse rate of the patient by, for example, 15% (e.g., ~90 beats per minute). The clinician can enter the prescribed medication in the chart of patient 100 which is accessible to the sensor management system 304 (or the computing device 202). Although FIG. 7B shows a normative condition of 105 beats per minute, the sensor management system 304 (or the computing device 202) can be configured to recognize an adjusted normative condition of 90 beats per minute while patient 100 is using the hypertension medication.

In one embodiment, the sensor management system 304 (or the computing device 202) can be configured to determine from the chart of patient (C) the threshold of 100 beats per minute and thereafter monitor patient (C) for unexpected changes. The sensor management system 304 (or the computing device 202) can also be configured to detect unexpected rapid changes in pulse rate in a relatively short period (e.g., 48 hours or less). Further, the sensor management system 304 (or the computing device 202) can also be configured to detect a trend in the pulse rate of patient (C) (e.g., an upward trend in pulse rate over weeks or months).

The foregoing embodiments for determining normative conditions and thresholds of a patient as shown in FIGS. 7A-7D can also be used for other vital signs (e.g., blood pressure, respiration rate), as well as to other biological functions that can be measured for a patient (e.g., red cell count, SpO2, glucose levels in the blood, electrocardiogram measurements, and so on). Additionally, the sensor management system 304 (or the computing device 202) can be configured to analyze sensor data of more than one biological function at a time to assess normative conditions and thresholds rather than relying on a single biological function. The sensor management system 304 (or the computing device 202) can, for example, correlate one type of biological sensor data (e.g., pulse rate) with another type of biological sensor data (e.g., blood pressure) to determine a normative condition and/or threshold. In this manner, the sensor management system 304 (or the computing device 202) can perform a more holistic analysis of the patient's sensor data.

It is further noted that the normative conditions and the thresholds of FIGS. 7A-7D can have a temporal component. That is, a normative condition may be considered normative only for a period of time either by instructions from the clinician, medical protocols and/or other medical conditions associated with the patient 100 that can be determined by the sensor management system 304 (or the computing device 202). In one embodiment, a threshold can be set for a specific time period. For example, the sensor management system 304 (or the computing device 202) can detect when a drug therapy has begun and when it ends by obtaining information from the chart of the patient 100. In an embodiment, the sensor management system 304 (or the computing device 202) can be configured to change normative conditions and corresponding thresholds upon expiration of such periods.

In another embodiment, the sensor management system 304 (or the computing device 202) can be adapted to use ranges of the normative conditions and thresholds shown in FIGS. 7A-7D. That is, a normative condition and/or a threshold can have a range having an upper and lower limit. In another embodiment, more than one normative condition and more than one threshold can be used to identify different biological conditions that may arise in a patient as the patient's sensor data shows measurements drifting in one direction or another. In yet another embodiment, the sensor management system 304 (or the computing device 202) can be adapted to detect sensor data trends that it can use to predict future outcomes before they occur. A sensor data trend can, for example, identify a specific course that measurements may be taking, which in turn can provide the sensor management system 304 (or the computing device 202) a projected trajectory and time when an adverse condition may occur. In another embodiment, the sensor management system 304 (or the computing device 202) can be adapted to detect erratic changes in sensor data. Such changes can be flagged as a problem with the biological sensors 102 (e.g., a malfunction) and/or biological issues that may need to be addressed.

It is further noted that algorithms for detecting biological conditions can be generated by the sensor management system 304 (or the computing device 202). In one embodiment, for example, the sensor management system 304 (or the computing device 202) can be configured to generate a script or software program that emulates a specific medical protocol used for detecting biological conditions associated with an illness of the patient, an adverse reaction to a drug therapy being applied to the patient, or some other biological condition to be monitored. The script or software can be generated by the sensor management system 304 (or the computing device 202) can, for example, detect trends, detect when sensor measurements exceed thresholds, detect erratic or rapid changes, applying hysteresis to sensor measurements to filter out short bursts of anomalous readings, detect malfunctions in the biological sensor 102, and so on. So long as the biological sensor 102 has the computing resources, any algorithm of any complexity can be supplied to the biological sensor 102. For example, a script or software can determine how often a patient 100 is sensed. Patients that are healthy, for instance, may be sensed less frequently thereby saving battery power of the sensor 102. Patients that may have a condition may have a script or software that's more aggressive on readings.

The script or software can comprise instructions executable by the biological sensor 102, or macro instructions that can be translated (compiled) by the biological sensor 102 into executable instructions. Each algorithm can be given a version which can be sent to the biological sensors 102 for version tracking. As medical protocols change, the sensor management system 304 (or the computing device 202) can query biological sensors 102 for versions and download new algorithmic versions when a version used by the biological sensors 102 is out-of-date. The sensor management system 304 (or the computing device 202) can also be configured to provide new algorithmic versions to the biological sensors 102 that are pre-programmed with a certain algorithmic version that may be out-of-date.

Referring back to FIG. 6, the foregoing embodiments illustrate ways to process historical sensor data obtained at step 610 (and chart information if available for the patient 100) to determine normative conditions and/or thresholds at step 614. It is noted that chart information may be electronically stored by the sensor management system 304, the computing device 202, or other storage systems accessible by the sensor management system 304 and/or the computing device 202.

Referring back to step 608, if the sensor management system 304 (or the computing device 202) detects that historical sensor data is not available for the patient 100, the sensor management system 304 (or the computing device 202) can proceed to step 612. At this step, the sensor management system 304 (or the computing device 202) can collect sensor data from the new sensor until sufficient sensor data is available to determine normative conditions and/or thresholds for the patient according to the sensor data (and chart information if available for the patient).

Referring now to step 614, once the normative condition(s) and/or threshold(s) have been determined according to historical sensor data obtained at step 610, the sensor management system 304 (or the computing device 202) can proceed to step 616 and generate provisioning information for the new biological sensor 102 detected at step 606. The provisioning information can include, among other things, one or more normative conditions, one or more thresholds, one or more algorithms (if the biological sensor 102 is not pre-programmed or has an out-of-date algorithm), a most recent history of sensor data measurements (e.g., measurements performed in the last hour), identification information of the patient 100, a last known location of the patient, certain chart information relating to the patient (e.g., illness type, drug therapy type, date of surgery, type of surgery, etc.), and so on. The amount of information included in the provisioning information generated at step 616 can depend on the memory resources of the biological sensor 102, the function of the biological sensor 102, usage preferences of the clinician (e.g., ability to recall a short history of sensor data), and so forth.

Once provisioning information has been generated, the sensor management system 304 (or the computing device 202) can proceed to step 618 and provide the provisioning information to the biological sensor 102. The biological sensor 102 can then begin to monitor one or more biological conditions of the patient at step 620. Such conditions can be determined from an algorithm provided to (or pre-programmed in) the biological sensor 102. In one embodiment, the algorithm can detect that sensor measurements exceed a specific threshold or a threshold range. In other embodiments, the algorithm can detect sensor data trends, erratic or rapid changes, and/or predict future outcomes. At step 622, the biological sensor 102 can provide the sensor management system 304 (or the computing device 202) information relating to detection of biological conditions monitored by the biological sensor 102, including without limitations, sensor data measurements, measurements exceeding a specific threshold or threshold range, trends in sensor data, erratic or rapid changes in sensor data, predicted adverse biological conditions, and so on. Such information can be provided to the sensor management system 304 (or the computing device 202) with time stamps (e.g., time of day: hours/minutes/second, date: month/day/year).

If trend information is not provided at step 622, the sensor management system 304 (or the computing device 202) can be configured at step 624 to analyze the sensor data to detect trends, erratic or rapid changes and so on. The sensor management system 304 (or the computing device 202) can also be configured to report a status of biological conditions of the patient 100 to clinicians. For example, if no adverse biological conditions have been detected, the clinician can be provided a history of the measured sensor data in a status report that indicates no adverse biological conditions were detected. If, on the other hand, one or more adverse biological conditions were detected, the clinician can be provided with a detailed report that includes sensor data that exceeded one or more thresholds, time stamp information associated with the sensor data, and so on. The sensor management system 304 (or the computing device 202) can also be configured to provide trend information if available. If adverse biological conditions are not presently detected, but trend information predicts a future adverse condition, then the sensor management system 304 (or the computing device 202) can provide such information to the clinician to enable the clinician to take preemptive action to avoid such adverse condition from occurring.

At steps 626-628, the sensor management system 304 (or the computing device 202) can monitor placement of another new biological sensor 102 on the patient 100. If another new biological sensor 102 is not detected, the sensor management system 304 (or the computing device 202) can proceed to step 620 and repeat the processes previously described. If, however, another new biological sensor 102 is detected, the sensor management system 304 (or the computing device 202) can proceed to step 628 to obtain a model number, serial number or other identification data from the new biological sensor 102 to determine if the new sensor is of the same type and function as the previous sensor. Additionally, the sensor management system 304 (or the computing device 202) can obtain patient identification data from the new biological sensor 102, which the biological sensor may have obtained from a wrist band of the patient including an RFID, the biometric sensor 409 of FIG. 4, or by patient information provided to the biological sensor 102 by way of the computing device 202 of the clinician as depicted in FIG. 2B.

If the new biological sensor 102 is the same as the previous sensor and has been coupled to the same patient, then the sensor management system 304 (or the computing device 202) can proceed to step 630 and determine if the new biological sensor 102 is a replacement for the previous same sensor. If the new biological sensor 102 is not the same as the previous sensor, a determination can be made whether the new sensor is a replacement sensor by the sensor management system 304 (or the computing device 202) by obtaining information from the new sensor indicating it is a replacement sensor, determining that the new sensor does not have in its memory a patient identifier, or by receiving input data from, for example, the computing device 202 initiated by, for example, a clinician, indicating it is a replacement sensor. If such information is not provided by the new sensor or the computing device 202, and/or the new sensor has been coupled to a different patient, then the sensor management system 304 (or the computing device 202) can proceed to step 606 and perform the same sequence of steps previously described for the same patient if the new sensor is associated with the same patient, or for a different patient in which case a new record would be created in the databases 306 or other storage resources of the sensor management system 304 (or the computing device 202).

Referring back to step 630, in one embodiment, the sensor management system 304 (or the computing device 202) can determine that the new biological sensor 102 is replacing the previous sensor upon receiving a message from the computing device 202 of the clinician as noted above. The message can indicate which sensor is being replaced by identifying the serial number of the previous sensor in the message and identifying the serial number of the new sensor. In another embodiment, the sensor management system 304 (or the computing device 202) can determine that the new biological sensor 102 is replacing a previous sensor based on the new biological sensor 102 not being programmed with a patient identifier. In yet another embodiment, the sensor management system 304 (or the computing device 202) can determine that the new biological sensor 102 is replacing a previous sensor based on an understanding that two of the same type of sensors for the same patient is not common practice for the clinician and in such instances detecting a new sensor represents a replacement procedure undertaken by the clinician. It should be noted that there may be instances when a new biological sensor of the same type will not be considered a replacement sensor. For example, a clinician may wish to use the same sensor in multiple locations of a patient's body. Such exceptions can be noted by the clinician using the computing device 202. In yet another embodiment, the sensor management system 304 (or the computing device 202) can determine that the new biological sensor 102 is replacing a previous sensor based on a utilization period of the previous sensor expiring or detecting that the previous sensor is damaged or malfunctioning. Other suitable detection methods for determining a replacement of sensors are contemplated by the subject disclosure.

Once a replacement event is detected, the sensor management system 304 (or the computing device 202) can proceed to step 634 and decommission the previous sensor. The decommissioning process can represent noting in a record of the patient 100 that the serial number of the biological sensor 102 being replaced has been decommissioned. Once the sensor is decommissioned, the sensor management system 304 (or the computing device 202) can be configured to ignore sensor data from the decommissioned sensor if such data were to be provided. The sensor management system 304 (or the computing device 202) can then proceed to step 610 to obtain historical sensor data produced by the previous sensor and any predecessor sensors. The sensor management system 304 (or the computing device 202) can then proceed to perform subsequent steps as previously described. The sensor management system 304 (or the computing device 202) can be provisioned to provide the new biological sensor 102 some or all of the obtained historical sensor data of one or more previous sensors for local storage, enabling retrieval by the computing device 202 if desired. It is further noted that the steps of method 600 can be adapted so that the sensors 102 (new or old) can proactively (e.g., without polling by the sensor management system 304 or the computing device 202) initiate communications with the sensor management system 304 or the computing device 202 and provide updates as needed. Such a process can be pre-programmed into the sensors 102 or a script or software can be provided to the sensors 102 by the sensor management system 304 or the computing device 202 to enable a proactive communication process.

It will be appreciated that the foregoing embodiments can be implemented and executed in whole or in part by the biological sensor 102, the computing device 202, the sensor management system 304, or any combination thereof. It is further appreciated that the biological sensor 102, the computing device 202, the sensor management system 304, or any combination thereof, can be adapted to in whole or in part to use one or more signal profiles for detecting a biological condition. The signal profiles can be, for example, time domain or frequency domain profiles, which can be used to detect biological conditions. Additionally, a signal profile can be specific to each user. That is, a signal profile can be determined for a specific patient 100 according historical sensor data (e.g., EKG data, spectrometer data, etc.) collected from the patient 100. Accordingly, a clinician 101 can configure a biological sensor 102 to be tailored to the patient's 100 clinical history rather than utilizing a signal profile applied to the general population.

While for purposes of simplicity of explanation, the respective processes are shown and described as a series of blocks in FIG. 6, it is to be understood and appreciated that the claimed subject matter is not limited by the order of the blocks, as some blocks may occur in different orders and/or concurrently with other blocks from what is depicted and described herein. Moreover, not all illustrated blocks may be required to implement the methods described herein.

Upon reviewing the aforementioned embodiments, it would be evident to an artisan with ordinary skill in the art that said embodiments can be modified, reduced, or enhanced without departing from the scope of the claims described below. For example, method 600 can be adapted so that the sensor management system 304 or the computing device 202 tracks GPS coordinates of patients 100 using a location receiver 416 of the biological sensor 102. GPS data can be used, for example, to analyze the activities of the patient 100 and in some instances such activities may be used to analyze the sensor data. For example, the GPS coordinate data may indicate that a patient was walking or jogging. Such information can be used to distinguish sensor data taken at rest versus other activities. Orientation and motion data produced by the orientation sensor 420 and motion sensor 418 can be used to more accurately assess a 3D position of the patient 100, and a level of activity of the patient 100 (e.g., lying down, running in place, sitting, etc.). By further refining the activity of the patient 100 with 3D positioning information, the sensor management system 304 can more precisely analyze sensor data obtained from one or more biological sensors 102 coupled to a patient 100.

It should be understood that devices described in the exemplary embodiments can be in communication with each other via various wireless and/or wired methodologies. The methodologies can be links that are described as coupled, connected and so forth, which can include unidirectional and/or bidirectional communication over wireless paths and/or wired paths that utilize one or more of various protocols or methodologies, where the coupling and/or connection can be direct (e.g., no intervening processing device) and/or indirect (e.g., an intermediary processing device such as a router).

Figure 8A:
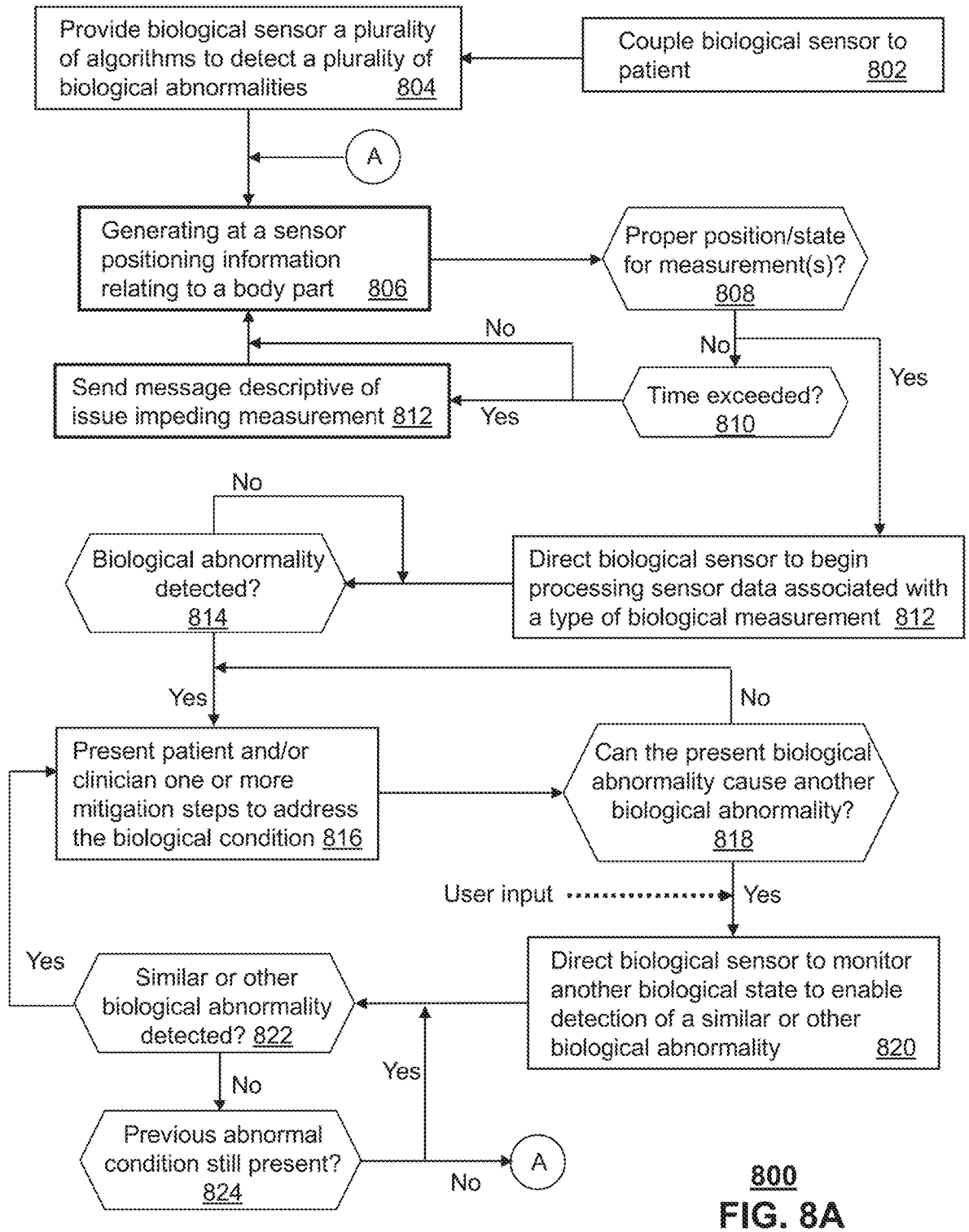
FIG. 8A is a block diagram illustrating an example, non-limiting embodiment of a method for monitoring a plurality of biological states in accordance with various aspects of the subject disclosure described herein.
Figure 8B:
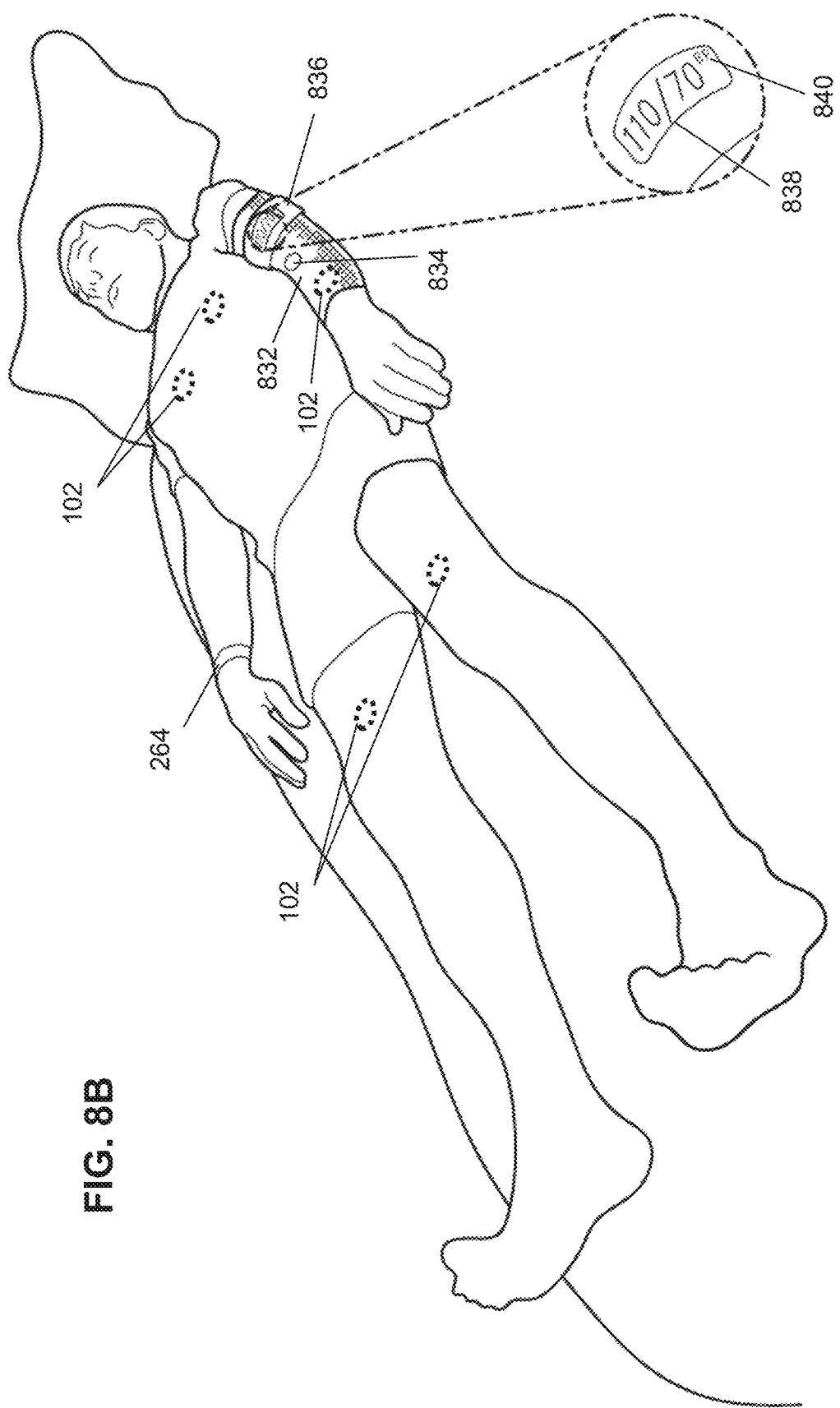
FIGS. 8B-8E are block diagrams illustrating example, non-limiting embodiments for coupling sensors to body parts in accordance with various aspects of the subject disclosure described herein.
Figure 8C:
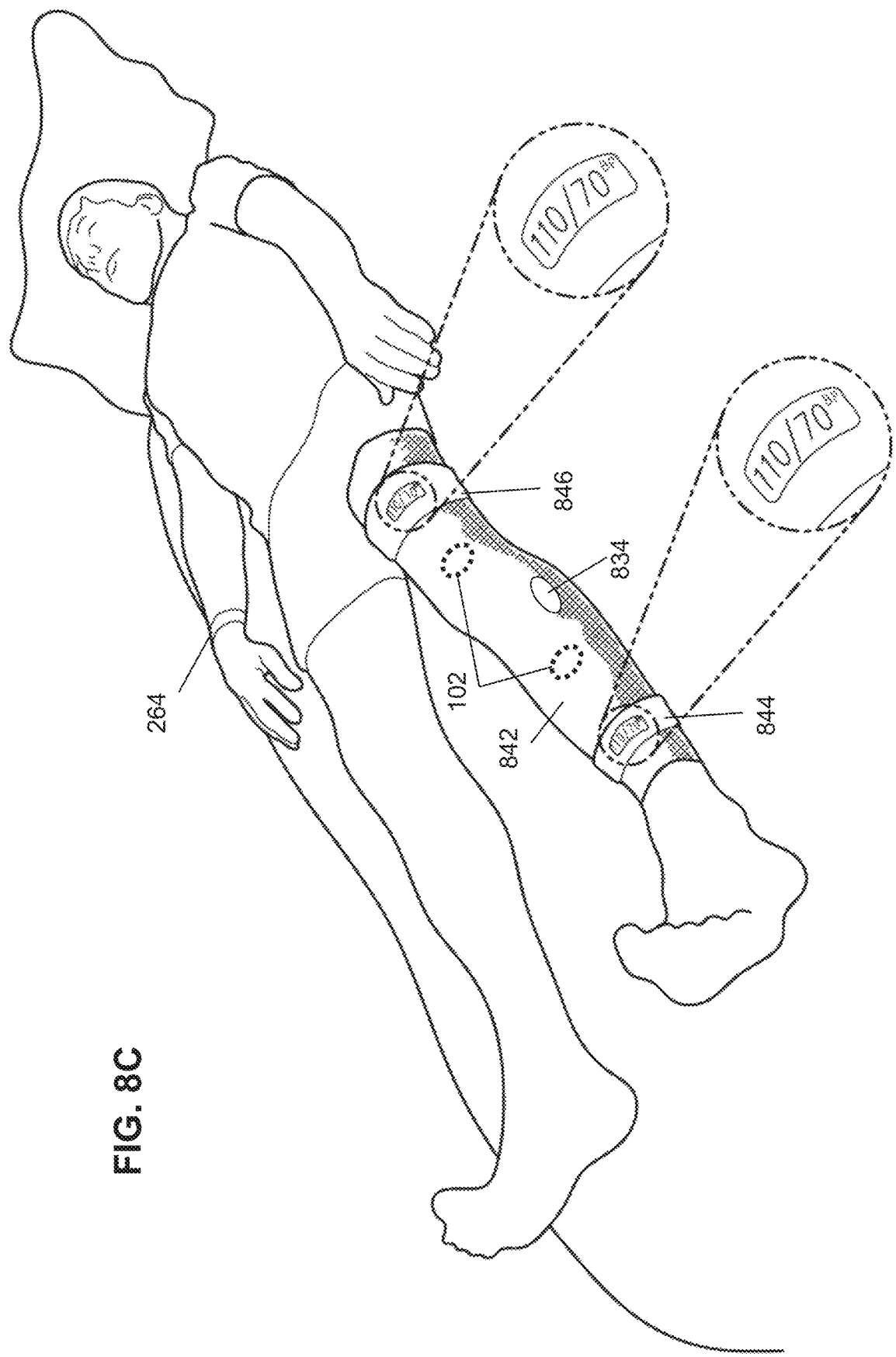
Figure 8D:
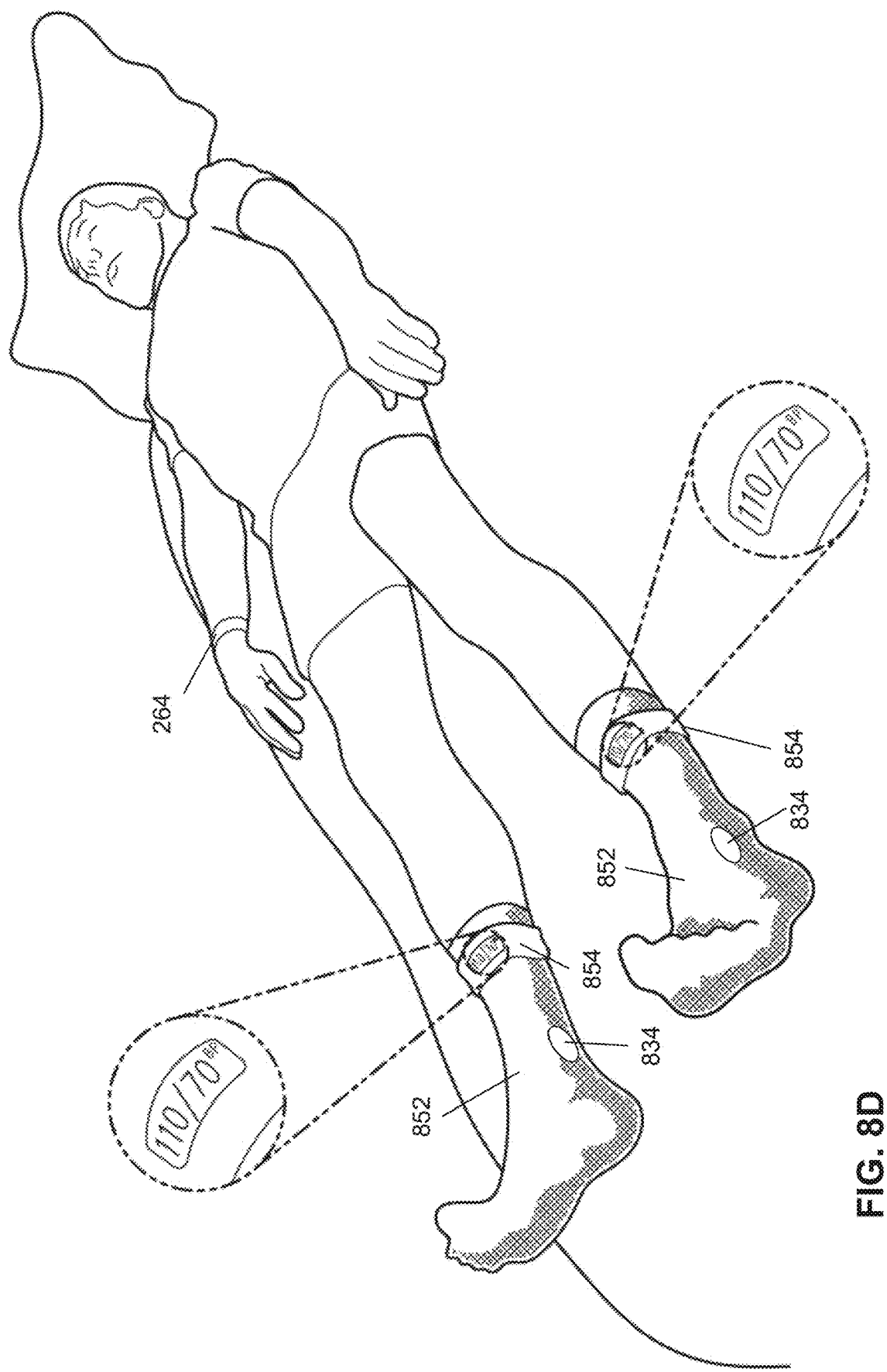
Figure 8E:
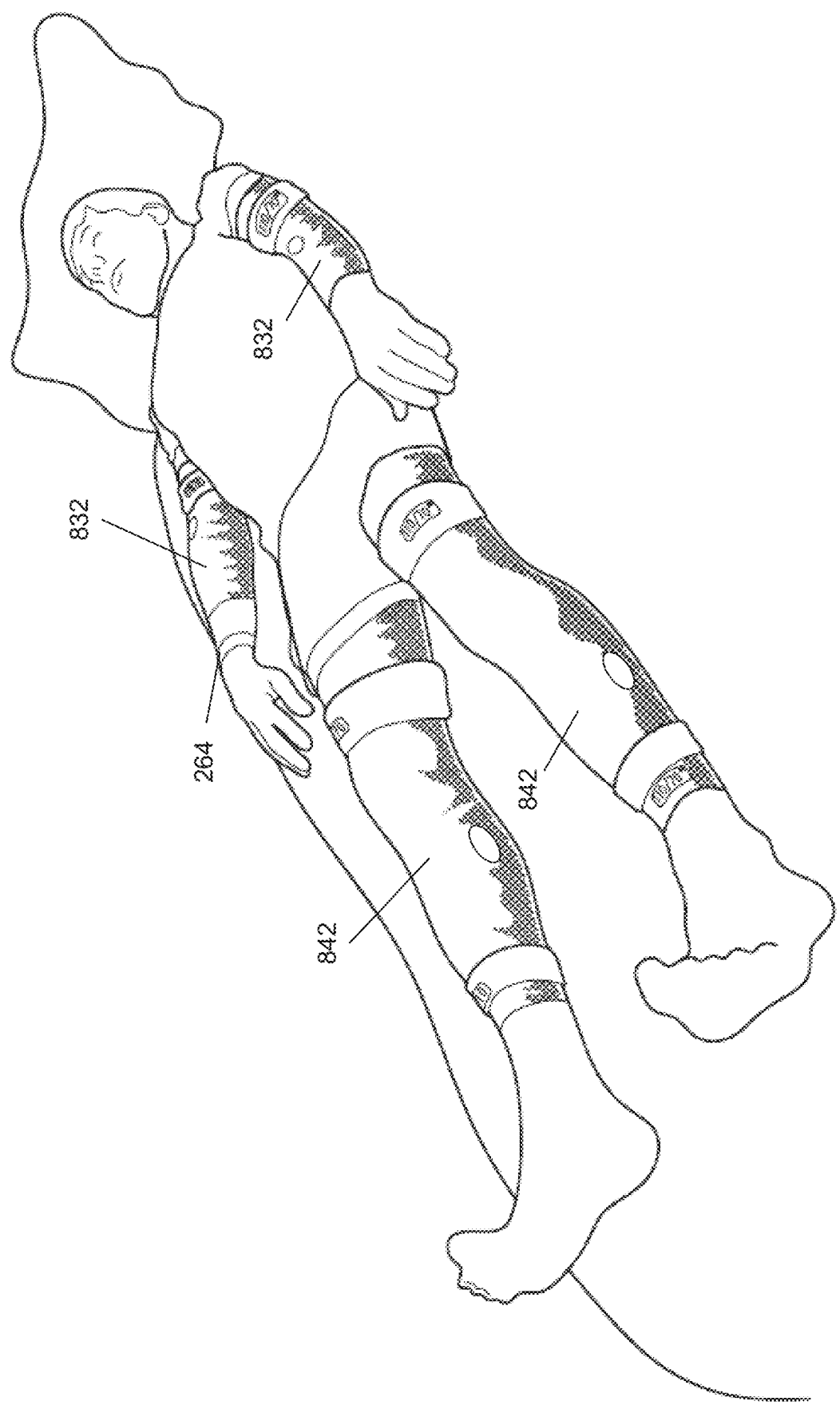

Now turning to FIG. 8A, a block diagram illustrating an example, non-limiting embodiment of a method 800 for monitoring a plurality of biological states in accordance with various aspects of the subject disclosure is shown. Method 800 can be performed with one or more individual biological sensors 102 or one or more biological sensors 102 integrated in a material that couples in whole or in part to a body part of a patient 100 as illustrated in FIGS. 8B-8E. For example, an embodiment of an arm sleeve 832 is depicted in FIG. 8B, an embodiment of a leg sleeve 842 is depicted in FIG. 8C, and an embodiment of a sock 852 is depicted in FIG. 8D. Some of the biological sensors 102 shown in the arm sleeve 832, the leg sleeve 842, and/or the sock 852 can be on the back side or other locations not visible in FIGS. 8B-8E. In some embodiments, multiple instances of the embodiments of FIGS. 8B-8E can be used in different body parts or segments of a patient 100 to perform differential measurements. For example, multiple instances of a sock 852 can be used as depicted in FIG. 8D. Similarly, multiple instances of the arm sleeve 832 and leg sleeve 842 can be used as depicted in FIG. 8E.

Each biological sensor 102 integrated in arm sleeve 832, leg sleeve 842 and/or sock 852 can be powered from a local power supply 414 that is integrated in the arm sleeve 832, leg sleeve 842 and/or sock 852. The local power supply 414 can be as shown in FIG. 4 (utilizing batteries or some other form of energy harvesting, e.g., kinetic energy, body heat, etc.). Alternatively, or in combination with a local power supply, each biological sensor 102 integrated in arm sleeve 832, leg sleeve 842 and/or sock 852 can be powered from a tethered connection to a DC power line not shown in FIGS. 8B-8E. The arm sleeve 832, the leg sleeve 842, and/or the sock 852 can be constructed of an elastic material such as nylon, cotton, wool, silk, or combinations thereof. In some embodiments, the arm sleeve 832, the leg sleeve 842, and/or the sock 852 can be split in half resulting in two ends that can be attachable or detachable with Velcro® or other suitable materials which enable the arm sleeve 832, the leg sleeve 842, and/or the sock 852 to be wrapped around certain body segments. The arm sleeve 832, the leg sleeve 842, and/or the sock 852 can also include an opening 834, which can be used by a clinician to extract blood samples, insert an IV catheter, perform measurements or otherwise gain access to the antecubital fossa. Openings can be placed in other locations of the arm sleeve 832, the leg sleeve 842, and/or the sock 852 for similar or different purposes.

In some embodiments, the arm sleeve 832, the leg sleeve 842, and/or the sock 852 can each have an integrated blood pressure measurement system 836, 844, 846, 854 for performing blood pressure measurements. The biological sensors 102 located in different areas of the arm sleeve 832, the leg sleeve 842, and/or the sock 852 can be configured to make direct or indirect contact with the skin of the patient 100 to measure different biological states of a patient 100 (e.g., blood pressure, temperature sensor, perspiration sensor, pulse rate sensor, glucose level sensor, SpO2 sensor, ECG/EKG, etc.) and/or to apply drug delivery utilizing the drug delivery system 408 described earlier in relation to FIG. 4. The embedded blood pressure measurement systems 836, 844, 846, 854 (and/or other biological sensors 102 integrated in the arm sleeve 832, the leg sleeve 842, and/or the sock 852) can be coupled to a display 405 (e.g., LED display) that provides a visual reading of a biological measurement such as a blood pressure reading 838 (or other readings, e.g., temperature, pulse rate, etc.), which can be distinguished from other measurements with an indicator 840 (e.g., "BP" in the upper right corner) as illustrated in FIG. 8B. The controller 406 of the one or more biological sensor(s) 102 integrated in the arm sleeve 832, the leg sleeve 842, and/or the sock 852 can be configured to present different biological measurements (e.g., temperature, SpO2, etc.) by changing the indicator 840 on the upper right of the display 405.

The one or more biological sensors 102 included in the arm sleeve 832, the leg sleeve 842, and/or the sock 852 can also be configured to communicate (via the transceiver 102—see FIG. 4) by a tethered or wireless interface with each other and/or other biological sensors 102 not coupled or integrated in the arm sleeve 832, the leg sleeve 842, and/or the sock 852. These other biological sensors 102 can include, for example, biological sensors 102 coupled to the chest and thighs of the patient 100 as depicted in FIG. 8B. The patient 100 can be provided a wristband 264 such as depicted in FIG. 2M, which can be equipped with a radio frequency identification (RFID) tag or other suitable communication device. The wristband 264 can include information about the patient 100 (e.g., name, age, medical records, etc.), which the one or more biological sensors 102 included in the arm sleeve 832, the leg sleeve 842, and/or the sock 852 can be configured to wirelessly obtain from the wristband 264.

With the foregoing embodiments in mind for FIGS. 8B-8E, method 800 can begin at step 802 where a clinician 101 places a biological sensor 102 on a patient 100 as shown in FIG. 2A, or inserts on a patient's limb (or wraps around a patient's limb with Velcro®, belt(s) or other implements) an arm sleeve 832, leg sleeve 842, and/or sock 852 having one or more integrated biological sensors 102 as depicted in FIGS. 8B-8E (some biological sensors 102 may not be visible). Whether used individually or integrated in an arm sleeve 832, leg sleeve 842, and/or sock 852, the biological sensors 102 can be provisioned as described earlier by the flowchart of FIG. 6. Once provisioned, the biological sensors 102 can be configured to monitor a plurality of biological states (e.g., temperature, perspiration, pulse rate, blood pressure, respiration rate, glucose levels in the blood, SpO2, ECG/EKG, etc.).

In one embodiment, individual biological sensors 102 and/or biological sensors 102 integrated in the arm sleeve 832, the leg sleeve 842, and/or the sock 852 can be provided a plurality of algorithms at step 804 for detecting a corresponding plurality of biological conditions (e.g., abnormal blood pressure, abnormal glucose, heart attack, arrhythmia, abnormal EKG, etc.). The algorithms can be provided to the biological sensor(s) 102 by the computing device 202 or sensor management system 304 over a wired or wireless interface. In other embodiments, the biological sensor(s) 102 can be preconfigured with the algorithms at a time when the biological sensor(s) 102 are manufactured. The plurality of algorithms can be used to process sensor data generated by different sensors of the biological sensor(s) 102 to detect one or more biological conditions.

The individual biological sensors 102 and/or those integrated in the arm sleeve 832, the leg sleeve 842, and/or the sock 852 can be configured to generate positioning information for each of one or more body parts (or segments) such as, for example, an arm, leg, back, hip, or other body part. At step 806, positioning information can be generated from multiple biological sensors 102, each located at a different segment of a patient's body. For example, the arm sleeve 832 may have one biological sensor 102 (measuring, for example, blood pressure) located at a bicep and another biological sensor 102 located at the forearm of the patient 100 for performing a different measurement (e.g., pulse rate, temperature, etc.). The biological sensor 102 located at the bicep can provide positioning information relating to the bicep, while the biological sensor 102 located at the forearm can provide positioning information relating to the forearm.

Each biological sensor 102 can include a motion sensor 418 (see FIG. 4) which can sense motion in three-dimensional space and thereby provide positioning information in relation to a segment of a body part where the biological sensor 102 is located. The motion sensor 418 can include a gyroscope and an accelerometer which together can be used to generate positioning information in three-dimensional space. In some embodiments, the biological sensors 102 may also include an orientation sensor 420 (see FIG. 4) to generate orientation information (northwest, southwest, etc.) of a body segment. The orientation information can be part of the positioning information.

The biological sensors 102 located at the bicep and forearm can be configured to share positioning information with each other wirelessly or by a tethered interface. Similarly, biological sensors 102 can be placed at different segments of the leg sleeve 842 or sock 852. From the combined positioning information of the bicep and forearm one or both biological sensors 102 can determine that an arm of the patient 100 is at a rest position, in motion, is bent, is not bent, is not held upwards, is held upwards, or has some other orientation or motion. Similar determinations can be made by biological sensors 102 of the leg sleeve 842, and sock 852 by sharing position information between biological sensors 102 integrated therein. The combined positioning information can be used by the biological sensors 102 to determine at step 808 whether the arm of the patient 100 is in a desirable position and at a state of rest to perform, for example, a blood pressure measurement and/or pulse rate measurement.

The biological sensors 102 can also share biological states with each other. For example, a biological sensor 102 that measures pulse rate can share its measurements with a biological sensor 102 in the blood pressure measurement system 836 to determine if the patient 100 is in a desirable biological state to perform a blood pressure measurement. For example, suppose the biological sensor 102 performing the pulse rate measurement has in its memory banks the normal pulse rate of the patient 100, which is 100 beats per minute (as shown in FIG. 7D). Further suppose that the pulse rate presently measured is 120 beats per minute. The pulse rate information provided to the biological sensor 102 that measures blood pressure by the biological sensor 102 performing the pulse rate measurement can further identify that the pulse rate is 20 beats above the normal pulse rate threshold of the patient 100. Alternatively, the biological sensor 102 that measures blood pressure can wirelessly obtain the normal pulse rate threshold of the patient 100 from information stored in the wristband 264, and thereby determine that the pulse rate of the patient 100 is 20 beats above normal.

Accordingly, if the arm, leg, or foot is not at rest, pointing upwards, bent, or in an otherwise undesirable position, and/or a related biological state of the patient 100 is undesirable (e.g., pulse rate above normative threshold), then the biological sensor 102 that performs blood pressure measurements can be configured at step 808 to postpone the measurement until the patient 100 stabilizes, is in a rest position, has his/her arm, leg, foot in a desirable position, and/or the related biological state is desirable. When a measurement is postponed, the biological sensor 102 can be configured to initiate a timer at step 810 to determine the duration of postponement. The biological sensor 102 can be configured with a timeout period (e.g., 3 mins, 5 mins, 15 mins, 30 mins, 1 hr, 2 hrs, etc.), which can be provided by the computing device 202 of the clinician 101 or the sensor management system 304.

The timeout period can be chosen according to the biological state that needs to be measured. For example, it may be desirable that a blood pressure reading not be postponed more than 1 hour based on a medical history of the patient, which can be obtained from records of the patient stored in the wristband 264, or provided by the computing device 202, workstation 266 or sensor management system 304. If the patient 100 does not have his/her arm, leg, or foot at rest and in desirable orientation and/or one or more related biological states are not desirable for more than an hour, then the timer of the biological sensor 102 can trigger at step 810 and generate a message at step 812 descriptive of a positioning and/or biological state issue. The message can be presented at the display 405 of the biological sensor 102 as depicted in FIGS. 2L and 8B-8E. The message presented can be an error code, text message descriptive of the issue, or some other form of a displayable indicator. Alternatively, or in combination, the biological sensor 102 can be configured to transmit the message over a tethered or wireless interface to the computing device 202, workstation 266, or sensor management system 304.

It will be appreciated that the sharing of positioning information and biological states between biological sensors 102 can be performed for any combination of biological sensors 102. Sharing positioning information and biological states can be used by each biological sensor 102 to determine when measuring a biological state will provide accurate or inaccurate measurements. Such a determination can be useful for reducing false-positive detection of adverse biological conditions.

Referring back to step 810, when the position of the patient 100 and/or related biological state(s) will not result in an inaccurate measurement of another biological state, the biological sensor 102 can be configured at step 812 to begin monitoring the biological state (e.g., temperature, blood pressure, SpO2, etc.) of the patient 100 for detection at step 814 of a biological condition that can result in a biological abnormality (e.g., fever, hypertension, hypoxemia, etc.). Steps 812-814 can be initiated by the biological sensor 102 responsive to the computing device 202 or the sensor management system 304 providing instructions to the biological sensor 102 responsive to receiving information (e.g., positioning information and/or related biological states) from one or more biological sensors 102 coupled to the patient 100 that enable the computing device 202 or the sensor management system 304 to determine that the patient 100 is in a desirable state of rest, position, and/or related biological state(s). Alternatively, the biological sensor 102 can be configured to initiate steps 812-814 once the biological sensor 102 has made its own determination from information provided by other biological sensors 102 (e.g., positioning information and/or related biological states) that the patient 100 is in a desirable state of rest, position, and/or related biological state(s).

Once the biological sensor 102 begins to process sensor data at step 812 responsive to detecting a favorable position and/or favorable related biological state(s), an adverse biological condition can be detected at step 814 according to one or more thresholds or signal profiles programmed into the biological sensor 102, which enable detection of a biological abnormality such as, for example, an abnormal temperature of the patient 100, an abnormal heart rate of the patient 100, an abnormal blood pressure of the patient 100, an abnormal SpO2 reading of the patient 100, an abnormal glucose level of the patient 100, an abnormal ECG/EKG reading, and so on. Provisioning a biological sensor 102 with thresholds and/or signal profiles which may be specific to a patient 100 was described earlier in relation to FIGS. 6 and 7A-7D.

If an adverse biological condition is detected at step 814, the biological sensor 102 can be configured at step 816 to present the patient 100 and/or clinician 101 with one or more mitigation steps to address the biological condition. The mitigation steps presented can be procedures and/or treatments which can be displayed at the biological sensor 102, on a wristband 264, on a display device 265 affixed to a wall or other fixture, at the computing device 202, or at a workstation 266 as previously described according to the illustrations of FIGS. 2L-2P. If at step 818 a determination is made that the biological condition can potentially give rise to another biological condition, the biological sensor 102 can be configured at step 820 to monitor another biological condition. The determination that another biological condition can result from the occurrence of the first biological condition can be made by an algorithm executed by the biological sensor 102, an algorithm executed by the computing device 202, an algorithm executed by the sensor management system 304, combinations thereof, or according to input provided by the clinician 101 via the computing device 202, the sensor management system 304, or the workstation 266.

Algorithms can be used to predict a potential occurrence of a subsequent biological condition based on a protocol defined by health professionals or institutions, and/or a medical history of the patient 100. For example, protocols may exist for predicting side effects from an onset of a fever, a heart attack, a glucose imbalance, hypertension, and so on. Such protocols can be adapted to a patient's medical history. For example, a patient 100 may have a medical history showing a recurring pattern such that when the patient 100 experiences one biological condition an alternate biological condition has a tendency to occur. A clinician or system can adapt standard protocols in whole or in part according to the medical history of the patient 100.

In other embodiments, a clinician 101 can input a request to monitor a new biological condition in response to a first biological condition. The clinician 101 can enter this request by way of a user interface of the computing device 202, the sensor management system 304, or the workstation 266. Any of the foregoing devices used by the clinician 101 can be configured to instruct the biological sensor 102 at step 820 to process sensor data of a different biological state to monitor for a potential occurrence of a similar or different biological condition at step 822.

It will be appreciated that the biological sensor 102 can be configured to transition from monitoring one biological condition to another in any order. The sequence or order of biological conditions monitored may be defined by standard or customized protocol(s) referred to earlier. Any of these protocols can be executed in whole or in part by the biological sensor 102, the computing device 202, the sensor management system 304, or any combinations thereof. Each protocol can define an order of processing biological states (e.g., temperature→blood pressure→EKG) and corresponding biological conditions (e.g., fever→high or low blood pressure heart conditions).

Although the flowchart of FIG. 8A shows the biological sensor 102 being configured to monitor one biological condition after another, such illustrations are non-limiting. For example, method 800 can be adapted to configure the biological sensor 102 to simultaneously monitor combinations of biological states (e.g., temperature and blood pressure) and corresponding biological conditions (e.g., fever and abnormal blood pressure). Method 800 can be further adapted to detect one or more abnormalities and direct the biological sensor 102 to monitor other combinations of biological states and corresponding biological conditions. Method 800 can also be adapted to continue monitoring one or more biological states and one or more biological conditions previously detected while contemporaneously monitoring one or more new biological states and corresponding one or more biological conditions.

In other embodiments, method 800 can be adapted to track and manage combinations of biological sensors 102 and configure each biological sensor 102 to monitor one or more biological states and corresponding biological conditions. In this embodiment, method 800 can be adapted to detect one or more abnormalities from combinations of biological sensors 102 and direct one or more of the biological sensors 102 to monitor one or more other biological states and corresponding one or more other biological conditions. In one embodiment, the coordination and control of multiple biological sensors 102 can be performed by the computing device 202, the sensor management system 304, or the workstation 266. In another embodiment, multiple biological sensors 102 can be configured to form a wireless network amongst themselves and coordinate monitoring and detection of one or more biological conditions according to a protocol. In this configuration, the coordination can be based on a master-slave arrangement (i.e., a master biological sensor coordinating slave biological sensors), or in another arrangement, the multiple biological sensors 102 can form a mesh network where coordination is performed by a cooperative exchange of messages and sensor data between the biological sensors 102 to execute one or more protocols.

It will be further appreciated that method 800 can be adapted to assert one or more timers as previously described in the illustration of FIG. 2Q when one or more biological conditions are detected. Additionally, one or more timers can be asserted while monitoring one or more new biological states and corresponding biological conditions. The timers can be presented as previously illustrated in FIGS. 2L-2P.

Referring back to step 822, when a subsequent biological condition is detected, a presentation of mitigation steps can be provided to the patient 100 and/or clinician 101 as previously described. If, however, a subsequent biological condition is not detected at step 822, and a previous biological condition is determined to no longer be present at step 824, then the biological sensor 102 can be configured to restart the monitoring process from step 806 as previously described. The transition from step 824 to step 806 can occur in instances, for example, when the mitigation steps of step 816 achieve a goal of eradicating the biological condition previously detected at step 814.

It will be appreciated that the illustrations provided in the flowchart of method 800 are non-limiting. For example, method 800 can be adapted so that when a first biological abnormality is detected at step 814 according to a first monitored biological state, a second biological state monitored at step 820 may have similarities to the first biological state. For example, the first biological state monitored at step 812 may be a temperature of the patient 100. At step 820, the second biological state may be a temperature measurement performed at two or more other body locations by way of multiple biological sensors 102 or one biological sensor 102 having access to each location. In yet another embodiment the second biological state monitored at step 820 may differ from the first biological state monitored at step 812 only by the frequency of measurements. For example, when an onset of a fever is detected based on an hourly measurement at step 812, monitoring a temperature of the patient 100 may be increased at step 820 to a higher frequency (e.g., once every 15 mins or less). Although the biological state is monitored more frequently at step 820, the biological state (e.g., temperature) being monitored is still the same.

Method 800 can also be adapted so that the type of second biological state monitored at step 820 can be determined by user-input rather than an automated algorithm obtained by the biological sensor 102. For example, a clinician 101 can provide user input at a user interface of the computing device 202 (or the workstation 266 or the sensor management system 304). The user input can result in instructions being directed to the biological sensor 102 to monitor a particular biological state and corresponding a biological abnormality. The instructions provided by the clinician 101 via the computing device 202 (or the workstation 266 or the sensor management system 304) can also identify a protocol to be followed during the monitoring process. The user input may also come from the patient 100 via a user interface (e.g., button or touch-screen) of the biological sensor 102 or a device communicatively coupled to the biological sensor 102 (e.g., a mobile phone).

Method 800 can also be adapted to present a state of the biological sensor 102 at a user interface of the biological sensor 102, a user interface of the computing device 202, a user interface of the workstation 266, or a user interface of the sensor management system 304. The state of the biological sensor 102 can include without limitation an indication of any biological conditions that may have been detected, an identification of the protocol or instructions provided to the patient 100 and/or clinician, timer(s) associated with one or more detected adverse biological conditions, and so on.

Method 800 can also be further adapted to cause biological sensors 102 to share biological states measured with each other or with the computing device 202, workstation 266, or the sensor management system 304. The biological states measured can be the same (e.g., temperature, blood pressure, etc.), but at different locations of the patient's body where the biological sensors 102 are located. Differential measurements can be used to detect abnormalities in one part of the patient's body that may not be present at another location. Accordingly, adverse biological conditions may be more readily detected by way of differential measurements. Similarly, disparate biological states measured by different biological sensors 102 (e.g., pulse rate vs. blood pressure, temperature vs. perspiration) can be shared between biological sensors 102 or with the computing device 202, workstation 266, or the sensor management system 304. Such disparate readings can be helpful to a biological sensor 102 to determine when it may or may not be desirable to perform a biological measurement of a specific type. Differential measurements of disparate biological states may also be helpful in detecting one or more adverse biological conditions.

Additionally, method 800 can be adapted to cause biological sensors 102 to perform biological measurements in a transient manner. For example, a blood pressure measurement system carried by a clinician 101 can be configured with one or more wireless transmitters or transceivers that can generate a signal that causes biological sensors 102 coupled to the patient 100 to be triggered to perform a reading and provide such information to the blood pressure measurement system or computing device 202, workstation 266 or sensor management system 304. The triggering can be performed by RF energy received by the biological sensor 102 and harvested to provide the biological sensor 102 sufficient energy to perform a measurement and provide the sensing data to the measurement system or computing device 202, workstation 266 or sensor management system 304 over a wireless transmission medium.

It will be appreciated that any of the embodiments of the subject disclosure, singly or in combination, can be adapted for use in a non-clinical setting, where individuals monitor their own biological states and mitigate adverse biological conditions accordingly. Additionally, the computing device 202, workstation 266 and/or sensor management system 304 can be replaced with a computer, mobile communication device (e.g., smartphone, tablet or otherwise) of a user to perform in whole or in part the methods described in the subjection disclosure.

While for purposes of simplicity of explanation, the respective processes are shown and described as a series of blocks in FIG. 8A, it is to be understood and appreciated that the claimed subject matter is not limited by the order of the blocks, as some blocks may occur in different orders and/or concurrently with other blocks from what is depicted and described herein. Moreover, not all illustrated blocks may be required to implement the methods described herein.

Figure 8F:
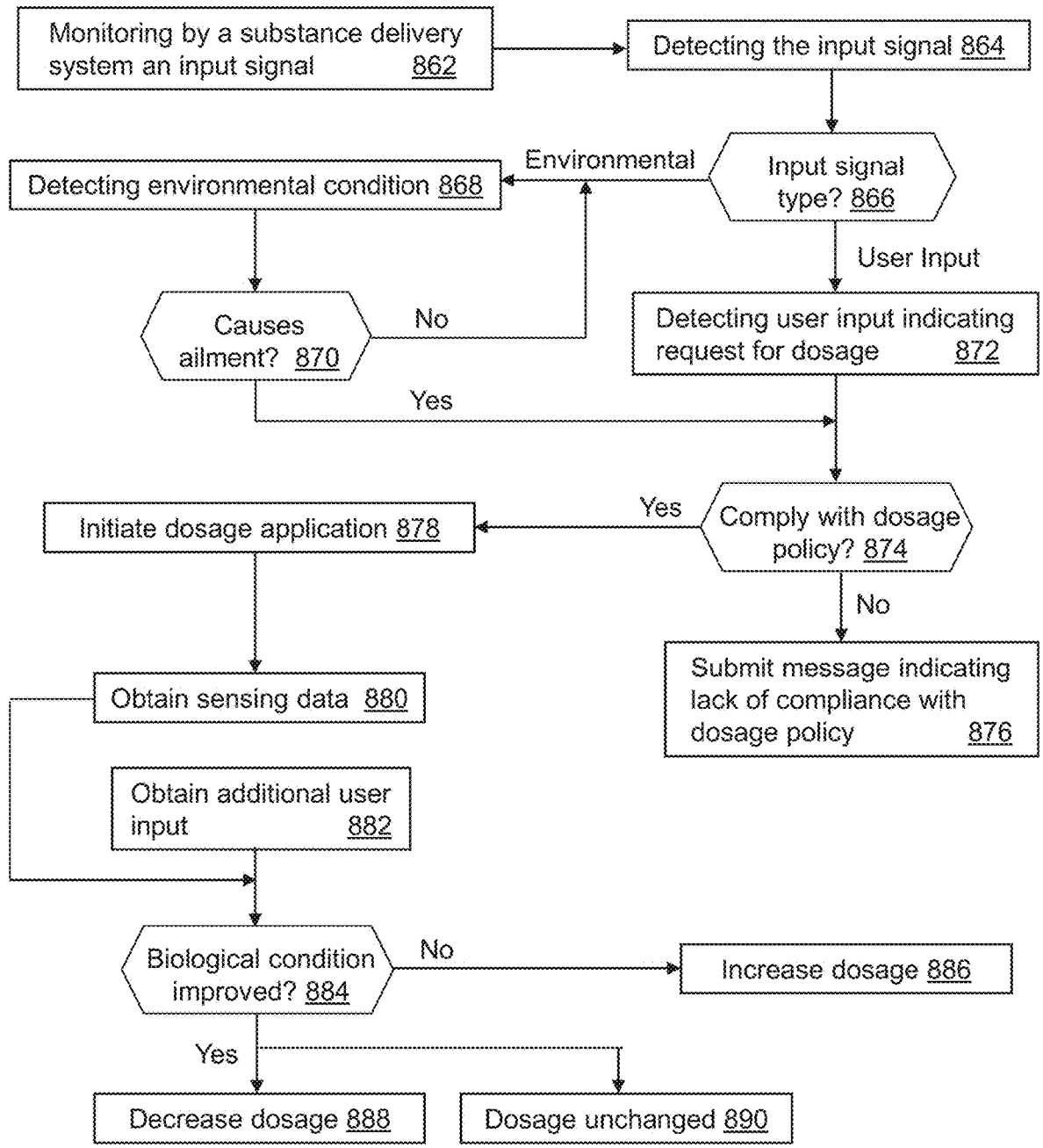
FIG. 8F is a block diagram illustrating an example, non-limiting embodiment of a method for drug or other substance delivery in accordance with various aspects of the subject disclosure described herein.

Now turning to FIG. 8F, a block diagram illustrating an example, non-limiting embodiment of a method 860 for drug or other substance delivery in accordance with various aspects of the subject disclosure is shown. Method 860 can begin with step 862 where a substance delivery system monitors an input signal at step 862. The substance delivery system can utilize a portion or all of the components shown for the biological sensor 102 of FIG. 4. For example, the substance delivery system can include the transceiver 402, the motion sensor 418, the controller 406, the UI 401, the memory 404, the drug delivery system 408, the biometric sensor 409, and one or more sensors 410. Other variants of the substance delivery system can be utilized in the application of method 860. The substance delivery system can be placed on an individual (similar to a patch) utilizing an adhesive surface of the substance delivery system, which is adapted to make contact with the skin of the individual. The substance delivery system can be placed on any portion of the user's body as shown by the illustrations of FIG. 1. Alternatively, or in combination, the substance delivery system can be embedded in a sleeve or sock as illustrated in FIGS. 8B-8E, or via some other wearable garment utilized by the user.

In one embodiment, the input signal can be generated responsive to user input applied to the UI 401 by way of a depression of a button of the input device 403, or by way of sensing a finger (or other body part) of the user via a touch sensitive interface of the input device 403 or display 405 as previously described. In another embodiment, the input signal can comprise an environmental signal that can be used for detecting an environmental condition that may have an adverse effect on the user. For example, the environmental signal can comprise a signal generated by the motion sensor 418 that can facilitate detection of certain motion of the individual that may cause motion sickness. In other embodiments, the environmental signal can comprise a signal generated by one or more of the sensors 410 indicating a level of air particulates, which may cause an ailment to an individual. The input signal in other embodiments can further provide biometric information generated by the biometric sensor 409, which can be used to identify the individual. Any of the foregoing embodiments of the input signal can be used singly or in any combination when applying the embodiments of method 860.

Upon detecting the input signal at step 864, the substance delivery system can determine if the input signal is an environmental signal or user input. Such a determination can be made, for example, by determining whether the input signal is provided by the UI 401, one of the sensors 410, or by the motion sensor 418. If the input signal comprises user input, the substance delivery system can detect from the input signal at step 872 that the user input comprises a request for a dosage of a substance contained in the substance delivery system. The substance can comprise a prescribed medication or an over-the-counter substance.

For example, the substance delivery system can be a nicotine patch (adapted to the embodiments of method 860) that the individual can use to control a nicotine addiction. The nicotine patch can supply incremental dosages that can assist an individual in the process of breaking a smoking or tobacco chewing habit. When a user of a nicotine patch feels, for example, that s/he is experiencing a craving for a cigarette or chewing tobacco, the user can press a button (on the input device 403) of the nicotine patch or tap the nicotine patch (by way of a touch sensitive sensor of the input device 403). The user input initiated by the user is detected by the input device 403, which generates the input signal detected at step 872.

The foregoing embodiments can be applied to other substance delivery systems such as, for example, a motion sickness patch, an anti-allergen patch, and/or other substance delivery applications. In the case of a motion sickness patch or an anti-allergen patch, the user can apply user input to the input device 403 to generate an input signal indicative of a request for a dosage to prevent the user's ailment.

Referring back to step 866, if the input signal is instead an environmental signal, the substance delivery system can proceed to step 868 to process the input signal and detect that the user may be experiencing an environmental condition that can cause the user to experience an ailment (e.g., motion sickness, allergy, asthma, etc.). For example, the input signal can originate from motion sensing data provided by the motion sensor 418. The substance delivery system can be adapted to detect from the input signal a sequence of movements experienced by the user. If, for example, the user is experiencing a swaying motion such as one would experience on a boat, the substance delivery system can determine from such motion whether the user would likely experience motion sickness.

In other embodiments, for example, method 860 can be adapted so that the substance delivery system utilizes the location receiver 416. In this embodiment, the substance delivery system can be configured to detect from the input signal location coordinates provided by the location receiver 416 that indicate the user is on land. The substance delivery system can also be adapted to utilize the orientation sensor 420, and detect from the input signal orientation data provided by the orientation sensor 420 and motion sensing data provided by the motion sensor 418, which collectively indicate the user is in an automobile with a trajectory towards a section of the road with numerous curves, which can cause the user motion sickness. In these embodiments, the substance delivery system can be configured to preemptively prevent motion sickness by the user by requesting a dosage with sufficient time to assist the user before the automobile reaches the curved sections of the road.

In other embodiments, the input signal can represent signals from one or more of the sensors 410 which detect one or more types of air particulates. For example, one or more sensors 410 can be configured to detect airborne pollens of certain trees, grasses and weeds, dust mite particles, mold spores, cat and/or dog dander, latex dust, or other particulates that can cause an allergy. One or more other sensors 410 can be configured to detect air particulates that indicate a level of air pollution (dust, soot, diesel exhaust, wood smoke, etc.) that can cause an onset of asthma. The subject disclosure contemplates other embodiments for monitoring other environmental conditions which can cause the user an ailment.

When an environmental condition is detected at step 870 that can cause the user an ailment or user input is detected at step 872 requesting a dosage to proactively alleviate an ailment experienced by the user, the substance delivery system can proceed to step 874 and determine if the dosage requested complies with a dosage policy set by medical professionals, health institutions (e.g., Food and Drug Administration), and/or the vendor of the substance delivery system. The dosage policy can comprise one or more metrics to determine compliance. For example, a first metric of the dosage policy can comprise a dosage threshold. The dosage threshold can identify an interval between which deliveries of the dosage are allowed.

For instance, if the user of the substance delivery system initiates multiple requests for a dosage in a short period of time (e.g., double tapping the patch or depressing a button repeatedly), the first request may be complied with, but subsequent requests may not be accepted. The interval applied to the dosage threshold may be determined according to the amount of the substance provided by each dosage, and the expected duration of relieve that the dosage would provide the user. The substance delivery system can be adapted with a timer to track time between deliveries of dosages to assure the dosage threshold is not exceeded. By preventing multiple dosages within the interval, the vendor of the substance delivery system avoids an overdose condition that may be harmful to the user and/or may lessen the effectiveness of the substance delivery system to address the user's ailment.

In another embodiment, the dosage threshold can comprise a number that sets a limit on deliveries of the dosage over a certain interval. For example, in this embodiment the dosage threshold can set a limit on how many dosages can be given in a day. For instance, the dosage threshold can indicate that not more than 3 doses of a particular substance can be provided to a user in a 24 hour period. A timer can also be used to track such a period to avoid exceeding the dosage limit set by the dosage threshold.

If the dosage policy is not satisfied at step 874, the substance delivery system can be adapted to submit a message indicating that the request does not comply with the dosage policy. For example, the substance delivery system can transmit a wireless message to a communication device of the user (e.g., mobile phone, computer, tablet) indicating that a request for a dosage has been rejected due to non-compliance with the dosage policy. Alternatively, or in combination, the substance delivery system can present the message at the display 405 of the substance delivery system, or present an audible message (e.g., synthesized speech, beeps or other sounds). The message can further indicate to the user that the user must wait a certain period before the next dosage can be provided. Alternatively, the message can indicate to the user that a maximum number of dosages have been provided, and that the user must wait 24 hours (or other suitable time period) before requesting an additional dosage. In situations where a maximum number of doses has not been exceeded, the dosage request can be queued by the substance delivery system, and upon expiration of the interval timer, the dosage can be provided.

Referring back to step 874, if the dosage request complies with the dosage policy, the substance delivery system can proceed to step 878 and deliver the dosage via the drug delivery system 408. In this step, the substance delivery system can be adapted to verify that the dosage was successfully delivered by verifying that a microfluidic gate of the drug delivery system 408 was actuated or opened. Alternatively, or in combination, the substance delivery system can verify that the dosage was delivered according to the monitoring steps 880-890 as will be described shortly. At step 880, the substance delivery system can be further configured to obtain sensing data to determine the effectiveness of the dosage. The sensing data can be obtained immediately or after a time period when the dosage is expected to take effect. The sensing data can be processed by the substance delivery system to determine at step 884 whether a biological condition controllable by the dosage has improved or at least not worsened. Steps 880 and 884 can be performed over a gradual period of time to determine if an improvement trend (or trend for maintaining a desired state of the biological condition) is detected. If there is no improvement or a worsening of the biological condition, the substance delivery system can proceed to step 886 to increase the dosage 886. The increase can be determined by the severity of the biological condition, its duration, and any other factors that may be pertinent to such a determination.

The increase can also be determined by a drug delivery protocol, which the substance delivery system can be configured to follow. In some embodiments, for example, the drug delivery protocol can be executed by the substance delivery system with a look-up table that can be indexed by a number of variables including, but not limited to, severity of the biological condition, frequency of occurrence of the biological condition, duration of the biological condition, historical data relating to the biological condition, medical records of the user, and so on. The increase in dosage can, however, be moderated by the dosage policy of step 874. For example, the dosage policy can dictate that dosages cannot be increased more than a certain number of times per minute, hour, day week, and so on. A history of dosages can be used to determine if the increase complies with the dosage policy.

Alternatively, if at step 884, it is determined that the biological condition has improved substantially, the substance delivery system can proceed to step 888 and decrease the dosage. The amount of the decrease can also be determined by the drug delivery protocol and the level of improvement in the biological condition. If the improvement is at a normal or expected level, the substance delivery system can be configured at step 890 to maintain the dosage level as is. If the dosage level is decreased, however, the substance delivery system can be configured to determine whether the decreased dosage conforms to the dosage policy. For example, the dosage policy can set a limit on how many times a dosage can be decreased at certain periods (minute, hour, day week, and so on). It is further noted when an adjustment is made to future dosages, the dosage policy can be adjusted also to accommodate the adjustment. For example, if the dosage is decreased, the dosage policy may be adjusted to increase the frequency of dosages provided during an interval (e.g., minutes, hours, days, weeks, etc.). Similarly, if the dosage is increased, the dosage policy may be adjusted to decrease the frequency of dosages provided during an interval (e.g., minutes, hours, days, weeks, etc.).

Referring back to step 884, a state of the biological condition can also be determined qualitatively without sensing data by obtaining additional user input from the user. For example, the substance delivery system can be configured to request that the user provide an indication whether the user is feeling better. The request can be presented at the display 405, or by way of an audible signal generated by the audio system 407 (e.g., two beeps representing a status request). The user in response to the request can provide at step 882 user input at the UI 401 by tapping a touch-sensitive feature of the input device 403 according to a known sequence (for indicating the user is feeling the same, better or worse), depressing a button of the input device 403 (according to the known sequence), speaking ("I'm feeling better", "I'm not feeling better", I'm feeling worse") which is detectable by the audio system 407, or any combinations thereof. Alternatively, the user can provide the additional user input at step 882 to indicate how the user is feeling without being prompted by the substance delivery system. Steps 880 and 882 can also be performed together to increase a confidence level that the biological condition has or has not improved.

It will be appreciated that method 860 can be adapted in other ways that do not depart from the scope of the subject disclosure. For example, method 860 can be adapted so that the sensor management system 304, the computing device 201, or a computer or portable communication device of the user (e.g., a cell phone, tablet, etc.) performs some or all of the steps of method 860. For instance, the sensor management system 304, the computing device 201, or a computer or portable communication device of the user can receive an input signal from the substance delivery system, determine whether the input signal is an environmental signal, a user input, or both, and determine therefrom whether a dosage is required as previously described. The sensor management system 304, the computing device 201, or a computer or portable communication device of the user can then determine if providing the dosage complies with the dosage policy and from this determination provide the dosage or reject the request for the dosage and provide a message to equipment of the user (e.g., the substance deliver device, computer or cell phone of the user) indicating a reason for rejecting the dosage and/or other instructions.

The sensor management system 304, the computing device 201, or a computer or portable communication device of the user can also be configured to obtain sensor data and/or user input initiated by the user to determine if the dosage provided has improved the biological condition of the user. Upon determining whether or not the dosage improves the user's biological condition, the sensor management system 304, the computing device 201, or a computer or portable communication device of the user can further adjust an amount of the substance provided in future dosages (if such adjustment is complied with the dosage policy), or leave the amount of the substance provided in future dosages as is. When an adjustment is made, in some embodiments, the sensor management system 304, the computing device 201, or a computer or portable communication device of the user can also be configured to direct the substance delivery system to adjust the amount of substance delivered per dosage.

Method 860 can also be adapted in other ways. For example, method 860 can be adapted to not obtain sensing data or user input to determine whether the dosage has improved the biological condition of the user, thereby removing a need for steps 880 through 890. Alternatively, method 860 can be adapted to receive and process user input from the user at step 882 or obtain sensor data at step 880, but not both. Additionally, the embodiments of method 860 can be combined in whole or in part with other embodiments described in the subject disclosure. Other adaptations of method 860 are contemplated by the subject disclosure.

While for purposes of simplicity of explanation, the respective processes are shown and described as a series of blocks in FIG. 8F, it is to be understood and appreciated that the claimed subject matter is not limited by the order of the blocks, as some blocks may occur in different orders and/or concurrently with other blocks from what is depicted and described herein. Moreover, not all illustrated blocks may be required to implement the methods described herein.

Figure 9:
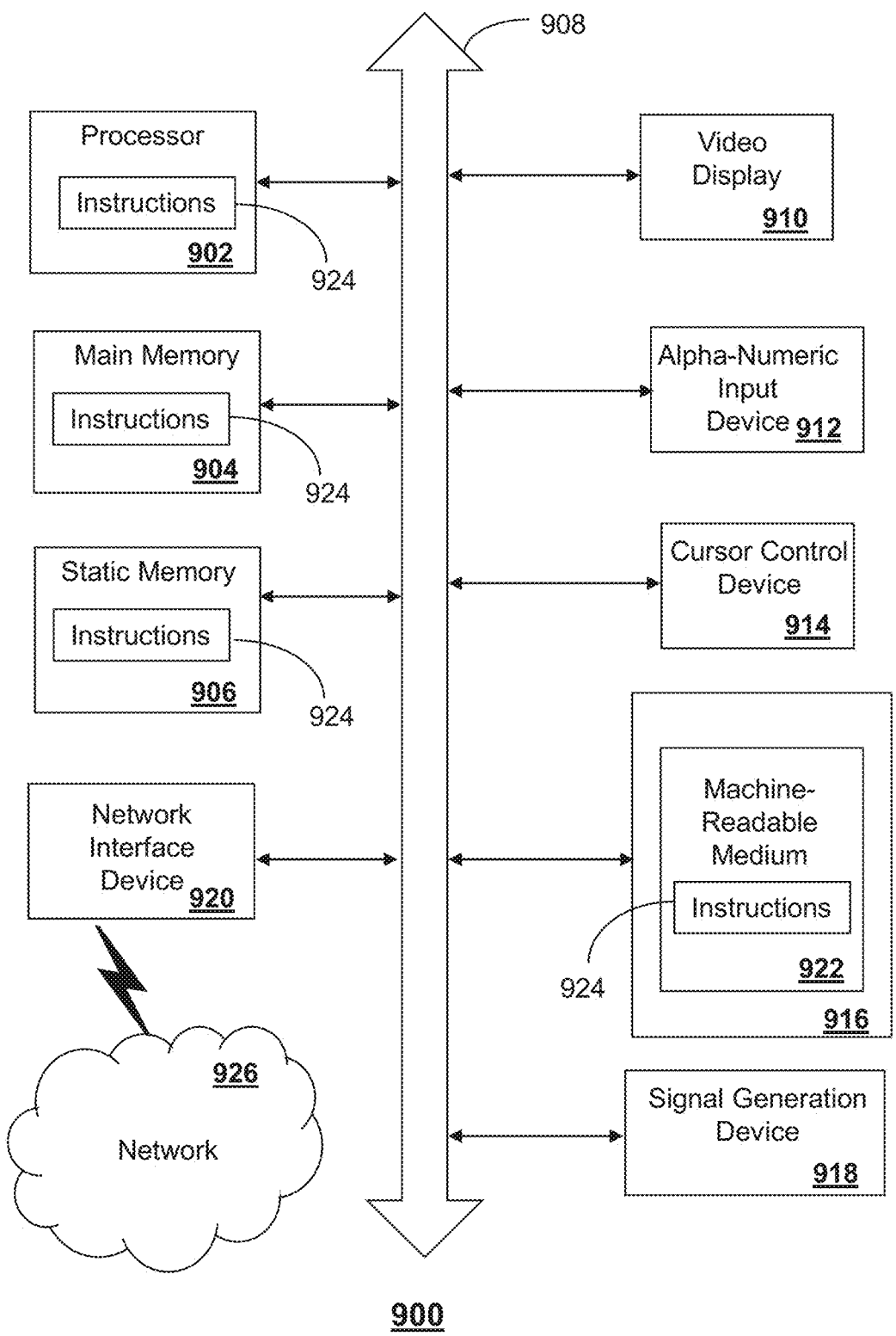
FIG. 9 is a diagrammatic representation of a machine in the form of a computer system within which a set of instructions, when executed, may cause the machine to perform any one or more of the methods of the subject disclosure described herein.

FIG. 9 depicts an exemplary diagrammatic representation of a machine in the form of a computer system 900 within which a set of instructions, when executed, may cause the machine to perform any one or more of the methods described above. One or more instances of the machine can operate, for example, as the devices depicted in the drawings of the subject disclosure. In some embodiments, the machine may be connected (e.g., using a network 926) to other machines. In a networked deployment, the machine may operate in the capacity of a server or a client user machine in a server-client user network environment, or as a peer machine in a peer-to-peer (or distributed) network environment.

The machine may comprise a server computer, a client user computer, a personal computer (PC), a tablet, a smart phone, a laptop computer, a desktop computer, a control system, a network router, switch or bridge, or any machine capable of executing a set of instructions (sequential or otherwise) that specify actions to be taken by that machine. It will be understood that a communication device of the subject disclosure includes broadly any electronic device that provides voice, video or data communication. Further, while a single machine is illustrated, the term "machine" shall also be taken to include any collection of machines that individually or jointly execute a set (or multiple sets) of instructions to perform any one or more of the methods discussed herein.

The computer system 900 may include a processor (or controller) 902 (e.g., a central processing unit (CPU)), a graphics processing unit (GPU, or both), a main memory 904 and a static memory 906, which communicate with each other via a bus 908. The computer system 900 may further include a display unit 910 (e.g., a liquid crystal display (LCD), a flat panel, or a solid state display). The computer system 900 may include an input device 912 (e.g., a keyboard), a cursor control device 914 (e.g., a mouse), a disk drive unit 916, a signal generation device 918 (e.g., a speaker or remote control) and a network interface device 920. In distributed environments, the embodiments described in the subject disclosure can be adapted to utilize multiple display units 910 controlled by two or more computer systems 900. In this configuration, presentations described by the subject disclosure may in part be shown in a first of the display units 910, while the remaining portion is presented in a second of the display units 910.

The disk drive unit 916 may include a tangible computer-readable storage medium 922 on which is stored one or more sets of instructions (e.g., software 924) embodying any one or more of the methods or functions described herein, including those methods illustrated above. The instructions 924 may also reside, completely or at least partially, within the main memory 904, the static memory 906, and/or within the processor 902 during execution thereof by the computer system 900. The main memory 904 and the processor 902 also may constitute tangible computer-readable storage media.

Dedicated hardware implementations including, but not limited to, application specific integrated circuits, programmable logic arrays and other hardware devices can likewise be constructed to implement the methods described herein. Application specific integrated circuits and programmable logic array can use downloadable instructions for executing state machines and/or circuit configurations to implement embodiments of the subject disclosure. Applications that may include the apparatus and systems of various embodiments broadly include a variety of electronic and computer systems. Some embodiments implement functions in two or more specific interconnected hardware modules or devices with related control and data signals communicated between and through the modules, or as portions of an application-specific integrated circuit. Thus, the example system is applicable to software, firmware, and hardware implementations.

In accordance with various embodiments of the subject disclosure, the operations or methods described herein are intended for operation as software programs or instructions running on or executed by a computer processor or other computing device, and which may include other forms of instructions manifested as a state machine implemented with logic components in an application specific integrated circuit or field programmable gate array. Furthermore, software implementations (e.g., software programs, instructions, etc.) including, but not limited to, distributed processing or component/object distributed processing, parallel processing, or virtual machine processing can also be constructed to implement the methods described herein. It is further noted that a computing device such as a processor, a controller, a state machine or other suitable device for executing instructions to perform operations or methods may perform such operations directly or indirectly by way of one or more intermediate devices directed by the computing device.

While the tangible computer-readable storage medium 922 is shown in an example embodiment to be a single medium, the term "tangible computer-readable storage medium" should be taken to include a single medium or multiple media (e.g., a centralized or distributed database, and/or associated caches and servers) that store the one or more sets of instructions. The term "tangible computer-readable storage medium" shall also be taken to include any non-transitory medium that is capable of storing or encoding a set of instructions for execution by the machine and that cause the machine to perform any one or more of the methods of the subject disclosure. The term "non-transitory" as in a non-transitory computer-readable storage includes without limitation memories, drives, devices and anything tangible but not a signal per se.

The term "tangible computer-readable storage medium" shall accordingly be taken to include, but not be limited to: solid-state memories such as a memory card or other package that houses one or more read-only (non-volatile) memories, random access memories, or other re-writable (volatile) memories, a magneto-optical or optical medium such as a disk or tape, or other tangible media which can be used to store information. Accordingly, the disclosure is considered to include any one or more of a tangible computer-readable storage medium, as listed herein and including art-recognized equivalents and successor media, in which the software implementations herein are stored.

Although the present specification describes components and functions implemented in the embodiments with reference to particular standards and protocols, the disclosure is not limited to such standards and protocols. Each of the standards for Internet and other packet switched network transmission (e.g., TCP/IP, UDP/IP, HTML, HTTP) represent examples of the state of the art. Such standards are from time-to-time superseded by faster or more efficient equivalents having essentially the same functions. Wireless standards for device detection (e.g., RFID), short-range communications (e.g., Bluetooth®, WiFi, Zigbee®), and long-range communications (e.g., WiMAX, GSM, CDMA, LTE) can be used by computer system 900.

The illustrations of embodiments described herein are intended to provide a general understanding of the structure of various embodiments, and they are not intended to serve as a complete description of all the elements and features of apparatus and systems that might make use of the structures described herein. Many other embodiments will be apparent to those of skill in the art upon reviewing the above description. The exemplary embodiments can include combinations of features and/or steps from multiple embodiments. Other embodiments may be utilized and derived therefrom, such that structural and logical substitutions and changes may be made without departing from the scope of this disclosure. Figures are also merely representational and may not be drawn to scale. Certain proportions thereof may be exaggerated, while others may be minimized. Accordingly, the specification and drawings are to be regarded in an illustrative rather than a restrictive sense.

Although specific embodiments have been illustrated and described herein, it should be appreciated that any arrangement which achieves the same or similar purpose may be substituted for the embodiments described or shown by the subject disclosure. The subject disclosure is intended to cover any and all adaptations or variations of various embodiments. Combinations of the above embodiments, and other embodiments not specifically described herein, can be used in the subject disclosure. For instance, one or more features from one or more embodiments can be combined with one or more features of one or more other embodiments. In one or more embodiments, features that are positively recited can also be negatively recited and excluded from the embodiment with or without replacement by another structural and/or functional feature. The steps or functions described with respect to the embodiments of the subject disclosure can be performed in any order. The steps or functions described with respect to the embodiments of the subject disclosure can be performed alone or in combination with other steps or functions of the subject disclosure, as well as from other embodiments or from other steps that have not been described in the subject disclosure. Further, more than or less than all of the features described with respect to an embodiment can also be utilized.

Less than all of the steps or functions described with respect to the exemplary processes or methods can also be performed in one or more of the exemplary embodiments. Further, the use of numerical terms to describe a device, component, step or function, such as first, second, third, and so forth, is not intended to describe an order or function unless expressly stated so. The use of the terms first, second, third and so forth, is generally to distinguish between devices, components, steps or functions unless expressly stated otherwise. Additionally, one or more devices or components described with respect to the exemplary embodiments can facilitate one or more functions, where the facilitating (e.g., facilitating access or facilitating establishing a connection) can include less than every step needed to perform the function or can include all of the steps needed to perform the function.

In one or more embodiments, a processor (which can include a controller or circuit) has been described that performs various functions. It should be understood that the processor can be multiple processors, which can include distributed processors or parallel processors in a single machine or multiple machines. The processor can be used in supporting a virtual processing environment. The virtual processing environment may support one or more virtual machines representing computers, servers, or other computing devices. In such virtual machines, components such as microprocessors and storage devices may be virtualized or logically represented. The processor can include a state machine, application specific integrated circuit, and/or programmable gate array including a Field PGA. In one or more embodiments, when a processor executes instructions to perform "operations", this can include the processor performing the operations directly and/or facilitating, directing, or cooperating with another device or component to perform the operations.

The Abstract of the Disclosure is provided with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

What is claimed is:

1. A non-transitory machine-readable storage medium, comprising executable instructions that, when executed by a processor, facilitate performance of operations, comprising:
    detecting an input signal by a sensing device coupled to a body part of an individual, wherein the input signal is indicative of at least one of a request by the individual or a first determination that an environmental condition measurement sensed by the sensing device has been detected;
    determining whether to deliver to the body part of the individual a dosage of a substance for treating motion sickness, the substance stored in a microfluidic system of the sensing device based on:
        the at least one of the request or the first determination; and
        a second determination indicative of whether delivering the dosage satisfies a time requirement of a dosage policy, the time requirement comprising a minimum amount of time required between consecutive deliveries of the dosage, wherein the minimum amount of time is based at least in part on an amount of the substance that will lessen an effectiveness of the substance when delivered to the individual; and
    responsive to determining whether to deliver the dosage:
        initiating, by the microfluidic system, delivery of the dosage of the substance to the body part of the individual;
        obtaining, by the sensing device, sensing data associated with a biological measurement of the individual; and
        determining from the biological measurement whether the dosage has improved a biological condition of the individual adjustable by the dosage.

2. The machine-readable storage medium of claim 1, wherein the input signal is generated based on the request, the request being received at a user interface of the sensing device responsive to a user input being applied to the user interface.

3. The machine-readable storage medium of claim 2, wherein the user input corresponds to an indication by the individual to deliver the dosage.

4. The machine-readable storage medium of claim 1, wherein the environmental condition measurement is generated by an environmental sensor of the sensing device.

5. The machine-readable storage medium of claim 4, wherein the environmental sensor comprises a motion sensor that generates the environmental condition measurement.

6. The machine-readable storage medium of claim 5, wherein the determining from the input signal whether to deliver to the body part of the individual the dosage comprises:
    detecting from the environmental condition measurement a sequence of movements; and
    determining whether the sequence of movements will cause the individual to experience motion sickness.

7. The machine-readable storage medium of claim 1, wherein the determining that the dosage satisfies the dosage policy comprises determining that the dosage does not exceed a dosage threshold.

8. The machine-readable storage medium of claim 7, wherein the dosage threshold comprises a maximum number of deliveries of the dosage over a time interval.

9. The machine-readable storage medium of claim 1, wherein the operations further comprise generating a message responsive to determining that delivery of the dosage does not satisfy the dosage policy.

10. The machine-readable storage medium of claim 9, wherein the message is presented at a user interface of the sensing device or a device communicatively coupled to the sensing device.

11. The machine-readable storage medium of claim 1, wherein the operations further comprise reducing an amount of the substance at a subsequent delivery of the dosage responsive to determining that the biological condition has improved.

12. The machine-readable storage medium of claim 1, wherein the operations further comprise increasing an amount of the substance at a subsequent delivery of the dosage responsive to determining that the biological condition has not improved.

13. A method, comprising:
    detecting, by a substance delivery system coupled to a body part of an individual, an input signal indicative of a first determination that an environmental condition measurement has been sensed by a sensing device of the substance delivery system;
    determining whether to deliver to the body part of the individual a dosage of a substance for treating motion sickness, the substance stored in the substance delivery system based on:
        the first determination; and
        a second determination indicative of whether delivering the dosage satisfies a time requirement of a dosage policy, the time requirement comprising a minimum amount of time required between consecutive deliveries of the dosage, wherein the minimum amount of time is based at least in part on an amount of the substance that will lessen an effectiveness of the substance when delivered to the individual; and responsive to determining whether to deliver the dosage, initiating, by the substance delivery system, delivery of the dosage of the substance to the body part of the individual according to the dosage policy.

14. The method of claim 13, wherein the input signal is generated responsive to detecting user input applied to a user interface of the substance delivery system or is generated by a motion sensor of the substance delivery system that facilitates detection of movements that cause the individual to experience motion sickness.

15. The method of claim 13, further comprising adjusting, by the substance delivery system, the dosage responsive to receiving user input indicating whether a parameter associated with a biological condition of the individual has been reduced from a first level to a second level by the dosage.

16. A system, comprising:
a processor; and
a memory that stores executable instructions that, when executed by the process, facilitate performance of operations, comprising:
receiving a signal from a device coupled to a body part of an individual, wherein the signal is indicative of a first determination that an environmental condition measurement has been sensed by a sensing device;
determining whether to deliver to the body part of the individual a dosage of a substance for treating motion sickness, the substance stored in the substance delivery system based on:
the first determination; and
a second determination indicative of whether delivering the dosage exceeds a time requirement associated with a dosage threshold, the time requirement comprising a minimum amount of time required between consecutive deliveries of the dosage, wherein the minimum amount of time is based at least in part on an amount of the substance that will lessen an effectiveness of the substance when delivered to the individual; and responsive to determining whether to deliver the dosage, directing the device to initiate delivery of the dosage of the substance to the body part of the individual.

17. The system of claim 16, wherein the signal is generated responsive to detecting user input applied to a user interface of the device.

18. The system of claim 16, wherein the environmental condition measurement is indicative of motion experienced by the individual, or particulates in air breathable by the individual.

19. The system of claim 16, wherein the environmental condition measurement is indicative of a location of the individual and an indication, by motion detected by the device, that the individual is traveling in an automobile, wherein directing the device to initiate delivery of the dosage is based at least in part on the location of the individual and the indication that the individual is traveling in the automobile.

20. The system of claim 16, wherein the minimum amount of time is further determined based on an amount of the substance associated with an overdose condition, or an expected duration of relief that the dosage will provide the individual.

* * * * *